United States Patent
Perfettini et al.

(10) Patent No.: US 11,603,568 B2
(45) Date of Patent: Mar. 14, 2023

(54) NOX2 AS A BIOMARKER OF RADIOTHERAPY EFFICIENCY IN CANCER PATIENTS

(71) Applicant: Institut Gustave-Roussy, Villejuif (FR)

(72) Inventors: Jean-Luc Perfettini, Meaux (FR); Eric Deutsch, Paris (FR); Awatef Allouch, Bry-sur-Marne (FR)

(73) Assignee: Institut Gustave Roussy, Villejuif (FR)

( * ) Notice: Subject to any disclaimer, the term of this patent is extended or adjusted under 35 U.S.C. 154(b) by 108 days.

(21) Appl. No.: 16/333,409

(22) PCT Filed: Sep. 19, 2017

(86) PCT No.: PCT/EP2017/073677
§ 371 (c)(1),
(2) Date: Mar. 14, 2019

(87) PCT Pub. No.: WO2018/050928
PCT Pub. Date: Mar. 22, 2018

(65) Prior Publication Data
US 2020/0181714 A1 Jun. 11, 2020

(30) Foreign Application Priority Data
Sep. 19, 2016 (EP) ..................................... 16306194

(51) Int. Cl.
*C12Q 1/68* (2018.01)
*C12Q 1/6886* (2018.01)
*C07K 14/80* (2006.01)

(52) U.S. Cl.
CPC ............ *C12Q 1/6886* (2013.01); *C07K 14/80* (2013.01); *C12Q 2600/106* (2013.01); *C12Q 2600/158* (2013.01); *G01N 2800/52* (2013.01)

(58) Field of Classification Search
CPC .................................................. C12Q 1/6886
See application file for complete search history.

(56) References Cited

FOREIGN PATENT DOCUMENTS

WO WO-2012129488 A2 * 9/2012 ....... G01N 33/57415

OTHER PUBLICATIONS

DePalma et al. Macrophage Regulation of Tumor Responses to Anticancer Therapies Cancer Cell 2013 vol. 23, 277-286 (Year: 2013).*
Lu et al. Androgens induce oxidative stress and radiation resistance in prostate cancer cells though NADPH oxidase Prostate Cancer and Prostatic Diseases (2010) 13, 39-46 (Year: 2010).*
Marullo et al. HPV16 E6 and E7 proteins induce a chronic oxidative stress response via NOX2 that causes genomic instability and increased susceptibility to DNA damage in head and neck cancer cells Carcinogenesis, 2015, vol. 36, No. 11, 1397-1406 (Year: 2015).*
Coates et al. At last, a predictive and prognostic marker for radiotherapy Breast Cancer Research 2010, vol. 12:106 pp. 1-2 (Year: 2010).*
Caillou et al. Tumor-Associated Macrophages (TAMs) Form an Interconnected Cellular Supportive Network in Anaplastic Thyroid Carcinoma PLoS One Jul. 2011 vol. 6 Issue 7 pp. 1-13 (Year: 2011).*
Valentini et al. Survival after radiotherapy in gastric cancer: Systematic reveiw and meta-analysis (2009) Radiotherapy and Oncology vol. 92, Issue 2, pp. 176-183 (Year: 2009).*
Bessede et al. Is Elevated Gastric Tissue NOX2 Associated with Lymphoma of Mucosa-Associated Lymphoid Tissue? (2012) Antioxidants & Redox Signaling vol. 16, No. 11, 1205-1211. (Year: 2012).*
Rahman (2013) Introduction to Flow Cytometry (Year: 2013).*
Trocme et al. Macrophage-specific NOX2 contributes to the development of lung emphysema though modultion of SIRT1/MMP-9 pathways (2015) J. Pathol. 235:65-78. (Year: 2015).*
Wang et al. Relationship between expression of NADPH oxidase 2 and invasion and prognosis of human gastric cancer (2015) World J. of Gastroenterol. 21(2): 6271-6279 (Year: 2015).*
Labclinics (2016) RNA Detection with Flow Cytometry, 8 pages (www.labclinics.com/en/category/flow-cytometry/) (Year: 2016).*
Rolny et al., "HRG Inhibits Tumor Growth and Metastasis by Inducing Macrophage Polarization and Vessel Normalization through Downregulation of PlGF," Cancer Cell, vol. 19, pp. 31-44, Jan. 2011.

(Continued)

*Primary Examiner* — Juliet C Switzer
(74) *Attorney, Agent, or Firm* — Rouget F. Henschel; Potomac Law Group, PLLC

(57) ABSTRACT

Although tumor-associated macrophages have been extensively studied in the control of response to radiotherapy, the molecular mechanisms involved in the ionizing radiation-mediated activation of macrophages remain elusive. Here the present inventors show that ionizing radiation induces the expression of interferon-regulatory factor 5 (IRF5) promoting thus macrophage activation toward a pro-inflammatory phenotype. They reveal that the activation of the Ataxia telangiectasia mutated (ATM) kinase is required for ionizing radiation-elicited macrophage activation, but also for macrophage reprogramming after treatments with γ-interferon, lipopolysaccharide or chemotherapeutic agent (such as cisplatin), underscoring the fact that the kinase ATM plays a central role during macrophage phenotypic switching toward a proinflammatory phenotype. They further demonstrate that NADPH oxidase 2 (NOX2)-dependent ROS production is upstream to ATM activation and is essential during this process. They also report that hypoxic conditions and the inhibition of any component of this signaling pathway (NOX2, ROS and ATM) impairs pro-inflammatory activation of macrophages and predicts a poor tumor response to preoperative radiotherapy in locally advanced rectal cancer. Altogether, these results identify a novel signaling pathway involved in macrophage activation that may enhance effectiveness of radiotherapy through the re-programming of tumor infiltrating macrophages.

Figure 1:
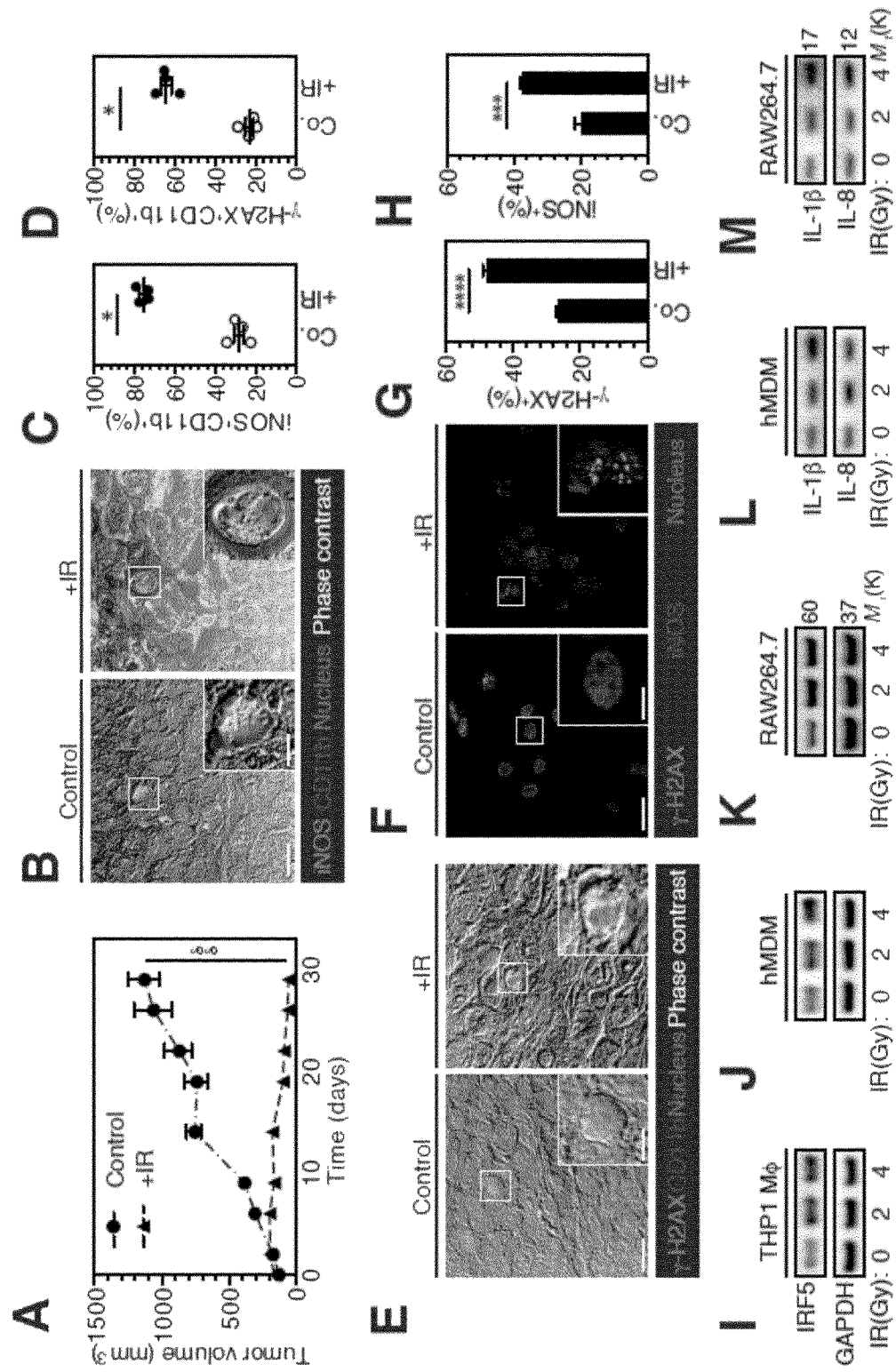
Figure 1:
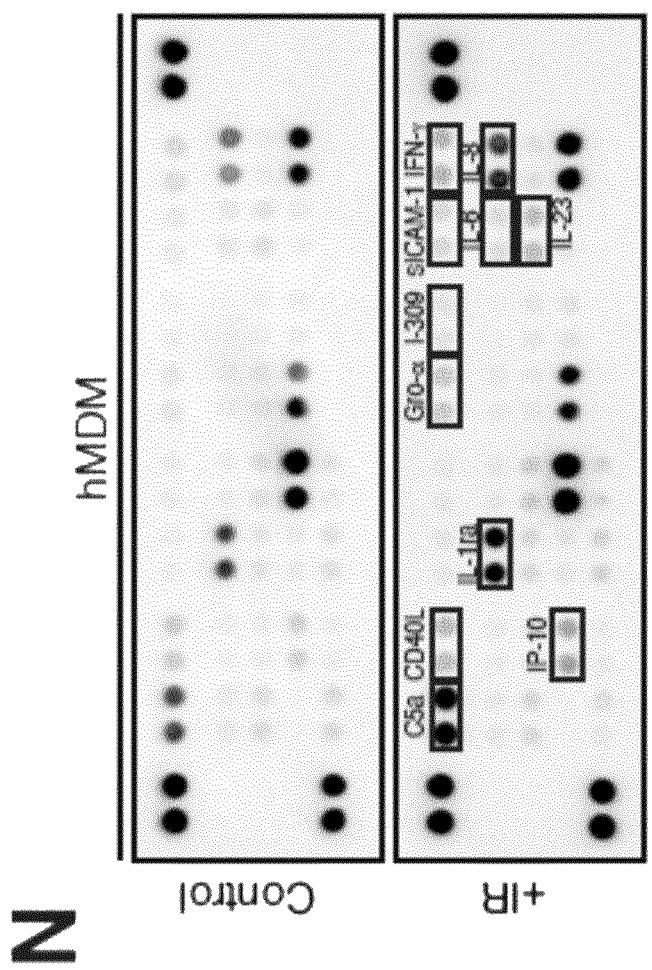
Figure 1:
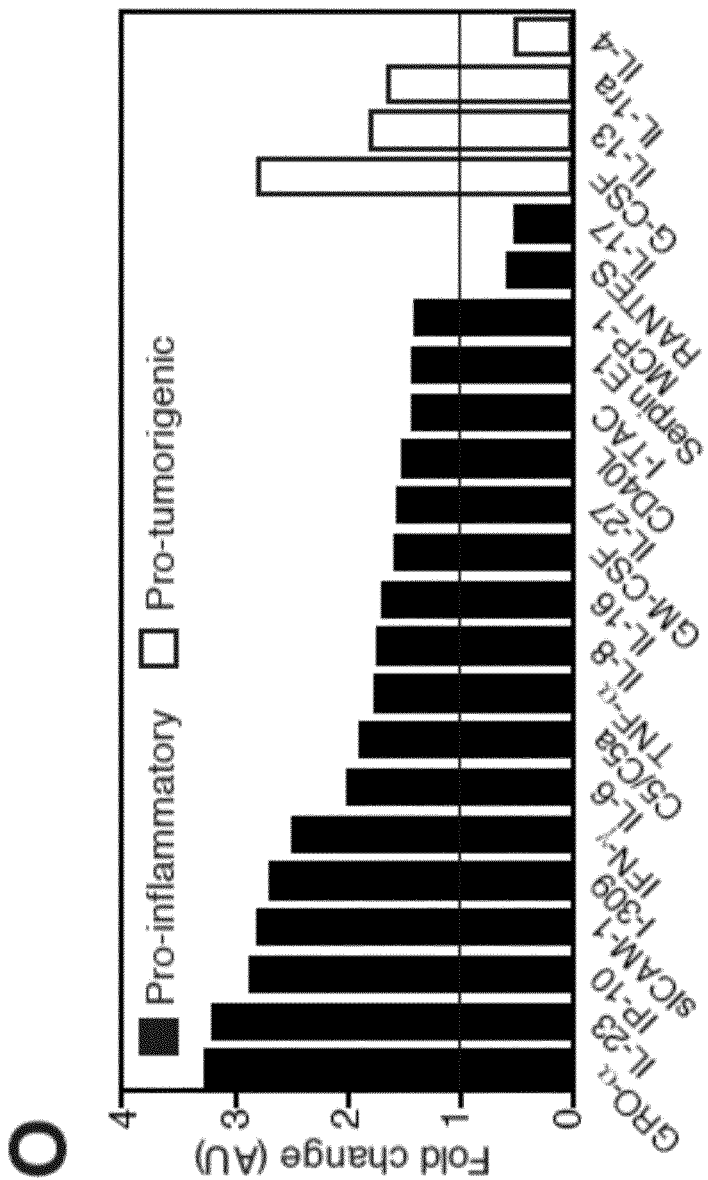

6 Claims, 13 Drawing Sheets
Specification includes a Sequence Listing.

(56) References Cited

OTHER PUBLICATIONS

Saliba et al., "IRF5:RelA Interaction Targets Inflammatory Genes in Macrophages," Cell Reports, vol. 8, pp. 1308-1317, Sep. 2014.
Satoh et al., "The Jmjd3-Irf4 axis regulates M2 macrophage polarization and host responses against helminth infection," Nature Immunology, vol. 11, No. 10, pp. 936-945, Oct. 2010.
So et al., "Roles of DNA Damage Response Proteins in Mitogen-Induced Thp-1 Differntiation into Macrophage," J. Cancer Biol. Res., 1(1), 2013.
So et al., "Translational initiation regulated by ATM in dendritic cells development," Cell Death and Disease, vol. 5, p. e1418, Sep. 2014.
Sorce et al., "NADPH oxidases as drug targets and biomarkers in neurodegenerative diseases: What is the evidence?," Free Radical Biology and Medicine, vol. 112, pp. 387-396, Aug. 2017.
Steidl et al., "Tumor-Associated Macrophages and Survival in Classic Hodgkin's Lymphoma," vol. 362, No. 10, pp. 875-885, Mar. 2010.
Tan et al., "Autophagy-induced RelB/p52 activation mediates tumour-associated macrophage repolarisation and suppression of hepatocellular carcinoma by natural compound baicalin," Cell Death and Disease, e1942, 2015.
Trakarnsanga et al., "Treatment of locally advanced rectal cancer: Controversies and questions," World Journal of Gastroenterology, vol. 18, Issue 39, pp. 5521-5532, Oct. 2012.
Weiss et al., "IRF5 controls both acute and chronic inflammation," PNAS, vol. 112, No. 35, pp. 11001-11006, Sep. 2015.
Weiss et al., "IRF5 Is a Specific Marker of Inflammatory Macrophages In Vivo," Mediators of Inflammation, vol. 2013, Article ID 245804, 2013.
Wen et al., "Increased metabolites of 5-lipoxygenase from hypoxic ovarian cancer cells promote tumor-associated macrophage infiltration," Oncogene, vol. 34, pp. 1241-1252, 2015.
Zhang et al., "ROS play a critical role in the differentiation of alternatively activated macrophages and the occurrence of tumor-associated macrophages," Cell Research, vol. 23, pp. 898-914, Jun. 2013.
Allouch et al., "p21-mediated RNR2 repression restricts HIV-1 replication in macrophages by inhibiting dNTP biosynthesis pathway," PNAS, pp. E3997-E4006, Sep. 2013.
Azzam et al., "Ionizing radiation-induced metabolic oxidative stress and prolonged cell injury," Cancer Lett., vol. 327, pp. 48-60, Dec. 2012.
Baskar et al., "Cancer and Radiation Therapy: Current Advances and Future Directions," International Journal of Medical Sciences, vol. 9, No. 3, pp. 193-199, Feb. 2012.
Bedard et al., "Th NOX Family of ROS-Generating NADPH Oxidases: Physiology and Pathophysiology," Physiol. Rev., vol. 87, pp. 245-313, 2007.
Blackford et al., "ATM, ATR, and DNA-PK: The Trinity at the Heart of DNA Damage Response," Molecular Cell Review, vol. 66, pp. 801-817, Jun. 2017.
Bowdridge et al., "Regulation of alternative macrophage activation by chromatin remodeling," Nature Immunology, vol. 11, No. 10, pp. 879-881, Oct. 2010.
Buhtoiarov et al., "Anti-tumour synergy of cytotoxic chemotherapy and anti-CD40 plus CpG-ODN immunotherapy through repolarization of tumour-associated macrophages," Immunology, vol. 132, pp. 226-239, 2010.
Burma et al., "ATM Phosphorylates Hisone H2AX in Response to DNA Double-strand Breaks," The Journal of Biological Chemistry, vol. 276, No. 45, pp. 42462-42467, Nov. 2001.
Carmona et al., "The Systemic Lupus Erythematosus IRF5 Risk Haplotype is Associated with Systemic Sclerosis," PLOS One, vol. 8, Issue 1, p. e54419, January 2103.
Chiang et al., "Irradiation promotes an M2 macrophage phenotype in tumor hypoxia," Frontiers in Oncology, vol. 2, Article 89, Aug. 2012.
Chung et al., "Tumor-associated macrophages correlate with response to epidermal growth factor receptor-tyrosine kinase inhibitors in advanced non-small cell lung cancer," International Journal of Cancer, vol. 131, pp. E227-E235, 2012.
Coffelt et al., "Tumor-associated macrophages: Effectors of angiogenesis and tumor progression," Biochimica et Biophysica Acta, vol. 1796, pp. 11-18, Mar. 2009.
Colegio et al., "Functional polarization of tumour-associated macrophages by tumour-derived lactic acid," Nature, vol. 513, No. 7519, pp. 599-563, Sep. 2014.
Condeelis et al., "Macrophages: Obligate Partners for Tumor Cell Migration, Invasion, and Metastasis," Cell, vol. 124, pp. 263-266, Jan. 2006.
Coscia et al., "Zoledronic acid repolarizes tumour-associated macrophages and inhibits mammary carcinogenesis by targeting the mevalonate pathway," J. Cell Mol. Med., vol. 14, No. 12, pp. 2803-2815, 2010.
Cosin-Roger et al., "The activation of Wnt signaling by a STAT6-dependent macrophage phenotype promotes mucosal repair in murine IBD," Nature, vol. 9, No. 4, pp. 966-998, Jul. 2016.
De Palma et al., "Macrophage Regulation of Tumor Responses to Anticancer Therapies," Cancer Cell Review, vol. 23, pp. 277-286, Mar. 2013.
Eriksson et al., "Radiation-induced cell death mechanisms," Tumor Biol., vol. 31, pp. 363-372, May 2010.
Franklin et al., "The Cellular and Molecular Origin of Tumor-associated Macrophages," Science, vol. 344, No. 6186, pp. 921-925, May 2014.
Galli et al., "Phenotypic and functional plasticity of cells of innate immunity: macrophages, mast cells and neutrophils," Nat. Immunol., vol. 12, No. 11, pp. 1035-1044, Aug. 2012.
Georgoudaki et al., "Reprogramming Tumor-Associated Macrophages by Antibody Targeting Inhibits Cancer Progression and Metastasis," Cell Reports, vol. 15, pp. 2000-2011, May 2016.
Ghiringhelli et al., "Activation of the NLRP3 inflammasome in dendritic cells induces IL-1 beta-dependent adaptive immunity against tumors," Nature Medicine, vol. 15, No. 10, pp. 1170-1179, Oct. 2009.
Graham et al., "A common haplotype of interferon regulatory factor 5 (IRF5) regulates splicing and expression and is associated with increased risk of systemic lupus erythematosus," Nature Genetics, vol. 38, No. 5, pp. 550-555, May 2006.
Guo et al., "ATM Activation by Oxidative Stress," Science, vol. 330, pp. 517-521, Oct. 2010.
Hartlova et al., "DNA Damage Primes the Type I Interferon System via the Cytosolic DNA Sensor Sting to Promote Anti-Microbial Innate Immunity," Immunity, vol. 42, pp. 332-343, Feb. 2015.
Hekim et al., "Radiation triggering immune response and inflammation," Cancer Letters, vol. 368, pp. 156-163, 2015.
Jensen et al., "Macrophage Markers in Serum and Tumor Have Prognostic Impact in American Joint Committee on Cancer Stage I/II Melanoma," Journal of Clinical Oncology, vol. 27, No. 20, pp. 3330-3337, Jul. 2009.
Jia et al., "Association of the IRF5 rs2004640 polymorphism with rheumatoid arthritis: a meta-analysis," Rheumatol. Int., vol. 33, pp. 2757-2761, Jun. 2013.
Kapoor et al., "Transcription factors STAT6 and KLF4 implement macrophage polarization via the dual catalytic powers of MCPIP," J. Immunol., vol. 194, No. 12, pp. 6011-6023, Jun. 2015.
Klug et al., "Low-Dose Irradiation Programs Macrophage Differentiation to an iNOS+/M1 Phenotype that Orchestrates Effective T Cell Immunotherapy," Cancer Cell, vol. 24, pp. 589-602, Nov. 2013.
Krausgruber et al., "IRF5 is required for late-phase TNF secretion by human dendritic cells," Blood, vol. 115, No. 22, pp. 4421-4430, Jun. 2010.
Krausgruber et al., "IRF5 promotes inflammatory macrophage polarization and TH1-TH17 responses," Nature Immunology, vol. 12, No. 3, pp. 231-239, Mar. 2011.
Kroemer et al., "Immunogenic Cell Death in Cancer Therapy," Annu. Rev. Immunol., vol. 31, pp. 51-72, 2013.
Lambeth, "NOX Enzymes and the Biology of Reactive Oxygen," Nature Reviews, vol. 4, pp. 181-189, Mar. 2004.

(56) References Cited

OTHER PUBLICATIONS

Lee et al., "Prognostic Significance of Macrophage Infiltration in Leiomyosarcomas," Clin. Cancer Res., vol. 14, No. 5, pp. 1423-1430, Mar. 2008.
Lien et al., "Critical role of IRF-5 in regulation of B-cell differentiation," PNAS, vol. 107, No. 10, pp. 4664-4668, Mar. 2010.
Mandard et al., "Pathologic Assessment of Tumor Regression after Preoperative Chemoradiotherapy of Esophageal Carcinoma," Cancer, vol. 73, No. 11, pp. 2680-2686, Jun. 1994.
Mantovani et al., "Macrophage polarization: tumor-associated macrophages as a paradigm for polarized M2 mononuclear phagocytes," Trends in Immunology, vol. 23, No. 11, pp. 549-555, Nov. 2002.
Mantovani et al., "The interaction of anticancer therapies with tumor-associated macrophages," J. Exp. Med., vol. 212, No. 4, pp. 435-445, 2015.
Mantovani et al., "Tumor-Associated Macrophages as a Paradigm of Macrophage Plasticity, Diversity, and Polarization," Arterioscler. Thromb. Vasc. Biol., pp. 1478-1483, Jul. 2013.
Matei et al., "ATM-dependent DNA damage surveillance in T-cell development and leukemogenesis: the DSB connection," Immunological Reviews, vol. 209, pp. 142-158, 2006.
Merrick et al., "Immunosuppressive effects of radiation on human dendritic cells: reduced IL-12 production on activation and impairment of naive T-Cell priming," British Journal of Cancer, vol. 92, pp. 1450-1458, Apr. 2005.
Mosser et al., "Exploring the full spectrum of macrophage activation," Nat. Rev. Immunol., vol. 8, No. 12, pp. 958-969, Dec. 2008.
Murray et al., "Macrophage activation and polarization: nomenclature and experimental guidelines," Immunity, vol. 41, No. 1, pp. 14-20, Jul. 2014.
Park et al., "The Effect of Radiation on the Immune Response to Cancers," Int. J. Mol. Sci., vol. 15, pp. 927-943, Jan. 2014.
Paull, "Mechanisms of ATM Activation," Annu. Rev. Biochem., vol. 84, pp. 711-738, Jan. 2015.
Pereira-Lopes et al., "NBS1 is required for macrophage homeostasis and functional activity in mice," Blood, vol. 126, No. 22, pp. 2502-2510, Nov. 2015.
Prakash et al., "Low doses of gamma irradiation potentially modifies immunosuppressive tumor microenvironment by retuning tumor-associated macrophages: lesson from insulinoma," Carcinogenesis, vol. 37, No. 3, pp. 301-313, Jan. 2016.
Price et al., "The cell cycle inhibitor Cdkn1a regulates Langerhans cell radiation resistance and promotes T regulatory cell generation upon exposure to ionizing irradiation," Nat. Immunol., vol. 16, No. 10, pp. 1060-1068, Oct. 2015.
Rodriguez-Zapata et al., Macrophage Oxygen Metbolites in Acute Brucellosis, Infection, vol. 25, No. 3, pp. 57-58, 1997.
Caillou et al., "Tumor-Associated Macrophages (TAMs) Form an Interconnected Cellular Supportive Network in Anaplastic Thyroid Carcinoma," PLOS One, vol. 6, Issue 7, p. e22567, Jul. 2011.
Chen et al., "Triptolide mitigates radiation-induced pulmonary fibrosis via inhibition of axix of alveolar macrophages-NOXes-ROS-myofibroblasts," Cancer Biology and Therapy, vol. 17, No. 4, pp. 381-389, Mar. 2016.
Gupta et al., "Upsides and Downsides of Reactive Oxygen Species for Cancer: The Roles of Reactive Oxygen Species in Tumorigenesis, Prevention, and Therapy," Antioxidants and Redox Signaling, vol. 16, No. 11, pp. 1295-1322, Jun. 2012.
International Search Report for application No. PCT/EP2017/073677 dated Dec. 11, 2017.
Ligtenberg et al., "Methylcholanthrene-Induced Sarcomas Develop Independently from NOX2-Derived ROS," PLOS One, vol. 10, No. 6, p. e0129786, Jun. 2015.
Lu et al., "Androgens induce oxidative stress and radiation resistance in prostate cancer cells through NADPH oxidase," Prostate Cancer and Prostatic Diseases, vol. 13, pp. 39-46, Mar. 2010.
Marullo et al., "Abstract 1784: NOX-mediated chronic oxidative stress is inherent in human papillomavirus positive head and neck cancer cells and is implicated in radiosensitivity," Cancer Researh, vol. 73, No. 8 Supplement, Aug. 2013.
Xu et al., "NADPH Oxidases Are Essential for Macrophage Differentiation," The Journal of Biological Chemistry, vol. 291, No. 38, pp. 20030-20041, Aug. 2016.
Zhang et al., "Inhibiting TGF Beta 1 has a protective effect on mouse bone marrow suppression following ionizing radiation exposure in vitro," Journal of Radiation Research, vol. 54, pp. 630-636, Jan. 2013.
Amanzada et al., "Identification of CD68+ neutrophil granulocytes in in vitro model of acute inflammation and inflammatory bowel disease," Int. J. Clin. Exp. Pathol., vol. 6, No. 4, pp. 561-570, Apr. 2013.
Liang et al., "The Complex Role of Neutrophils in Tumor Angiogenesis and Metastasis," Cancer Immunology Research, vol. 4, No. 2, pp. 83-91, Feb. 2016.
Swierczak et al., "Neutrophils: important contributors to tumor progression and metastasis," Cancer Metastasis Review, vol. 34, pp. 735-751, Sep. 2015.

\* cited by examiner

NOX2 AS A BIOMARKER OF RADIOTHERAPY EFFICIENCY IN CANCER PATIENTS

SUMMARY OF THE INVENTION

Although tumor-associated macrophages have been extensively studied in the control of response to radiotherapy, the molecular mechanisms involved in the ionizing radiation-mediated activation of macrophages remain elusive. Here the present inventors show that ionizing radiation induces the expression of interferon-regulatory factor 5 (IRF5) promoting thus macrophage activation toward a pro-inflammatory phenotype. They reveal that the activation of the Ataxia telangiectasia mutated (ATM) kinase is required for ionizing radiation-elicited macrophage activation, but also for macrophage reprogramming after treatments with γ-interferon, lipopolysaccharide or chemotherapeutic agent (such as cis-platin), underscoring the fact that the kinase ATM plays a central role during macrophage phenotypic switching toward a proinflammatory phenotype.

They further demonstrate that NADPH oxidase 2 (NOX2)-dependent ROS production is upstream to ATM activation and is essential during this process. They also report that hypoxic conditions and the inhibition of any component of this signaling pathway (NOX2, ROS and ATM) impairs pro-inflammatory activation of macrophages and predicts a poor tumor response to preoperative radiotherapy in locally advanced rectal cancer.

Altogether, these results identify a novel signaling pathway involved in macrophage activation that may enhance effectiveness of radiotherapy through the re-programming of tumor infiltrating macrophages.

BACKGROUND OF THE INVENTION

Radiotherapy is one of the cornerstones of cancer treatment. Approximately, half of all cancer patients are treated with radiotherapy alone or in combination with chemotherapy. Although ionizing radiation (IR) directly causes senescence and death of tumor cells through the generation of reactive oxygen species (ROS) and DNA damage [1], recent studies underscore the fact that IR can also modulate immune cell functions and favor consequently the development of anti-cancer immunity [2, 3]. IR can induce the exposure of "eat-me" signals (such as calreticulin and heat shock protein 70 (HSP70)) and the release of danger signals (such as ATP and high-mobility group box 1 protein (HMGB1)) by the irradiated dying tumor cells (also referred as immunogenic cell death) [4], thus contributing to specific T cell response by increasing the tumor antigen cross-presentation to dendritic cells [5] and/or modifying the immunosuppressive microenvironment of tumors [6, 7]. IR can also control tumor immune response through the direct modulation of innate immune cell functions. Treatment with IR can modulate Langerhans cell functions and induce the accumulation of regulatory T cells into tumors [8]. In addition, IR controls macrophage plasticity and programs tumor-associated macrophages (TAMs) toward pro-inflammatory phenotype that orchestrates specific tumor immune response [9]. However, microenvironment factors such as low oxygen tension (also known as tumor hypoxia) may affect this program and favor the pro-tumorigenic macrophage activation phenotype in response to IR that has been associated with tumor resistance [10]. Nevertheless, the molecular mechanisms underlying IR-induced macrophage activation remain elusive.

Tumor-associated macrophages (TAMs) represent a major cellular component of the tumor microenvironment [11]. These macrophages derive from blood monocytes which, after their recruitment into tumors by tumor-derived chemo-attractants (such as macrophage colony-stimulating factor (M-CSF)), differentiate and activate in response to different environmental signals. Distinct transcriptional programs can be induced to shape their functional phenotypes. Macrophages can be broadly classified as classically activated pro-inflammatory macrophages and alternatively activated pro-tumorigenic macrophages [12]. The transcription factor interferon regulatory factor 5 (IRF5) has been demonstrated to determine the pro-inflammatory macrophage phenotype [13-15] along with other transcription factors (such as signal transducer and activator of transcription 1 (STAT1) and Nuclear factor-κB (NF-κB)), whereas IRF4 [16], STAT6 [17], and Kruppel-like factor 4 (KLF4) [18] are key transcription factors required for the establishment of the pro-tumorigenic macrophage phenotype. Interferon gamma plus lipopolysaccharide (IFN-γ+LPS) or tumor necrosis factor α (TNF-α) alone are known to induce classical macrophage activation that is characterized by an increased secretion of pro-inflammatory cytokines and chemokines (such as interleukin (IL-1β, IL-6, and CXC chemokine ligand (CXCL)8), an augmented production of inducible nitric oxide synthase (iNOS) [19] and of reactive oxygen species (ROS) [12]. Conversely, glucocorticoids, IL-4/IL-13, IL-10 drive macrophages to alternative macrophage activation with a reduced production of pro-inflammatory cytokines but a higher level of anti-inflammatory IL-10, transforming growth factor beta (TGF-β), arginase, membrane scavenger and mannose receptors. Pro-inflammatory macrophages possess bactericidal and antitumoral activities while pro-tumorigenic macrophages are associated with immune regulatory, tissue repair and pro-tumoral activities, highlighting the diversity of macrophage functions. In response to tumor microenvironment signals (such as tumor hypoxia, tumor metabolites and tumor-derived lactate [20, 21]), TAMs mainly adopt a pro-tumorigenic phenotype that contributes to tumor progression by promoting tumor growth, invasiveness and metastasis, angiogenesis and by suppressing immune responses [22-24]. In addition, several studies have demonstrated that TAMs are also associated with treatment resistance and poor clinical outcomes in various cancer settings (such as glioma, lymphoma, melanoma, sarcomas, head and neck, breast and lung cancer [25-28]), making them attractive targets for the development of new anticancer strategies to treat cancer [29, 30]. As the reprogramming of TAMs represents an attractive strategy to improve anti-cancer treatments, a better understanding of the molecular basis of the IR-mediated macrophage activation was needed for the improvement of the efficacy of radiotherapy.

Aware of this need, the present inventors explored the molecular mechanisms involved in IR-induced macrophage reprogramming. They revealed that the subsequent activation of the Ataxia telangiectasia mutated (ATM) kinase controls the expression of the transcription factor IRF5, which is involved in the reprogramming of macrophages towards a proinflammatory phenotype. They found that IR like other classical activators of macrophages increased the expression of the NADPH oxidase 2 (NOX2) which acts upstream of the DNA damage response that is involved in the induction of IRF5 expression and in the pro-inflammatory macrophage activation. They demonstrated that the alteration of this signaling pathway (NOX2→ROS→ATMS1981*) is associated with poor tumor response to neo-adjuvant radiotherapy in locally advanced rectal cancers.

They therefore propose to restore sensitivity and/or responsiveness to anti-cancer treatments (e.g., radiotherapy) by stimulating the activities of the proteins involved in the NOX2/ATM pathway. They also propose to predict the efficiency of an anti-cancer treatment by analyzing in a patient the biomarkers involved in this pathway, in particular ATM and/or NOX2.

DESCRIPTION OF THE INVENTION

Phenotypic and functional plasticity are key features of immune cells (such as macrophages) [38]. Tumor-associated macrophages (TAMs) display a mixed functional phenotype with a majority of alternative features [39] that have been associated with tumor growth and resistance to anti-cancer therapies (such as radiotherapy). Although reprogramming TAMs represents a promising approach to enhance cancer therapies [40-44], molecular mechanisms underlying ionizing radiation-elicited macrophage activation have been poorly characterized.

The present inventors have shown that the in vitro treatment of macrophages with different doses of IR led to their activations toward a pro-inflammatory phenotype. These observations were also confirmed on xenograft tumor models and on human rectal cancer specimens obtained from patients that have been treated with chemoradiotherapy.

Consistent with other in vitro and in vivo studies [13, 15, 45, 46], these results also revealed that the transcription factor IRF5, which is the major regulator of pro-inflammatory macrophage phenotype [15] is activated after IR (as revealed by the up-regulated expressions of IRF5 and IRF5-dependent target genes (such as IL-6, TNF-α or IFN-γ)). The transcription factor IRF5 which has been involved in the expression of pro-inflammatory cytokine genes and in the repression of antiinflammatory cytokine genes (such as IL-10) [15, 47], plays also a central role in hematopoietic cell development [48] and in the susceptibility to inflammatory autoimmune diseases (such as systematic lupus erythematosus, rheumatoid arthritis and multiple sclerosis) [49-51], demonstrating that the expression of IRF5 is tightly regulated during macrophage homoeostasis.

Considering that IR mainly acts through the induction of DNA damages and the production of reactive oxygen species (ROS) [52, 53], the inventors then investigated the role these DNA damage response and ROS production during this process. They report that the DNA damage/repair kinase ATM is activated by IR and by classical macrophage activators (such as LPS and IFN-γ) and that DNA damage/repair ATM kinase is required for macrophage activation. Despite the fact that the ATM kinase may contribute to the development of T cells [54] and of professional antigen-presenting cells (such as macrophage and denditric cells) [55,56] and modulate functions of immune cells (such as STING-dependent macrophage production of type I IFNs [57]), the contribution of ATM to macrophage activation was never investigated. Here, the inventors have found that IR induced the phosphorylations of ATM (on serine 1981) and of the histone H2AX (on serine 139) in a time- and dosedependent manner in macrophages, indicating that DNA double strand breaks and DNA damage response are elicited during macrophage activation. Moreover, the results presented below also demonstrated that ATM inhibition (either by a specific ATM inhibitor or by genetic depletion) impairs IRF5 up-regulation induced by IR and IFN-γ stimulation, highlighting that the biological activity of the kinase ATM controls macrophage activation. Despite several molecular components of DNA damage response pathways (such as Nijmegen breakage syndrome 1 (NBS1) protein [58]) have already been involved in monocyte/macrophage development and functions, the cellular events and signaling pathways that lead to ATM activation and control IRF5 expression during macrophage activation remain to be addressed.

In this study, the inventors also identify the NADPH oxidase 2 (NOX2)-dependent ROS production as an upstream second messenger required for ATM phosphorylation and macrophage activation. They found that the expression of NOX2 was increased after IR or IFN-γ treatment. The NOX2 expression might be regulated at transcriptional level (through the activation of PU.1 or NF-κB transcription factors [35]) or at posttranscriptional level [35]. Increased expression of NOX2 then led to the generation of ROS that contributes to double-strand breaks formation, induces the activation of ATM and IRF5, and favors the functional switch of macrophages from anti-inflammatory to pro-inflammatory phenotype (see FIG. 7).

Importantly, higher frequencies of TAMs showing an up-regulation of NOX2 expression (NOX2$^+$CD68$^+$) were observed in biopsies obtained from "good responders", as compared to those obtained from "bad responders" (see FIGS. 6F and 6G). This result suggests for the first time that the detection of NOX2 expression on TAMs may serve as a predictive factor for radiotherapy effectiveness.

The present study demonstrates that the histological detection of any components of the molecular cascade described hereafter in macrophages (NOX2→ROS→ATMS1981*→IRF5) predicted the effectiveness of radiotherapy and may also help for the prediction of other anticancer treatments.

In other words, they show for the first time that NOX2, ATM or IRF5 expression on TAMs can be used as a prognostic marker associated with longer overall survival for patients suffering from cancer, notably those that have been (or will be) treated with radiotherapy.

In a first aspect, the present invention relates on a method for in vitro predicting the benefit of the response of a subject diagnosed with cancer to an anti-cancer treatment such as radiotherapy, comprising the steps of:
a) obtaining a biological sample from said subject,
b) determining the NOX2 expression level in said biological sample; and
c) optionally, comparing said NOX2 expression level to the NOX2 expression level of a reference control or population.

In particular, if the NOX2 expression level assessed in step c) for said patient is higher than the reference expression level, then an overall long survival and/or a disease free survival benefit can be predicted. This long survival rate is associated with a low Tumor Regression Grade (typically inferior to 2, according to the Mandard classification). In certain condition, complete or subtotal tumour regression can be predicted.

In a second aspect, the present invention relates on a method for in vitro assessing whether an anti-cancer treatment such as radiotherapy is appropriate for a subject diagnosed with cancer, comprising the steps of:
a) obtaining a biological sample from said subject,
b) determining the NOX2 expression level in said biological sample; and
c) optionally, comparing said NOX2 expression level to the NOX2 expression level of a reference control or population.

In particular, an anti-cancer treatment such as radiotherapy will be determined as an appropriate treatment for said patient if the NOX2 expression level for said patient is higher than the NOX2 expression level for said reference control or population.

Conversely, an anti-cancer treatment such as radiotherapy will be determined as not being appropriate for said patient if the NOX2 expression level for said patient is lower than or equal to the NOX2 expression level for said reference control or population.

In a third aspect, the present invention relates on an in vitro screening method for selecting a subject suffering from cancer for an anti-cancer treatment such as radiotherapy, comprising the steps of:
a) obtaining a biological sample from said subject,
b) determining the NOX2 expression level in said biological sample; and
c) optionally, comparing said NOX2 expression level to the NOX2 expression level of a reference control or population. wherein said subject will be selected for an anti-cancer treatment such as radiotherapy if the NOX2 expression level for said patient is higher than the NOX2 expression level for said reference control or population.

In these three aspects, the NOX2 expression level can be replaced by the ATM or IRF5 expression level.

As used herein, the expression "biological sample" refers to any sample containing genomic DNA or mRNA from a subject. Said DNA may be contained in a solid tissue, in fluids and/or excretions of said subject. Said fluid is for example blood, serum, plasma, or urine. In a preferred embodiment, said biological sample is a blood sample of said subject, bone marrow or spleen or skin biopsies, or any other cells. Indeed, such a blood sample may be obtained by a completely harmless blood collection from the subject and thus allows for a non-invasive diagnosis. The blood sample used in the method of the invention is preferably depleted of most, if not all erythrocytes, by common red blood cell lysis procedures. The detection is performed on $CD68^+$ macrophages.

Macrophages containing samples can be obtained by any convenient means, for example from monocytes containing samples (see example 1.1. below).

Thus, in a more preferred embodiment, the first step of the method of the invention comprises the detection and the measurement of the macrophages present in said biological sample, by conventional markers such as CD11b or CD71.

In an even more preferred embodiment, the method of the invention also comprises the detection and the measurement of the CD68 marker at the cell surface of the macrophages present in the biological sample.

The sequence of the cluster of differentiation CD68 is well-known. The CD68 molecules are glycoproteins that bind to low density lipoproteins. Expression of cell surface CD68 on macrophages may be assessed using specific antibodies, in particular using well known technologies such as cell membrane staining using biotinylation (or other equivalent techniques), followed by immunoprecipitation with specific antibodies, flow cytometry, western blot, ELISA or ELISPOT, antibodies microarrays, or tissue microarrays coupled to immunohistochemistry. Preferably, the expression of cell surface CD68 is detected by flow cytometry. Flow cytometry is a useful tool for simultaneously measuring multiple physical properties of individual particles (such as cells). Cells pass single-file through a laser beam. As each cell passes through the laser beam, the cytometer records how the cell or particle scatters incident laser light and emits fluorescence. Using a flow cytometric analysis protocol, one can perform a simultaneous analysis of surface molecules at the single-cell level. The existence of markers which are specific for each of the contaminant cell types enables the identification of these cells in the blood sample of the subject. Identified contaminant cells can then be removed from the sample (i.e., physically) or from the analysis (i.e., by retaining only the data pertaining to the macrophage population for the analysis), so that the study then only focuses on the macrophage population. In this respect, although any of the above-mentioned analytical techniques can be used to identify the said contaminant white blood cells, flow cytometry is particularly adapted for this task, since it enables the skilled person to eliminate the contaminants and analyze the macrophage population with minimal effort.

Preferably, said biological sample comprises more than 70%, preferably more than 90%, more preferably more than $CD68^+$ macrophages.

As used herein, the term "subject" refers to any mammal, preferably a human, suffering from cancer. Yet, the method of the invention is particularly useful for testing a subject suffering from specific cancer, such as a glioma, a lymphoma, a melanoma, a sarcoma, a head and neck tumor, a breast or a lung cancer.

As used herein, a "reference control" corresponds preferably to a control sample comprising cells from "bad responder" patients (which is the reference population as used herein). Bad responders can be characterized by a Tumor Regression Grade superior to 3 (according to Mandard classification as set in [63]). More preferably, said control sample corresponds to $CD68^+$ macrophages of said patients. The "control" level of expression of NOX2 therefore corresponds to the average expression of NOX2 in samples collected from "bad responder" patients. Correspondingly, the "control" level of expression of ATM corresponds to the average expression of ATM in samples collected from "bad responder" patients. Finally, the "control" level of expression of IRF5 corresponds to the average expression of IRF5 in samples collected from "bad responder" patients. The expression level of these proteins can be assessed by classical means, as exposed below.

As used herein, the term "anti-cancer treatment" designates any treatment commonly used to treat a patient suffering from cancer. It can be for example a treatment with y-interferon, lipopolysaccharide, a radiotherapy or a chemotherapeutic agent (such as Cis-platin).

As used herein, the term "radiotherapy" or "radiotherapy-based treatment" means a therapy using ionizing radiations. This treatment works by damaging the DNA of cancerous cells. This DNA damage is caused by one of two types of energy, photon or charged particle. This damage is either direct or indirect ionization of the atoms which make up the DNA chain. Indirect ionization happens as a result of the ionization of water, forming free radicals, notably hydroxyl radicals, which then damage the DNA. The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy.

As used herein, "NOX2" designates the NADPH oxidase 2 (also known as Cytochrome b-245 heavy chain or cytochrome b(558) subunit beta) which, in humans, is encoded by the CYBB gene. This protein is a super-oxide generating enzyme which forms reactive oxygen species (ROS). The sequence of its mRNA is well-known (NM_000397 as shown in SEQ ID NO:12), as well as the sequence of its protein (NP_000388.2 as shown in SEQ ID NO:13).

In the methods of the invention, the NOX2/ATM/IRF5 expression level can be determined by any means conventionally used by the skilled person, such as PCR, RT-PCR, Northern blot, Western blot, immunohistochemistry, enzyme immunoassay (EIA), radioimmunoassay (RIA), enzyme linked immunoabsorbant assay (ELISA), etc.

In a preferred embodiment, a flow cytometry analysis is performed on the CD68$^+$ macrophages isolated from the tested patient (as described above), and the number of NOX2$^+$CD68$^+$ macrophages is assessed as performed by the inventors in the examples below.

It is known in the art that morphological changes of blood cells begin after 30 minutes of drawing. Such changes consist in granulocyte swelling, increases of band forms, and or loss of specific granulation sometimes associated with vacuolization, especially in eosinophils and monocytes. It will be clear to the skilled person that the results of the method may be affected by the nature and the extent of the changes taking place. It is therefore preferable that the blood sample used in the method of the invention be fresh. By "a fresh blood sample", it is herein referred to a sample of blood which has been drawn within the previous 48 h, 24 h or 5 hours, preferably 4 hours, 3 hours, 2 hours, 1 hour, 30 minutes, or 15 minutes. Preferentially, the fresh blood sample of the invention will be kept at 4° C. until used.

NOX2$^+$CD68$^+$ macrophages can be detected by using NOX2 antibodies (such as anti-pg91-phox 54.1) and conventional CD68 antibodies, preferably by flow cytometry, as explained in the examples below.

The present invention is also drawn to the use of a kit or array containing a reagent for assaying NOX2 expression, notably for in vitro predicting the benefit of the response of a subject diagnosed with cancer to an anti-cancer treatment such as radiotherapy or for in vitro predicting the benefit of the response of a subject diagnosed with cancer to an anti-cancer treatment such as radiotherapy, or for in vitro selecting a subject suffering from cancer for an anti-cancer treatment such as radiotherapy, in the conditions discussed above.

In a preferred embodiment, this kit contains:
a) a probe and/or or a pair of primers that specifically hybridizes to the NOX2 mRNA or cDNA, or to the complementary sequence thereof; or
b) an anti-NOX2 antibody, optionally labeled, capable of specifically recognizing the NOX2 protein.

In other words, the invention pertains to the use of primers or probes that can specifically amplify or hybridize the genomic region of NOX2, or fragments thereof, or of antibodies which recognize specifically the NOX2 protein (NP_000388.2), for in vitro predicting the benefit of the response of a subject diagnosed with cancer to an anti-cancer treatment such as radiotherapy or for in vitro predicting the benefit of the response of a subject diagnosed with cancer to an anti-cancer treatment such as radiotherapy, or selecting a subject suffering from cancer for an anti-cancer treatment such as radiotherapy.

As used herein, "primers" designate isolated nucleic acid molecules that can specifically hybridize or anneal to 5' or 3' regions of a target genomic region (plus and minus strands, respectively, or vice-versa). In general, they are from about 10 to 30 nucleotides in length and anneal at both extremities of a region containing about 50 to 200 nucleotides in length. Under appropriate conditions and with appropriate reagents, such primers permit the amplification of a nucleic acid molecule comprising the nucleotide sequence flanked by the primers. As they have to be used by pairs, they are often referred to as "primers pair" or "primers set".

As used herein, "probes" are molecules that are capable of specifically hybridizing a genomic region of interest (e.g., of NOX2mRNA: NM_000397). They are useful to highlight the presence of said genomic region in biological samples. These probes may comprise at least one non-natural nucleotide, e.g., a peptide nucleic acid (PNA), a peptide nucleic acid having a phosphate group (PHONA), a bridged nucleic acid or locked nucleic acid (BNA or LNA), and a morpholino nucleic acid. Non-natural nucleotides also include chemically modified nucleic acids or nucleic acid analogs such as methylphosphonate-type DNA or RNA, phosphorothioate-type DNA or RNA, phosphoramidate-type DNA or RNA, and 2'-O-methyl-type DNA or RNA.

Such analysis can be performed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin), or an antibody fragment (e.g., a single-chain antibody, an isolated antibody hypervariable domain, etc.) which recognize specifically the NOX2 protein of NP_000388.2.

Of note, the inventors demonstrate that the ATM protein, and more specifically the phosphorylated protein form ATMS1981*, may be used alone, or in combination with the NOX2 marker, to predict the efficiency of an anti-cancer treatment, in particular a radiotherapy treatment.

As used herein, "ATM" designates the ataxia telangiectasia mutated protein, which is a serine/threonine protein kinase that is recruited and activated by DNA double-strand breaks. The sequence of its mRNA is well-known (NM_00051 as shown in SEQ ID NO:15), as well as the sequence of its protein (NP_00042 as shown in SEQ ID NO:14).

Thus, the present invention also relates on a method for in vitro predicting the benefit of the response of a subject diagnosed with cancer to an anti-cancer treatment such as radiotherapy, comprising the steps of:
a) obtaining a biological sample from said subject,
b) determining the ATM expression level in said biological sample; and
c) optionally, comparing said ATM expression level to the ATM expression level of a reference control or population.

In particular, if the ATM expression level assessed in step c) for said patient is higher than the reference expression level, then an overall long survival and/or a disease free survival benefit can be predicted. This long survival rate is associated with a low Tumor Regression Grade (typically inferior to 2 according to the Mandard classification as disclosed in [63]). In certain condition, complete or subtotal tumour regression can be predicted.

Moreover, the present invention relates on a method for in vitro assessing whether an anti-cancer treatment such as radiotherapy is appropriate for a subject diagnosed with cancer, comprising the steps of:
a) obtaining a biological sample from said subject,
b) determining the ATM expression level in said biological sample; and
c) optionally, comparing said ATM expression level to the ATM expression level of a reference control or population.

In particular, an anti-cancer treatment such as radiotherapy will be determined as an appropriate treatment for said patient if the ATM expression level for said patient is higher than the ATM expression level for said reference control or population.

The present invention finally relates on an in vitro screening method for selecting a subject suffering from cancer for an anti-cancer treatment such as radiotherapy, comprising the steps of:
a) obtaining a biological sample from said subject,
b) determining the ATM expression level in said biological sample; and
c) optionally, comparing said ATM expression level to the ATM expression level of a reference control or population.
wherein said subject will be selected for an anti-cancer treatment such as radiotherapy if the ATM expression level for said patient is higher than the ATM expression level for said reference control or population.

In all these methods, the ATM protein is preferably the phosphorylated protein form ATMS1981*. More preferably, this protein is combined with NOX2.

Moreover, the inventors demonstrate that the expression level of the IRF5 transcription factor may be used alone, or in combination with the NOX2 marker and/or the ATM marker, to predict the efficiency of an anti-cancer treatment, in particular a radiotherapy treatment.

As used herein, "IRF5" designates the interferon regulatory factor which acts as a molecular switch that controls whether macrophages will promote or inhibit inflammation. The sequence of its mRNA is well-known (NM_001098627 for isoform b is shown in SEQ ID NO:16; NM_001098629 for isoform d is shown in SEQ ID NO:17), as well as the sequence of its protein (NP_001092097 for isoform b as shown in SEQ ID NO:18; NP_001092099 for isoform d as shown in SEQ ID NO:19).

It is also encompassed a method for in vitro predicting the benefit of the response of a subject diagnosed with cancer to an anti-cancer treatment such as radiotherapy, comprising the steps of:
a) obtaining a biological sample from said subject,
b) determining the expression level in said biological sample; and
c) optionally, comparing said IRF5 expression level to the IRF5 expression level of a reference control or population.

In particular, if the IRF5 expression level assessed in step c) for said patient is higher than the reference expression level, then an overall long survival and/or a disease free survival benefit can be predicted. This long survival rate is associated with a low Tumor Regression Grade (typically inferior to 2 according to the Mandard classification as disclosed in [63]). In certain condition, complete or subtotal tumour regression can be predicted.

Moreover, the present invention discloses a method for in vitro assessing whether an anti-cancer treatment such as radiotherapy is appropriate for a subject diagnosed with cancer, comprising the steps of:
a) obtaining a biological sample from said subject,
b) determining the IRF5 expression level in said biological sample; and
c) optionally, comparing said IRF5 expression level to the IRF5 expression level of a reference control or population.

In particular, an anti-cancer treatment such as radiotherapy will be determined as an appropriate treatment for said patient if the IRF5 expression level for said patient is higher than the IRF5 expression level for said reference control or population.

The present invention also discloses an in vitro screening method for selecting a subject suffering from cancer for an anti-cancer treatment such as radiotherapy, comprising the steps of:
a) obtaining a biological sample from said subject,
b) determining the IRF5 expression level in said biological sample; and
c) optionally, comparing said IRF5 expression level to the IRF5 expression level of a reference control or population.
wherein said subject will be selected for an anti-cancer treatment such as radiotherapy if the IRF5 expression level for said patient is higher than the IRF5 expression level for said reference control or population.

In a preferred embodiment, both the ATM and IRF5 expression levels are combined in the above-methods. In another preferred embodiment, both the NOX2 and IRF5 expression levels are combined in the above-methods.

In a preferred embodiment, the expression levels of all the three proteins (NOX2, ATM and IRF5) is assessed in the above-methods.

Eventually, it has been clearly demonstrated that macrophage activation toward NOX2/ATM dependent pro-inflammatory phenotype was involved in tumor response to chemo-radiotherapy (with no impact on the overall survival and disease free survival of patients).

The present Inventors therefore propose to modulate the components of the NOX2/ATM pathway in order to impact the reprogramming of macrophages elicited by IR or IFN-γ.

This modulation can be an ex vivo activation of the CD68⁺ macrophages that have been extracted from the blood of the patient, and, can be administered to the same patient after their activation. Said activation may be performed by ionizing ex vivo the macrophages of said patients, as disclosed in the examples below (example 2.1.).

Alternatively, this modulation can be performed by stimulating the activity of the NOX2 protein, or of the ATM protein, or of the IRF5 transcription factor. As disclosed in the examples below, stimulating this specific pathway could constitute effective strategies to enhance radiotherapy efficacy in clinic.

Stimulating compounds are for example chosen in the group consisting of:
NOX2 activators such as small molecules that activate ROS production, quinolinone derivatives, or NOX agonists with anti-inflammatory properties that are able to decrease the pro-inflammatory role of TNF-α in the low nanomolar range [60].
ATM activators such as kinases dependent or independent of the Mre11-Rad50-Nbs1 (MRN) complex, other factors at sites of DNA breaks, and components that can stimulate ATM autophosphorylation [61, 62].
IRF5 activators such as components that can induce the phosphorylation of IRF5.

Activation of this pathway can be done by any conventional means, at the transcriptional level, or by activating the activities of the enzyme directly.

The inventors propose that combining radiotherapy with other modalities of cancer treatments (such as PARP inhibitors) might enhance the tumor response to radiotherapy and lead to a long-term benefit to rectal patients.

As used herein, the terms "in vitro" and "ex vivo" are equivalent and refer to studies or experiments that are conducted using biological components (e.g., cells or population of cells) that have been isolated from their usual host organisms (e.g., animals or humans). Such isolated cells can be further purified, cultured or directly analyzed to assess the presence of the target markers. These experiments can be for example reduced to practice in laboratory materials such as tubes, flasks, wells, eppendorfs, etc. In contrast, the term "in vivo" refers to studies that are conducted on whole living organisms.

As used herein, the term "kit" refers to any system for delivering materials. In the context of reaction assays, it includes systems that allow the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials.

FIGURE LEGENDS

FIG. 1. Irradiation activates macrophages toward pro-inflammatory phenotype.

(A) Colorectal HCT116 cells were injected subcutaneously (4 $10^6$ cells/mouse) into immunodeficient mice and tumor growth was monitored. Results are expressed as mean value±SEM. P value ($^{\delta\delta}p<0.01$) was calculated by means of the paired-Student's t Test. (B-E) Representative confocal micrographs and frequencies of iNOS$^+$CD11b$^+$ (B, C) or γ-H2AX$^+$CD11 b$^+$ (D, E) tumor-associated macrophages detected in absence or after 20 Gy single dose irradiation are shown (scale bar, 20 μm). Representative iNOS$^+$CD11b$^+$ or H2AX$^+$CD11 b$^+$ macrophages are shown in inserts (scale bar, 5 μm). Results are expressed as mean value±SEM. P value (*$p<0.05$) was calculated using Mann-Whitney test (n=4). (F-H) Representative confocal micrographs and frequencies of phorbol-12-myristate-13-acetate (PMA)-treated human THP1 monocytes showing γ-H2AX$^+$ nuclear foci (F, G) or expressing iNOS (iNOS$^+$) (F, H), in control cells or 24 hours after 2 Gy irradiation are shown (scale bar, 20 μm). Representative γ-H2AX$^+$ nuclear foci or iNOS expressing macrophages are shown in inserts (scale bar, 5 μm). Results are expressed as mean value±SEM. P values (*$p<0.001$, **$p<0.0001$) were calculated using unpaired Student's t test (n=3). (I-K) IRF5 expression after respectively 96, 96 and 6 hours culture of (PMA)-treated human THP1 monocytes (I), hMDM (J) or murine RAW264.7 macrophages (K) that have been irradiated (or not) with indicated doses. Representative immunoblots are shown (n=3). GAPDH is used as loading control. (L, M) Detection of IL-1β and IL-8 release in the supernatants of hMDM (L) or murine RAW264.7 macrophages (M) that have been irradiated (or not) with indicated doses. Representative immunoblots are shown (n=3). (N, O) Detection of cytokine secretion in the supernatants of hMDMs that have been treated or not with 4Gy irradiation. Array images were captured following 1-10 minute exposures to peroxidase substrate (N). Relative levels of cytokines detected in the supernatants of irradiated macrophages as compared to those detected in non-irradiated macrophages are revealed as fold change of arbitrary units. Pro- and anti-inflammatory cytokines and chemokines are indicated (O). Data are obtained from three healthy representative donors.

Figure 2:
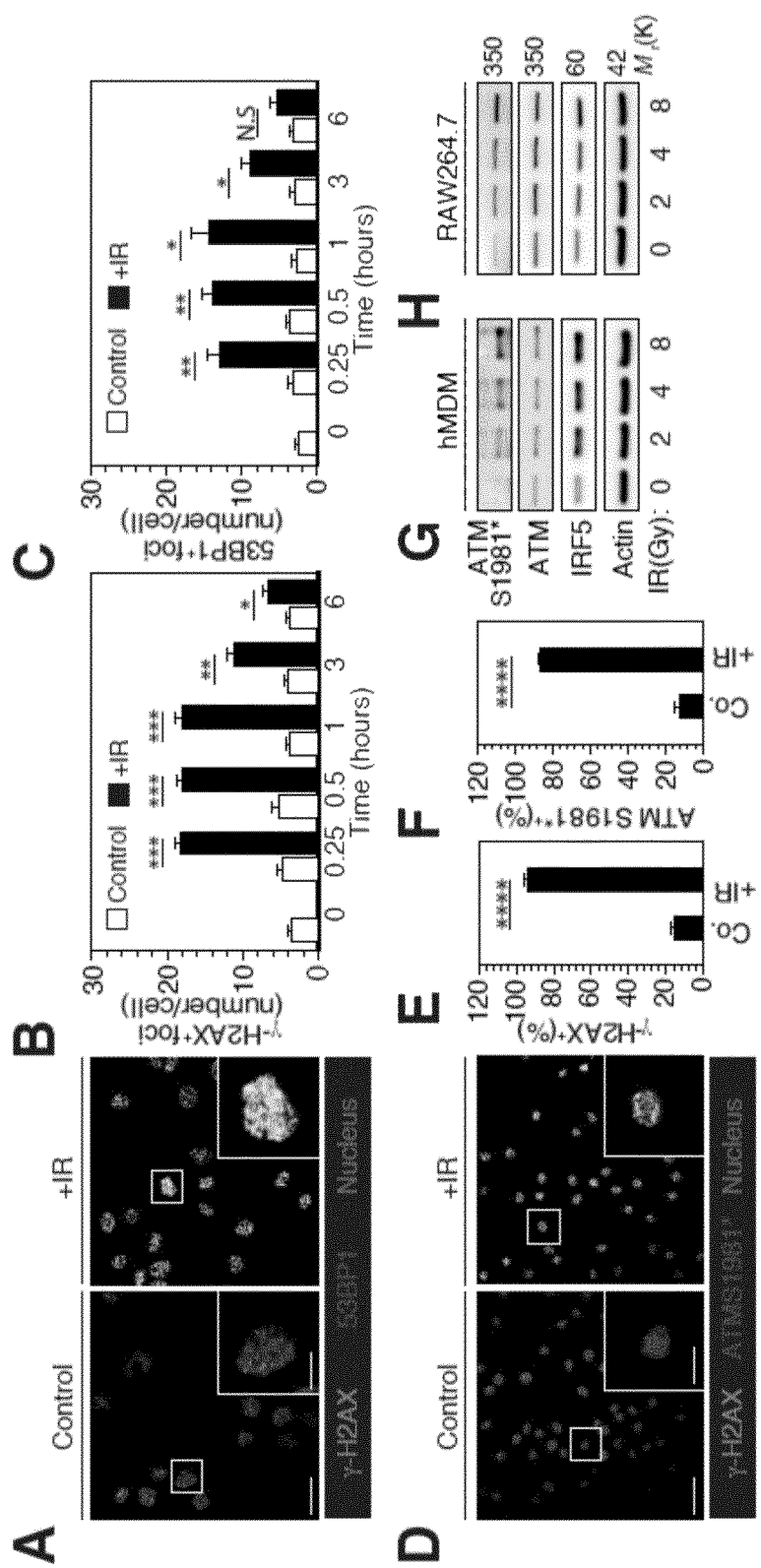
Figure 2:
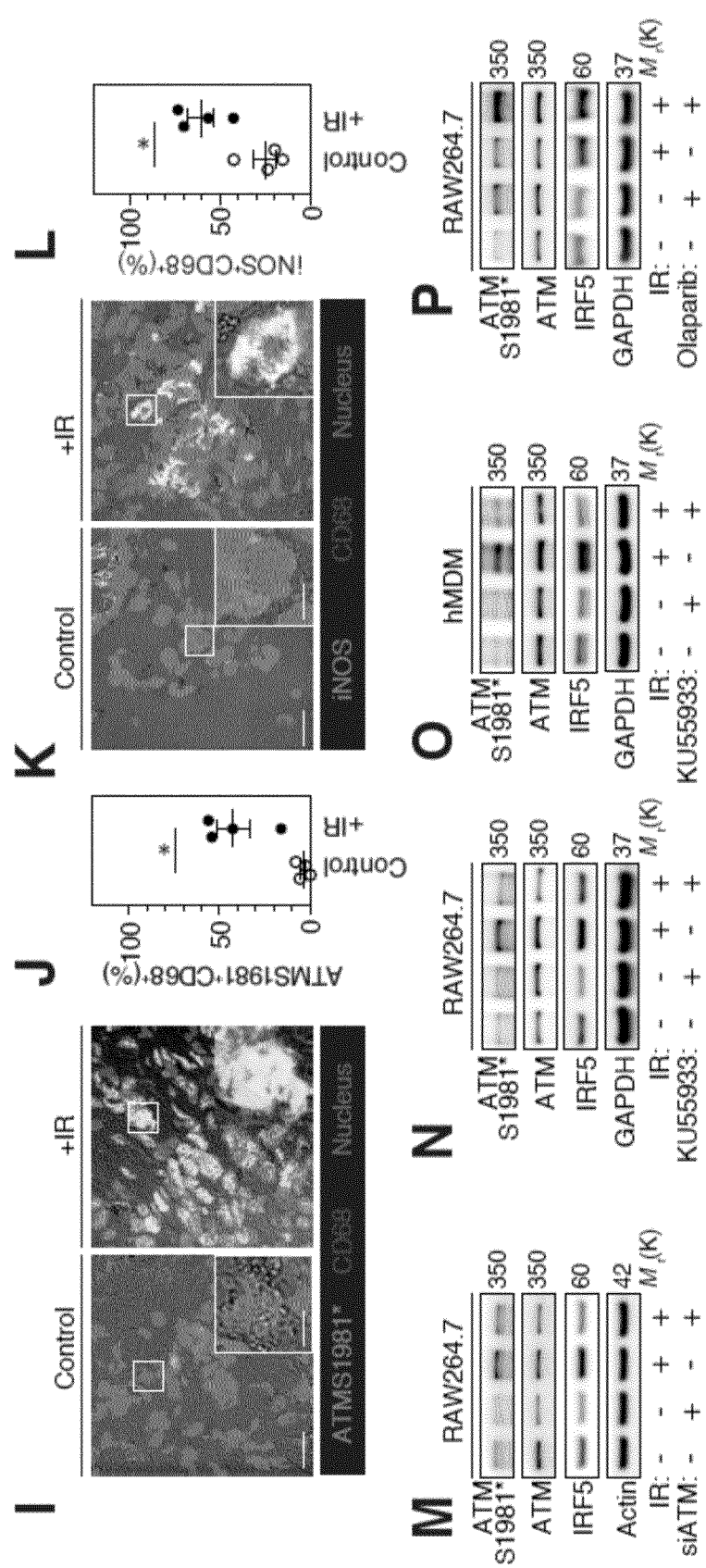

FIG. 2. ATM activation controls IR-induced pro-inflammatory macrophage phenotype.

(A) Representative confocal micrographs of phorbol-12-myristate-13-acetate (PMA)-treated human THP1 monocytes showing γ-H2AX$^+$ or 53BP$^+$ foci following 2Gy single dose irradiation are shown (scale bar, 20 μm). Scale bar of inserts is 5 μm. (B, C) Frequencies of PMA-treated human THP1 monocytes showing γ-H2AX$^+$ (B) or 53BP$^+$ (C) nuclear foci after 2 Gy single dose irradiation are shown at indicated times. (D-F) Representative confocal micrographs and frequencies of murine RAW264.7 macrophages showing γ-H2AX$^+$ nuclear foci (D, E) or AMTS1981* phosphorylation (ATMS1981*$^+$) (D, F), in control cells or 1 hour after 2 Gy single dose irradiation are shown (scale bar, 20 μm). Representative γ-H2AX$^+$ nuclear foci and ATMS1981*$^+$ macrophages are shown in inserts (scale bar, 5 μm). Results are expressed as mean value±SEM. P values (*$p<0.05$, $p<0.01$,*$p<0.001$, ****$p<0.0001$) were calculated using unpaired Student's t Test (n=3). (G, H) ATMS1981*, ATM and IRF5 expression after respectively 96 and 6 hours culture of hMDM (G) or murine RAW264.7 macrophages (H) that have been irradiated (or not) with indicated doses are determined. Representative immunoblots are shown (n=3). Actin is used as loading control. (I-L) Representative confocal micrographs and frequencies of ATMS1981*+CD68$^+$ (I, J) or iNOS$^+$CD68$^+$ (K, L) macrophages that have been detected in absence or after 45 Gy total dose of fractionated irradiation on biopsies obtained from locally advanced rectal cancer patients are shown (scale bar, 20 μm; scale bar of insert, 5 μm). Results are expressed as mean value±SEM. P value (*$p<0.05$) was calculated using Mann-Whitney test (n=4). (M, N) ATMS1981*, ATM and IRF5 expression after 6 hours culture of murine RAW264.7 macrophages (M, N) that have been depleted for ATM (M) or treated with 20 μM of KU55933 (N) and irradiated (or not) with 2 Gy are shown. Representative immunoblots are shown (n=3). GAPDH (or actin) is used as loading control. (O) ATMS1981*, ATM and IRF5 expression after 96 hours culture of hMDM that have been treated with 10 μM of KU55933 and irradiated (or not) with 4 Gy are shown (n=3). (P) ATMS1981*, ATM and IRF5 expression after 6 hour culture of murine RAW264.7 macrophages that have been treated with 10 μM of Olaparib and irradiated (or not) with 2 Gy are shown. Representative immunoblots are shown (n=3). GAPDH is used as loading control.

Figure 3:
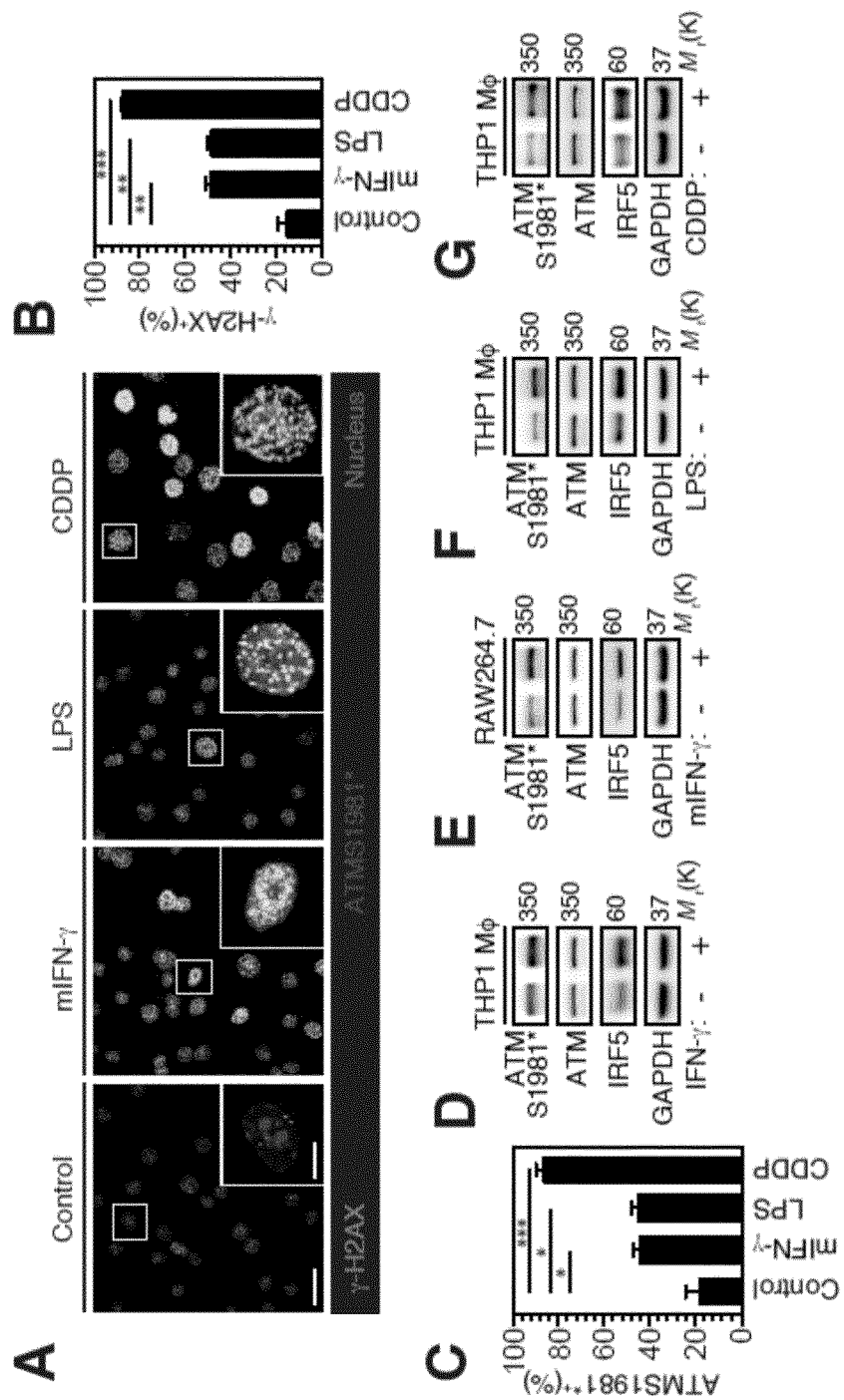
Figure 3:
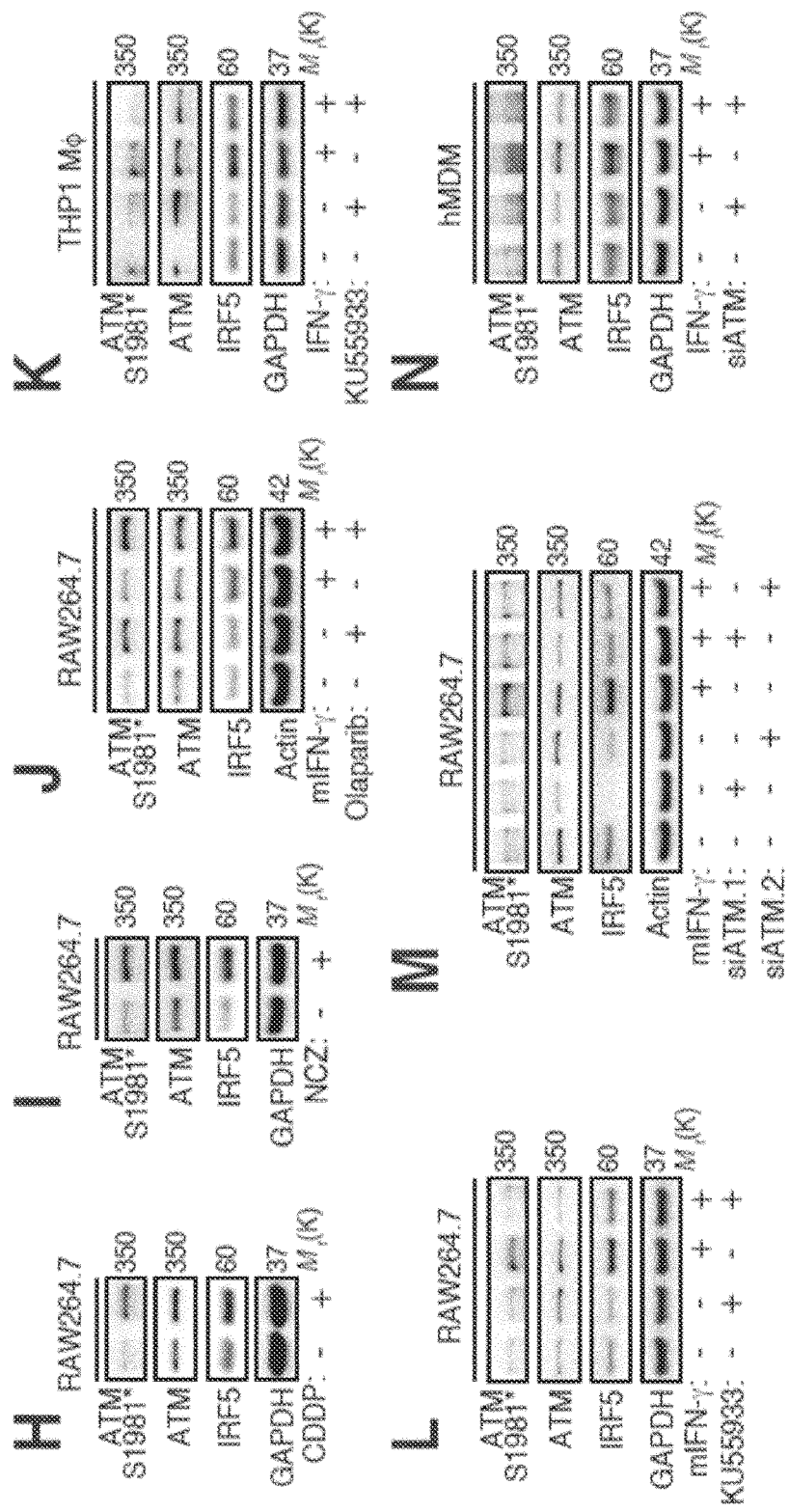

FIG. 3. Classical macrophage activation is dependent of ATM.

(A-C) Representative confocal micrographs and frequencies of murine RAW264.7 macrophages showing γ-H2AX$^+$ nuclear foci (A, B) or ATMS1981* phosphorylation (ATMS1981*+) (A, C) in control cells or after 24 h treatments with 20 ng/ml of recombinant murine IFN-γ (mIFN-γ), 100 ng/ml of lipopolysaccharide (LPS) or 10 μM of cisplatinium (CDDP) are shown (scale bar, 20 μm). Representative macrophages with ATMS1981*+ and γ-H2AX$^+$ nuclear foci are shown in inserts (scale bar, 5 μm). Results are expressed as mean value±SEM. P values (*$p<0.05$, $p<0.01$,*$p<0.001$) were calculated using unpaired Student's t Test (n=3). (D-1) ATMS1981*, ATM and IRF5 expressions after 24 hours culture of (PMA)-treated human THP1 monocytes (D, F, G) or murine RAW264.7 macrophages (E, H, 1) that have been treated (or not) with 20 ng/ml of recombinant human IFN-γ (IFN-γ) (D), 20 ng/ml of recombinant murine IFN-γ (m IFN-γ) (E), 100 ng/ml of lipopolysaccharide (LPS) (F), 10 μM of cisplatinium (CDDP) (G, H) or 200 ng/ml of neocarzinostatin (NCZ) (I) are determined. Representative immunoblots are shown (n=3). GAPDH is used as loading control. (J-N) ATMS1981*, ATM and IRF5 expressions after respectively 24 hours culture of murine RAW264.7 macrophages (J, L, M), (PMA)-treated human THP1 monocytes (K) or hMDMs (N) that have been incubated with 10 μM of Olaparib (J), with 20 μM of KU55933 (K, L) or depleted for ATM (M, N) and treated (or not) with 20 ng/ml mIFN-γ (for RAW264.7 macrophages) (J, L, M), 20 ng/ml human IFN-γ (for (PMA)-treated human THP1 monocytes)(K), or 4 μg/ml of human IFN-γ (for hMDM) (N) are evaluated. Representative immunoblots are shown (n=3). Actin (or GAPDH) is used as loading control.

Figure 4:
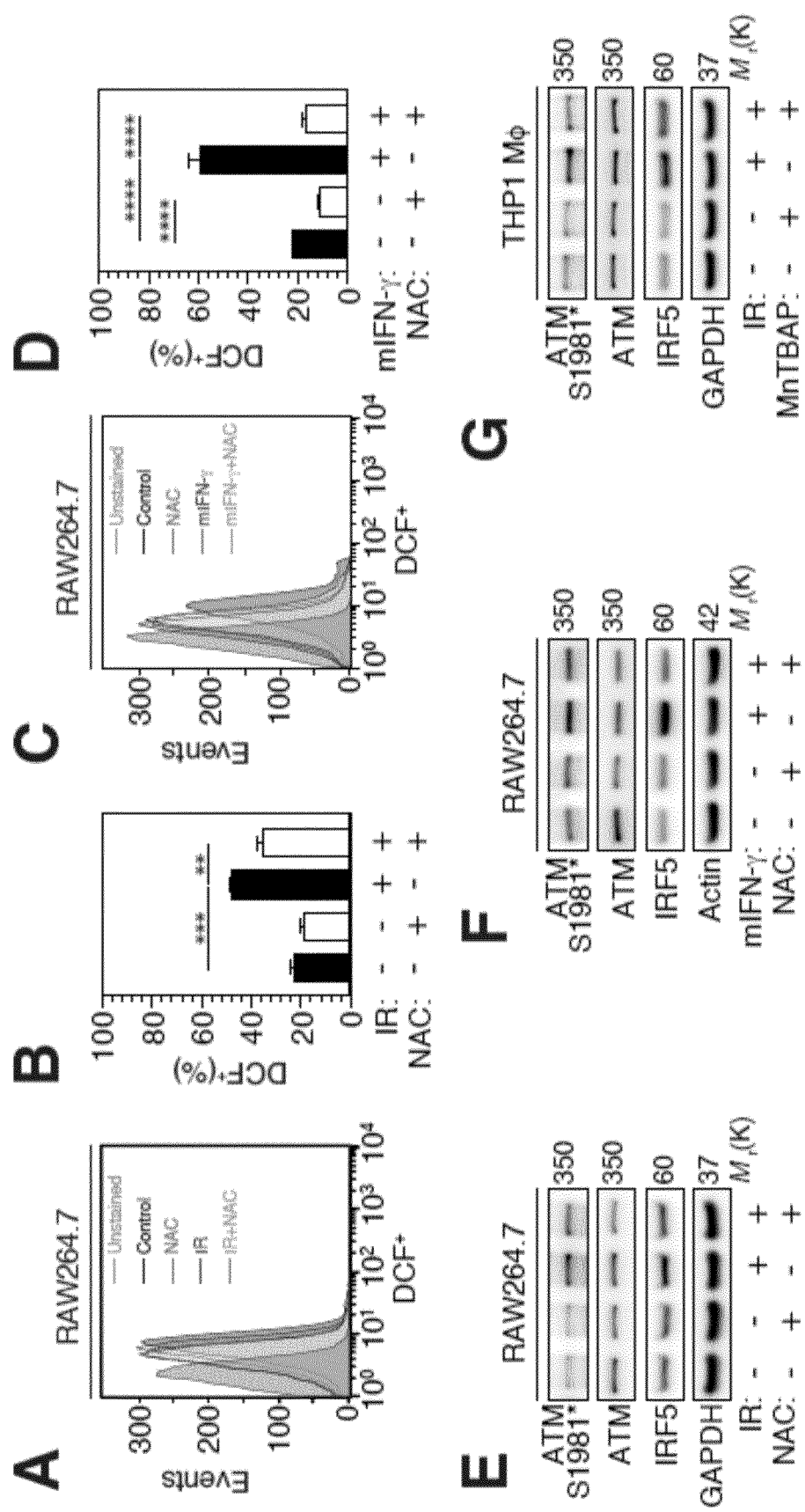
Figure 4:
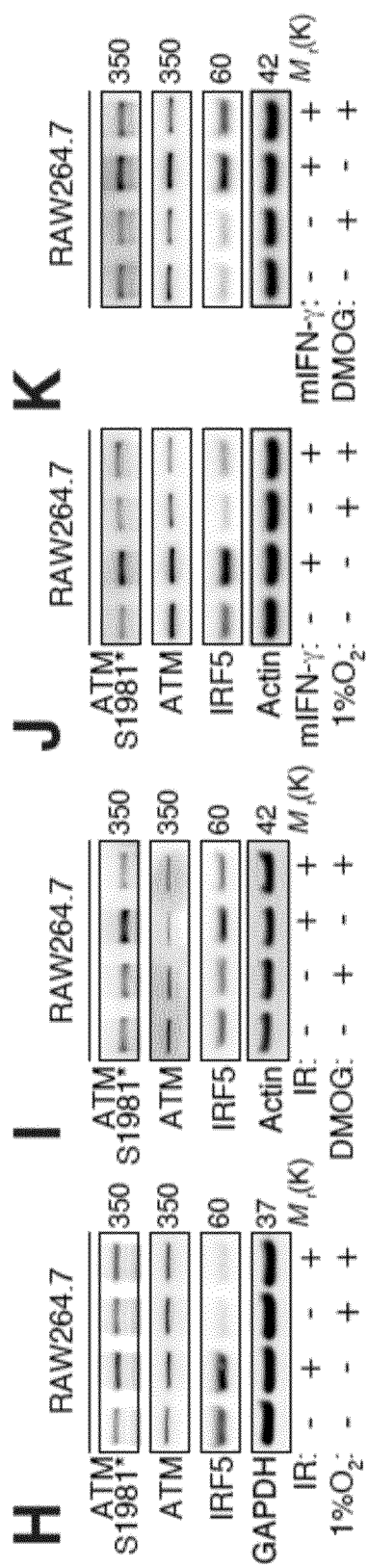

FIG. 4. Reactive oxygen species are involved in IR-induced pro-inflammatory macrophage activation.

(A-D) Murine RAW264.7 macrophages treated with 1 μg/ml of NAC were stimulated with 2 Gy single dose irradiation (A, B) or 20 ng/ml mIFN-γ (C, D), stained with H2DCFDA and analysed by flow cytometry. Representative flow cytometry analysis and quantifications are shown. Data are presented as means±SEM in B and D panels. Significances are  P≤0.01,* P≤0.001 and **** P≤0.0001 (n=3). (E-K) ATMS1981*, ATM and IRF5 expressions after respectively 6 and 24 hours culture of murine RAW264.7 macrophages (E, F, H-K) that have been incubated with 1 μg/ml of NAC (E, F), with cultured in 1% O2 (H, J) or 500 μM DMOG (I, K) and irradiated with 2 Gy single dose (E, H and I) or treated with 20 ng/ml mIFN-γ (F, J and K) were determined. Representative immunoblots are shown (n=3). GAPDH (or Actin) is used as loading control. (G) ATMS1981*, ATM and IRF5 expressions after 48 hours culture of phorbol-12-myristate-13-acetate (PMA)-treated human THP1 monocytes that have been incubated with 10 μM of MnTBAP and irradiated with 8Gy single dose were determined. Representative immunoblots are shown (n=3). GAPDH is used as loading control.

Figure 5:
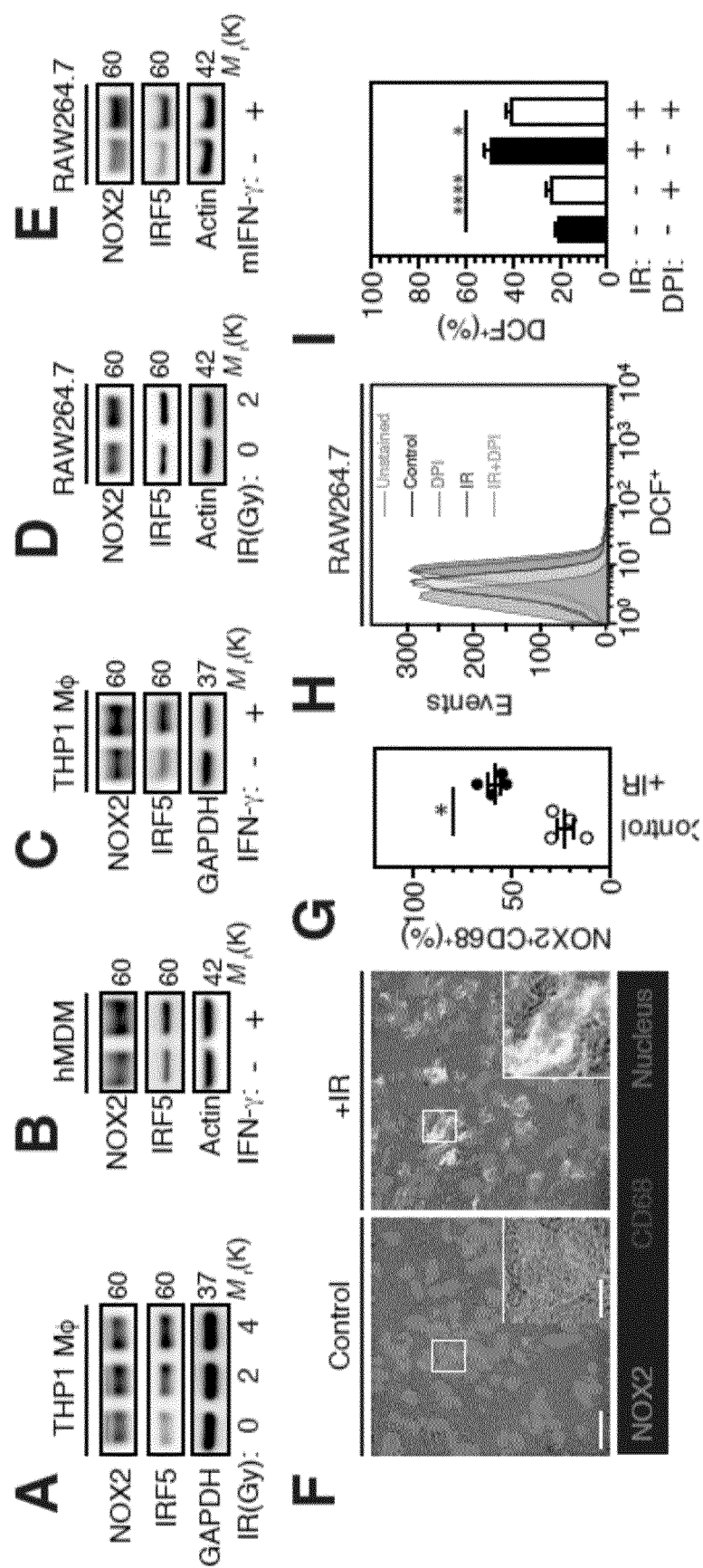
Figure 5:
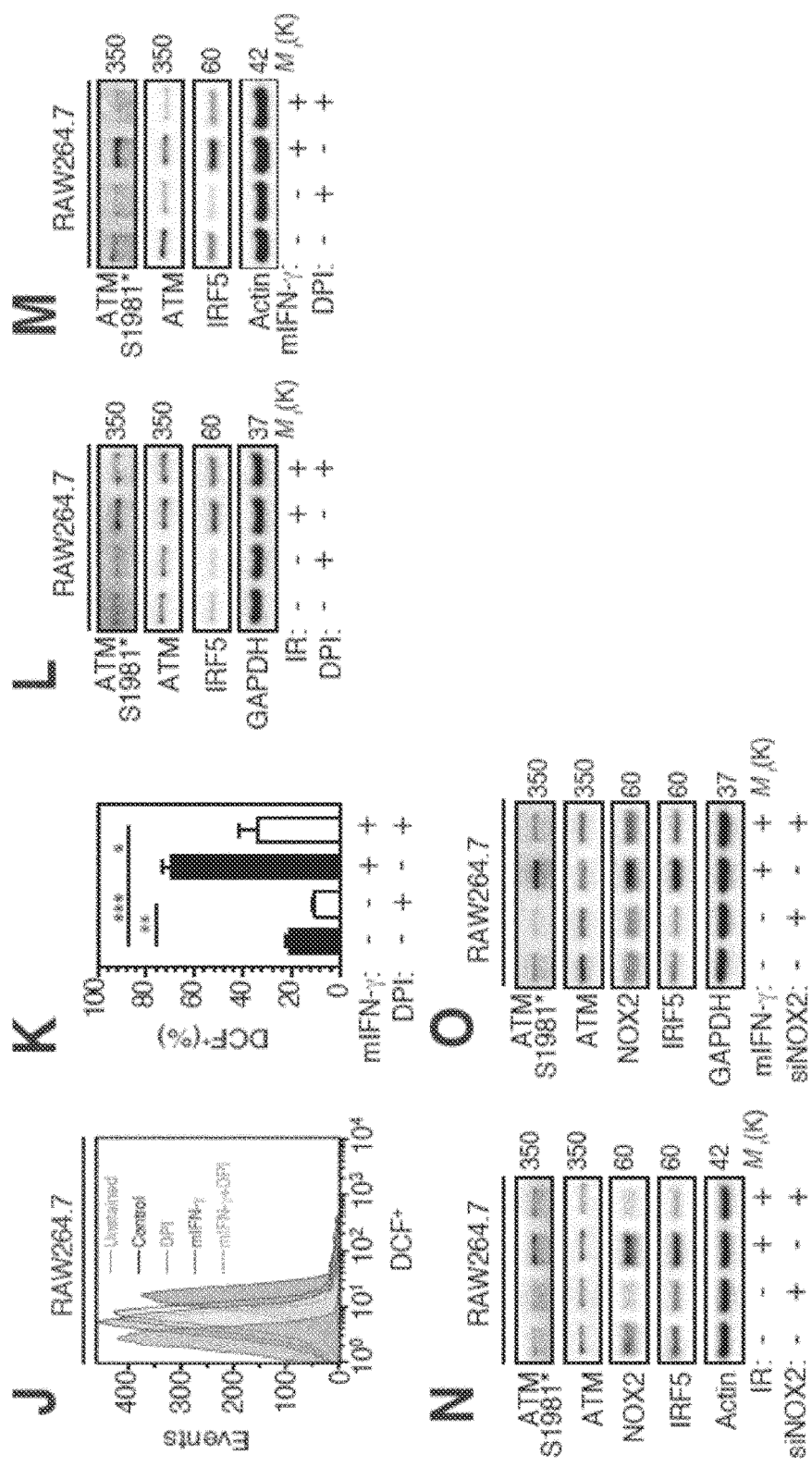

FIG. 5. NOX2-dependent ROS production is involved in the pro-inflammatory macrophage activation.

(A-E) NOX2 and IRF5 expressions after respectively 96 and 6 hours culture of (PMA)-treated human THP1 monocytes (A) or murine RAW264.7 macrophages (D) that have been irradiated (or not) with indicated doses (A and D); or 24 hours of culture of hMDM with 4 μg/ml of hIFN-γ (B), (PMA)-treated human THP1 monocytes with 20 ng/ml of hIFN-γ (C), or murine RAW264.7 macrophages with 20 ng/ml of mIFN-γ (E), were determined. Representative immunoblots are shown (n=3). GAPDH and actin were used as loading control. (F, G) Representative confocal micrographs and frequencies of NOX2$^+$CD68$^+$ tumor-associated macrophages detected in absence or after 45 Gy total dose of fractionated irradiation on biopsies obtained from locally advanced rectal cancer patients are shown (scale bar, 20 μm; scale bar of insert, 5 μm). Results are expressed as mean value±SEM. P value (*p<0.05) was calculated using Mann-Whitney test (n=4). (H-K) Murine RAW264.7 macrophages treated with 200 nM of DPI and irradiated with 2 Gy single dose (H, I) or stimulated with 20 ng/ml m IFN-γ (J, K), stained with H2DCFDA and analyzed by flow cytometry. Representative flow cytometry analysis and quantifications are shown. Data are presented as means±SEM in J and L panels. Significances are * P≤0.05,  P≤0.01, * P≤0.001 and **** P≤0.0001 (n=3). (L-O) ATMS1981*, ATM and IRF5 expressions after respectively 6 and 24 hours culture of murine RAW264.7 macrophages that have been incubated with 200 nM of DPI (L, M) or depleted for NOX2 (N, O) and irradiated with 2 Gy single dose (L, N) or treated with 20 ng/ml mIFN-γ (M, O) were determined. Representative immunoblots are shown (n=3). GAPDH or Actin was used as loading control.

Figure 6:
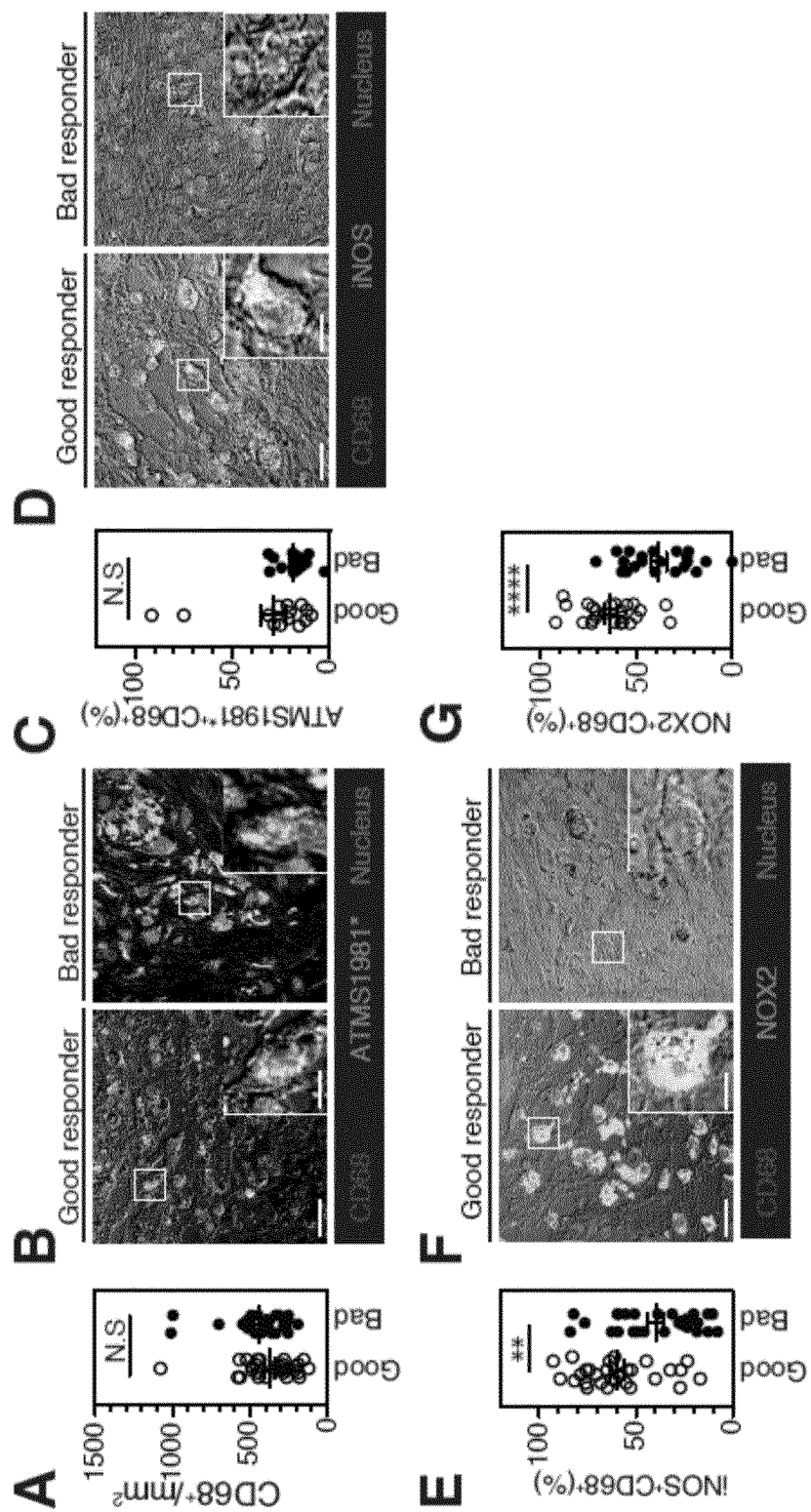

FIG. 6. The perturbation of NOX2/ATM-dependent signalling pathway is associated with poor tumor response to radiation therapy.

(A) Densities of CD68$^+$ tumour-infiltrating macrophages detected on biopsies of human rectal tumors from good responders (n=29) and bad responders (n=27) to neoadjuvant radiation therapy were analyzed. Data are presented as means±SEM. (B) Representative confocal micrographs and frequencies of ATMS1981*+CD68$^+$ (B, C), iNOS$^+$CD68$^+$ (D, E) or NOX2$^+$CD68$^+$ (F, G) tumor-associated macrophages detected in absence or after 45 Gy irradiation are shown (scale bar, 20 μm). Representative ATMS1981*+CD68$^+$, iNOS$^+$CD68$^+$ or NOX2$^+$CD68$^+$ macrophages are shown in inserts (scale bar, 5 μm). Results are expressed as mean value±SEM. P values ( P≤0.01 and * P≤0.001) were calculated using Mann-Whitney test.

Figure 7:
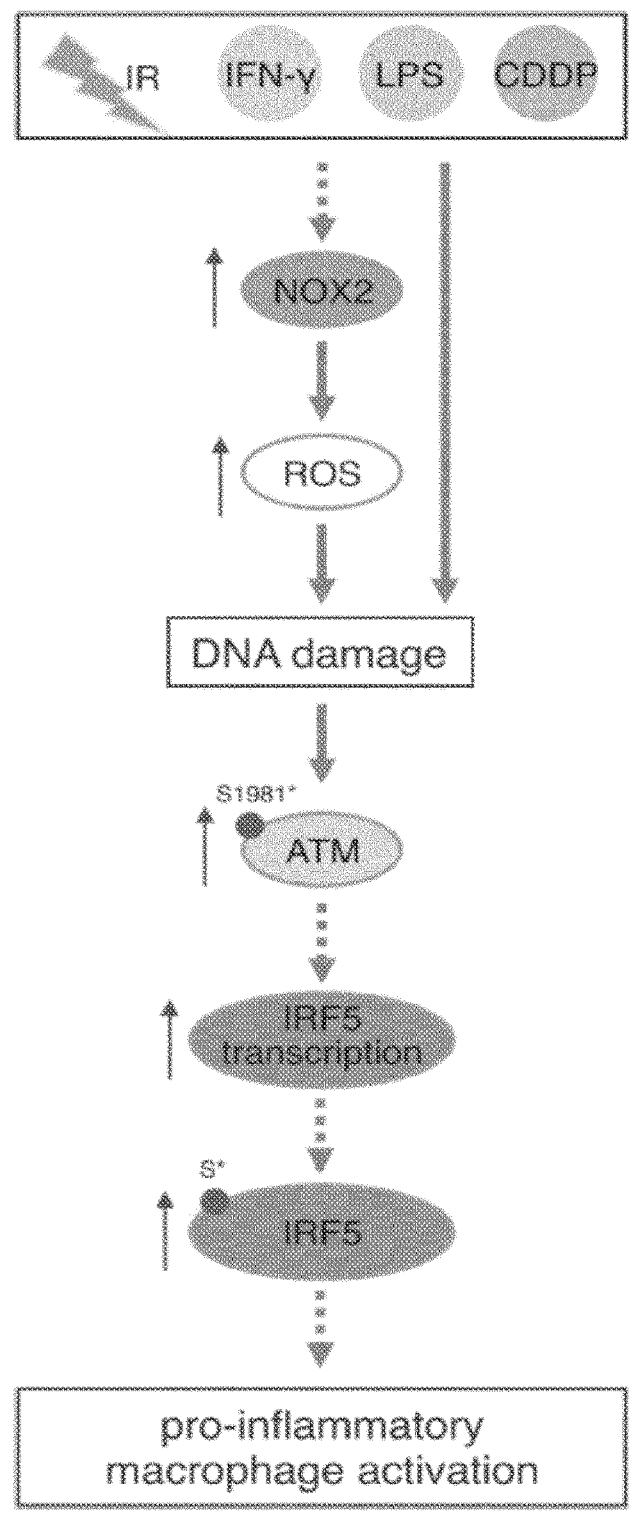

FIG. 7. Proposed model for the roles of NOX2 and ATM activations in proinflammatory macrophage activation.

EXAMPLES

1. Material and Methods

1.1. Cells and Reagents

The human monocyte cell line THP1 cells and the murine macrophage-like RAW264.7 cells were maintained in RMPI-1640-Glutamax medium (Life technology) supplemented with 10% heat-inactivated fetal bovine serum (Hycultec GmbH) and 100 UI/ml penicillin-streptomycin (Life technology). To obtain THP1 macrophages, THP1 monocytes were differentiated with 320 nM of PMA (Invivogen) during 24 h. Then, cells were washed three times to remove PMA and non-adherent cells. For the generation of monocytes-derived macrophages (hMDM), buffy coats from healthy donor blood were obtained from the French blood bank (Etablissement Français du Sang) under the control of convention with the INSERM. In accordance with French law, written informed consent for the use of cells for clinical research was obtained from each donor. Monocytes were obtained from buffy coats and were differentiated into macrophages by using human AB serum in macrophage medium, as previously described [59]. After seven day differentiation, hMDM were harvested and suspended in macrophage medium containing 10% (vol/vol) heat-inactivated FBS, yielding from 91% to 96% of CD14 positive cells that expressed macrophage differentiation markers (C11b and CD71), and macrophage alternative activation markers (CD163 and CD206). All cells were maintained under 5% CO2 humidified atmosphere at 37° C. For hypoxic experiments, cells were incubated in the hypoxic hood (Scitive) under 1% O2, with 5% CO2 humidified atmosphere at 37° C. Dimethyl Sulfoxide (DMSO), Lipopolysaccharides (LPS), Dimethyloxalylglycine (DMOG), NAcetyl-L-cysteine (NAC), Diphenyleneiodonium chloride (DPI), Neocarzinostatin (NCZ), cis-Diammineplatinum(II) dichloride (CDDP) were purchased from Sigma-Aldrich. Recombinant murine IFN-γ (mIFN-γ) was obtained from PeproTech Recombinant Human IFN-γ was from R&D Systems. KU55933 was from Tocris Bioscience. Mn(III)tetrakis (4-benzoic acid) porphyrin Chloride (MnTBAP) was from Calbiochem. Olaparib was from Selleckchem. Phorbol 12-myristate 13-acetate (PMA) was from Invivogen.

1.2. Antibodies

Antibodies used for immunofluorescence were anti-phospho-ATM (Ser1981), anti-iNOS antibodies from Abcam, anti-53BP1 antibody from Cell Signaling Technology, anti-phospho-H2AX (Ser139) antibody from EMD Millipore. Antibodies used for immunoblots were anti-phospho-ATM (Ser1981) (10H11.E12), anti-ATM (D2E2) antibodies from Cell Signaling Technology; anti-IRF5 and anti-IL-1β antibodies were from Abcam; anti-gp91-phox (54.1) (NOX2) antibody was from Santa Cruz. Anti-GAPDH antibody (EMD Millipore) or anti-beta Actin antibody [AC-15] (HRP) (Abcam) was used as a loading control. For immunohistochemistry staining, antimouse CD11 b (Clone M1/70) antibody was purchased from BD Biosciences; antiphospho-ATM (Ser1981) [EP1890Y] antibody was from GeneTex; anti-gp91-phox (54.1) (NOX2) antibody was from Santa Cruz; anti-phospho-H2AX (Ser139) was from EMD Millipore and anti-iNOS antibody was from Abcam.

1.3. Macrophage Activation

Human MDM ($10^6$) were activated by treatment with 2 μg recombinant human IFN-γ for 24 h. THP1 monocytes were differentiated into macrophages by 320 nM PMA for 24 h. Then, macrophages were activated with 20 ng/ml recombinant human IFN-γ or 100 ng/ml LPS during 24 h. RAW264.7 macrophages were activated with 20 ng/ml recombinant murine IFN-γ or 100 ng/ml LPS for 24 h.

1.4. Irradiation

Cells were seeded in 6-well plates, 12-well plates or 25 $cm^2$ flasks and irradiated with gamma-ray irradiator IBL-637 (Cs137, 1 Gy/min, gamma CIS-Bio International, IBA, Saclay, France) or with X-ray irradiator (1Gy/min, X-RAD 320, Precision X-Ray). Cells were harvested at indicated time points (hMDMs and THP1 macrophages at 96 h, RAW264.7 macrophages at 6 h) after irradiation for subsequent experiments.

1.5. RNA-Mediated Interference

The SMARTpool siGENOME ATM siRNA (M-003201-04-0005) against ATM, SMARTpool siGENOME CYBB siRNA (M-011021-01-0005) against NOX2 and siGENOME Non-Targeting siRNA Pool #1 (D-001206-13-05) as control were purchased from Dharmacon. siRNA-5 Control, siRNA-4 and siRNA-5 against ATM were from Sigma. Sequences of siRNAs are as follows: SMARTpool siGENOME CYBB siRNAs (containing siRNA-1: 5' GAA GAC AAC UGG ACA GGA A 3' (SEQ ID NO: 1); siRNA-2: 5' GGA ACU GGG CUG UGA AUG A 3' (SEQ ID NO: 2); siRNA-3: 5' GUG AAU GCC CGA GUC AAU A 3' (SEQ ID NO: 3) and siRNA-4: 5' GAA ACU ACC UAA GAU AGC G 3' (SEQ ID NO: 4)); SMARTpool siGENOME ATM siRNAs (containing siRNA-1: 5' GCA AAG CCC UAG UAA CAU A 3' (SEQ ID NO: 5); siRNA-2: 5' GGG CAU UAC GGG UGU UGA A 3' (SEQ ID NO: 6); siRNA-3: 5' UCG CUU AGC AGG AGG UGU A 3' (SEQ ID NO: 7); siRNA-4: 5' UGA UGA AGA GAG ACG GAA U 3' (SEQ ID NO: 8)); ATM siRNA-5 (5' UGA AGU CCA UUG CUA AUC A 3' (SEQ ID NO: 9)); ATM siRNA-6 (5' AAC AUA CUA CUC AAA GAC A 3' (SEQ ID NO: 10)) and Control siRNA-5 (5' UUC AAU AAA UUC UUG AGG U 3' (SEQ ID NO: 11)). These sequences are listed as SEQ ID NO:1-11 in the enclosed listing. The control siGENOME Non-Targeting siRNAs were a pool of four on-target plus non-targeting siRNAs. INTERFERin™ Reagent (Polyplus Transfection) was used as the siRNA transfection reagent for human monocyte-derived macrophages (hMDM) according to the manufacturer's instructions. Transfection of hMDM was performed as previously described [59].

Briefly, hMDM were seeded (2.5 $10^5$ hMDM/0.25 ml/well in 24-well plate in macrophages medium+10% FBS) and were allowed to adhere to the substrate by culturing at 37° C. for 2 hours prior to siRNAs transfection. siRNAs were pre-diluted in 125 μl of Opti-MEM (Thermo Fisher Scientific) in which 10 μl of INTERFERin were then added. The transfection mix was left to incubate at room temperature for 15 minutes and was added to hMDM to achieve the final concentration of 100 nM siRNAs. The MDMs were then incubated at 37° C. for 24 h. The medium was replaced by fresh macrophage medium supplemented with 10% FBS before subsequent experiments. Lipofectamine RNAi max (life technologies) was used to transfect RAW264.7 macrophages according to the manufacturer's instructions. Briefly, RAW264.7 cells were seeded ($10^5$ cells/1 ml/well in 12-well plate) and were allowed to adhere to the substrate by culturing at 37° C. for 24 hours prior to siRNAs transfection. The transfection mix was added to the final concentration of 10 nM siRNAs. The RAW264.7 cells were then incubated at 37° C. for 24 h before subsequent experiments.

1.6. Immunofluorescence Microscopy

Cells were grown on coverslips and were treated as indicated. After treatment, cells were rinsed twice, fixed with 10% neutral buffered formalin (Sigma-Aldrich) for 10 min and then permeabilized with 0.3% Triton X-100 in PBS for 15 min. Cells were then washed twice with PBS and were blocked with 10% FBS in PBS for 1 h at room temperature, followed by incubation with primary antibodies (1/100) in 10% FBS in PBS for 1 h30 min at room temperature. Then, samples were incubated with secondary antibodies using Alexa Fluor-488 green or Alexa Fluor-546 red (1/500, Life Technologies) and Hoechst 33342 for nuclei (1/1000, Thermo Fisher Scientific) in 10% FBS in PBS for 30 min at room temperature. Coverslips were mounted with Fluoromount-G (SouthernBiotech) ant then visualized with Leica TCS SPE confocal microscope (Leica Microsystemes, France).

1.7. Immunoblots

Cells were washed twice with cold PBS and lysed with NEHN buffer (0.5% NP40, 20% Glycerol, 300 mM NaCl, 20 mM Herps, pH 7.5, and 1 mM EDTA) complemented with 2.5 mM DTT and the protease and phosphatase inhibitor (Roche) at 4° C. 5-20 μg of proteins were separated by NuPAGE 4-12% or 10% SDS-PAGE gel (Invitrogen) and then were transferred onto a nitrocellulose membrane (0.2 Micron, Bio-Rad). Membranes were blocked with 5% non-fat milk or 5% Bovine Serum Albumine (BSA) in Tris-buffered saline and 0.1% Tween 20 (TBS-T) at room temperature for 1 h and then subsequently probed with primary antibodies (1/5000-1/1000) overnight at 4° C. Then, membranes were incubated with appropriate horseradish peroxidase-conjugated anti-rabbit or anti-mouse IgG (SouthernBiotech) for 1 h at room temperature. After 3 washes with TBS-T, immunoblots were revealed using G:BOX Chemi XL1.4 Fluorescent & Chemiluminescent Imaging System (Syngene).

1.8. Detection of ROS Production

Hydrogen peroxide and anion superoxide production were determined by staining cells with 5 μM of 2,7-dichlorodihydrofluorescein diacetate (H2DCFDA, Sigma) for 40 min at 37° C. Cells were then washed twice with Hanks' balanced salt solution (HBSS, from Thermo Fisher Scientific) and suspended in cold HBSS solution containing 1% FBS for FACS analysis.

1.9. Determination of LDH Release

The release of LDH in the supernatants of cultured cells was detected using Cytotoxicity Detection KitPLUS (LDH) from Roche according to the manufacturers' instructions.

1.10. Human Cytokine Profiling

Human MDMs were irradiated at 4 Gy and were further incubated for 96 h. The supernatants were harvested, centrifuged and stored at −80° C. until use. Human cytokines in these supernatants were measured using the proteome profiler Human cytokine array panel A (proteome Profiler™) (R&D Systems) according to the manufacturer's instructions. Briefly, membranes were blocked with the blocking buffer at room temperature for 1 h. Supernatants of hMDMs were mixed with a biotinylated detection antibody cocktail and then incubated with the membranes overnight at 4° C. Membranes were washed three times for 10 min and subsequently incubated with streptavidin-horseradish peroxidase for 30 min at room temperature. Membranes were then washed three times for 10 min and exposed to peroxidase substrate and revealed with the G:BOX Chemi XL1.4 Fluorescent and Chemiluminescent Imaging System (Syngene). Time of exposure was between 1 and 10 min. The images were then analyzed using GeneTools software gel image analysis (Syngene).

1.11. In Vivo Mouse Tumor Model

To generate xenograft tumor model, 4 $10^6$ human colorectal HCT116 cells were inoculated subcutaneously in the flanks of 5-week female nude mice. Two weeks later, the tumors were irradiated at 20 Gy using Variant-NDI-226-n° 87262-YO X-Ray Tube. Tumor volume was monitored every 4-5 days. Mice were sacrificed when tumors in the control group exceeded 1000 mm$^3$.

1.12. Immunohistochemistry

Tumors obtained from in vivo experiments were resected, fixed and embedded in paraffin. Paraffin-embedded tumor biopsies from rectal patients undergoing neoadjuvant radiotherapy were kindly offered by Dr. Celine Mirjolet in Centre Georges-François Leclerc, Dijon. Frozen tumor biopsies from rectal patients before and after radiotherapy were obtained from Gustave Roussy Cancer Center. Tumor sections were then dried, deparaffinized and hydrated, followed by antigen retrieval with 0.01M Sodium Citrate Buffer, pH 6.0 at 97.6° C. for 20 min. After washing with TBST, slides were blocked with 10% FBS in PBS at room temperature for 1 h. Then primary antibodies diluted in 10% FBS in PBS were applied to each section and incubated overnight in humidified chamber at 4° C. After three washes with TBS-T, Alexa Fluor-conjugated secondary antibodies and Hoechst 33342 diluted in 10% FBS in PBS were applied to each section and incubated for 30 min at room temperature. Then, the slides were washed three times with TBS-T and once with water. Coverslips were mounted on slides using Fluoromount G medium (from SouthernBiotech) before visualization with Leica TCS SPE confocal microscope (Leica Microsystemes, France).

1.13. Human Samples

Human tissue samples of locally advanced rectal tumors that were resected 42 days after receiving 45 Gy (1.8 Gy/sessions) concomitantly to chemotherapy (5-FU) (n=4) or left unirradiated (n=4) were obtained from Gustave Roussy Cancer Campus (Villejuif, France). All tumor samples from responders and non-responders to chemoradiotherapy were obtained from Centre Georges Francois Leclerc (Dijon, France). This study was approved by the IRB and the French CCTIRS committee (Comité consultatif sur le traitement de l'information en matière de recherche et de santé) and CNIL (Commission nationale de l'informatique et des libertés).

Characteristics of the patients are shown on Table 1 below.

| Number of patients | 56 |
|---|---|
| Age at diagnosis | |
| Mean (standard deviation) | 65.1 (11.3) |
| Median [min-max] | 66.3 [28.7-85.5] |
| Sex | |
| Male | 36 (64.3%) |
| Female | 20 (35.7%) |
| T stage | |
| 1-2 | 5 (8.9%) |
| 3 | 44 (78.6%) |
| 4 | 7 (12.5%) |
| N stage | |
| 0 | 21 (37.5%) |
| 1 | 32 (57.1%) |
| Unknown | 3 (5.3%) |
| M stage | |
| 0 | 51 (91.1%) |
| 1 | 5 (8.9%) |
| TRG | |
| 1-2 | 29 (51.8%) |
| 3-5 | 27 (48.2%) |
| Number of Gy/fraction | |
| Mean (standard deviation) | 2.1 (0.5) |
| Median [min-max] | 1.8 [1.8-5] |
| <=2 Gy/fraction | 43 (76.8%) |
| >2 Gy/fraction | 13 (23.2%) |
| Total doses | |
| Mean (standard deviation) | 44.1 (3.8) |
| Median [min-max] | 45 [25-51] |
| Number of fractionation | |
| Mean (standard deviation) | 22.9 (4.3) |
| Median [min-max] | 25 [5-30] |
| Concomitant Chemotherapy | |
| No | 25 (44.6%) |
| Yes | 30 (53.6%) |
| Unknown | 1 (1.8%) |
| Time interval RT surgery | |
| Mean (standard deviation) | 42.2 (14.2) |
| Median [min-max] | 42 [7-71] |
| <42 days | 26 (46.4%) |
| >=42 days | 30 (53.6%) |

All these patients (n=56) were diagnosed for locally advanced rectal tumors and characterized the Tumor Node Metastasis (TNM) classification. All human samples were obtained after approval by the institutional review board and ethics committee, with fully informed consents.

1.14. Statistical Analysis

All values were presented as mean±SEM for cellular experiments and were analyzed using Student's t-test. Mann-Whitney test was used for results obtained from animal experiments and human biopsies. GraphPad Prism version 6.0b (GraphPad Software) was employed to perform statistical analysis. Multivariate analysis shown in Table 1 was performed using Wald test.

2. Results

2.1. Cell-Autonomous Activation of Macrophages after Ionizing Radiation

Considering that immune cells (such as Th2 cells and regulatory T cells) may influence the functional reprogramming of macrophages [29], IR-mediated macrophage activation were first analyzed using human colon tumor xenografts in immunodeficient mice. Human colorectal HCT116 cells were subcutaneously inoculated into the right flank of athymic nude mice. After seven days, palpable tumors were irradiated with a single dose of 20 Gy, which resulted in significant tumor growth inhibition, as compared to the controls (FIG. 1A). After twenty-nine days, the residual irradiated tumors did not show an increase of the density of CD11b$^+$ macrophages (not shown) as compared to the controls, but revealed an increased frequency of CD11b$^+$ macrophages that expressed iNOS (iNOS$^+$CD11b$^+$) (FIG. 1B).

A significant accumulation of iNOS$^+$CD11 b$^+$ macrophages was detected in irradiated tumors as compared with non-irradiated tumors (FIG. 1C). The accumulation of iNOS$^+$CD11b$^+$ TAMs positively correlated with tumor response to ionizing radiation, confirming as previously published that the presence iNOS$^+$/pro-inflammatory phenotype macrophages in irradiated tumors is required to modify tumor microenvironment and to elicit the tumor regression. Of note, previous reports characterized this process after relatively low dose IR (2 Gy) [6, 9]. TAMs exhibited an increased phosphorylation of the histone variant H2AX on serine 139 (also known as γ-H2AX) (FIGS. 1D and 1E) underlined an unsuspected link between DNA damage response and macrophage activation. To check the possibility whether IR can directly target and activate macrophages, human THP1 macrophages were irradiated with a single dose of 2 Gy and analyzed by fluorescence microscopy, iNOS and γ-H2AX expressions in the irradiated cells. The increase of iNOS and γ-H2AX expressions in irradiated THP1 macrophages (FIGS. 1F-1H) revealed that IR can directly target macrophages to promote their activation toward a pro-inflammatory phenotype. The expression of a central transcription factor involved in macrophage activation, the interferon regulatory factor 5 (IRF5) [15] was then analyzed by immunoblot and it was observed that after single radiation doses of 2 and 4 Gy, phorbol-12-myristate-13-acetate (PMA)-treated human THP1 monocytes (FIG. 1I), human primary monocyte-derived macrophages (hMDM) (FIG. 1J) and murine RAW264.7 macrophages (FIG. 1K) exhibited an enhanced expression of IRF5 (FIGS. 1I-1K). In addition, through immunoprecipitation experiments, it was observed that after 2 Gy irradiation of RAW264.7 macrophages the proinflammatory transcription factor IRF5 was phosphorylated on serine (data not shown). It has also been demonstrated that after respectively 96 and 12 hours of irradiation, hMDM (FIG. 1L) and murine RAW264.7 macrophages (FIG. 1M) released IL-1β and IL-8, two pro-inflammatory cytokines. To further complete the cytokine profile analysis, levels of pro- and anti-inflammatory cytokines were determined and it was observed an increased secretion of pro-inflammatory cytokines (such as IFN-γ, IL-23, IL-6, IL-8 or TNF-α) by 4 Gy-irradiated hMDM as compared with controls (FIGS. 1N and 1O). Altogether, these results indicate that ionizing radiation can promote a cell-autonomous activation of macrophages toward a pro-inflammatory phenotype.

2.2. ATM-Mediated DNA Damage Response Induces IRF5 Expression in Response to Ionizing Radiation To further characterize molecular mechanisms involved in IR-elicited macrophage activation toward a pro-inflammatory phenotype, the induction of DNA damage-associated signaling pathways was first studied in irradiated macrophages. Fifteen minutes after single radiation dose of 2 Gy, PMA-treated human THP1 monocytes (FIGS. 2A-2C) exhibited a strong nuclear accumulation of γ-H2AX$^+$ foci (FIGS. 2A and 2B) and of 53BP1$^+$ foci (FIGS. 2A and 2C) that could still be detected 6 hours after irradiation (FIGS. 2B and 2C), revealing that DNA double strand breaks are produced in response to IR. One hour after single radiation dose of 2 Gy, murine RAW264.7 macrophages also displayed increased γ-H2AX$^+$ foci (FIGS. 2D and 2E). Considering that the kinase ATM (mutated in the inherited recessive autosomal disease ataxia telangiectasia) is the major kinase involved in the phosphorylation of H2AX (on serine 139) [31], the role of ATM was evaluated in the activation of macrophages in response to IR. The vast majority (more that 80%) of 2 Gy-irradiated murine RAW264.7 macrophages exhibited the activating autophosphorylation of ATM on serine 1981 (ATMS1981*) 1-hour post-irradiation (FIGS. 2D and 2F). These results were confirmed by immunoblots (FIGS. 2G and 2H), which also revealed the positive correlation between ATMS1981* and IRF5 expression when hMDM (FIG. 2G) or murine RAW264.7 macrophages (FIG. 2H) were irradiated with single doses of 2, 4 and 8 Gy. In addition, an increase of ATM phosphorylation/activation in CD68$^+$ macrophages was detected in tumor samples after radiotherapy of rectal cancer patients (FIGS. 2I and 2J), as compared to unirradiated patients. The ATM phosphorylation/activation was positively correlated with the increased frequencies of tumor-associated iNOS$^+$CD68$^+$ macrophages that have been detected 6 weeks after radiotherapy (FIGS. 2K and 2L), demonstrating that the kinase ATM was sustainably activated in macrophages after radiotherapy. The impact of ATM inactivation was next investigated on IR-induced macrophage activation. The depletion of ATM by means of specific small interfering RNA (FIG. 2M) or pharmacological inhibition of ATM with KU55933 (FIGS. 2N and 2O) impaired γ-H2AX and ATMS1981* phosphorylations and the up-regulation of IRF5 expression that was detected respectively, 6 and 96 hours after 2 Gy and 4 Gy single dose irradiation of murine RAW264.7 macrophages (FIGS. 2M, 2N) or hMDM (FIG. 2O) without altering macrophage viability (not shown).

More importantly, an enhancement of ATM activation was also observed through the pharmacological inhibition of poly(ADP-ribose)polymerase (PARP) with Olaparib further enhanced inflammatory macrophage activation elicited by IR (as revealed by the increased expression of IRF5 (FIG. 2P). It was also demonstrated that ATM regulated the expression of IRF5 at transcriptional level (as shown by quantitative real-time (RT) PCR (Data not shown), indicating that the kinase ATM plays a central role during IR-mediated activation of macrophages toward a pro-inflammatory phenotype.

2.3. The Kinase ATM Dictates Classical Macrophage Activation

In order to check whether the activation of ATM was a common feature of pro-inflammatory macrophage activation in response to various agents, the presence of DNA damage-associated nuclear foci was analyzed in response to classical macrophage activators, such as IFN-γ or LPS [32]. Using confocal microscopy, an accumulation of ATMS1981*+ and γ-H2AX+ foci was detected in the nuclei of murine RAW264.7 macrophages that were treated during 24 hours with recombinant murine IFN-γ (mIFN-γ) or LPS (FIGS. 3A-3C). Using immunoblots, it was also observed that the activation of ATM was concomitant with an increased expression of IRF5 in the PMA-treated THP1 monocytes (FIGS. 3D and 3F) or murine RAW264.7 macrophages (FIG. 3E) stimulated with human or murine IFN-γ (FIGS. 3D and 3E) or LPS (FIG. 3F). Interestingly, treatments of these macrophages with some other DNA strand break inducers (such as Cisplatin (FIGS. 3A-3C, 3G and 3H) or neocarzinostatin (FIG. 3I)) or modulators of DNA repair (such as Olaparib (FIG. 3J)), not only activated ATM but also increased IRF5 expression (FIGS. 3G-3J).

The results that are observed in absence of macrophage cytotoxicity suggest that the DNA damage response signaling pathway might be a common pathway involved in classical macrophage activation. Moreover, the pharmacological inhibition (FIGS. 3K and 3L) and the specific depletion (FIGS. 3M and 3N) of ATM inhibited the increase of IRF5 expression that was previously detected after the treatment of PMA-treated THP1 monocytes (FIG. 3K), murine RAW264.7 macrophages (FIGS. 3L and 3M) or hMDM (FIG. 3N) with human or murine IFN-γ (FIGS. 3K-3N), confirming the essential role of the kinase ATM in classical macrophage activation.

2.4. ROS Production Induces ATMS1981* Phosphorylation and IRF5 Expression During Macrophage Activation Considering that reactive oxygen species (ROS) have been involved in both ATM activation and macrophage differentiation [33, 34], the role of ROS production during macrophage activation was investigated. Using flow cytometry to detect the conversion of the non-fluorescent dye 2,7-dichlorohydro fluorescein diacetate (H2DCFDA) into fluorescent 2,7-dichlorohydro fluorescein (DCF) when ROS are produced, we evaluated the ability of murine RAW264.7 macrophages to generate ROS following IR or mIFN-γ treatment and revealed that both these treatments induced ROS production (FIGS. 4A-4D). Importantly, we demonstrated that the antioxidant N-acetyl cysteine (NAC) and the superoxide dismutase (SOD) mimetic Mn(III)tetrakis (4-benzoic acid) (MnTBAP) that blunted the ROS production (FIGS. 4A-4D), inhibited also the activating phosphorylation of ATM (ATMS1981*) (FIGS. 4E-4G) and reduced the increased expression of IRF5 (FIGS. 4E-4G) that we observed after treatment with IR (FIGS. 4E and 4G) or mIFN-γ (FIG. 4F) of RAW264.7 macrophages (FIGS. 4E and 4F) or treatment with IR of PMA-treated THP1 monocytes (FIG. 4G) without impacting macrophage viability (not shown). These results suggested that ROS production may dictate the classical pro-inflammatory state of macrophages.

Then, it was assessed whether low oxygen tension (also known as hypoxia) which is a physio-pathological situation known to reduce the generation of ROS [35] may also impact the activation of macrophages. The effects of hypoxic conditions (1% oxygen) and of a small molecule inhibitor of prolyl hydroxylase domain (PHD)-containing proteins, the dimethyloxallyl glycine (DMOG) (which mimics hypoxia) were thus evaluated on IR-mediated pro-inflammatory macrophage activation. It was observed that IR-mediated ATMS1981* and IRF5 expressions were reduced in RAW264.7 macrophages that have been incubated in hypoxic conditions (FIG. 4H) or treated with DMOG (FIG. 4I), as compared to control cells. The results were confirmed after stimulation of murine RAW264.7 macrophages with mIFN-γ (FIGS. 4J and 4K). Altogether, these results indicate that, by controlling activating phosphorylation of ATM and the induction of the IRF5, ROS produced in the stimulated macrophages play a key role in the activation process.

2.5. The NADPH Oxydase (NOX2) is Responsible for ROS Production and ATM Phosphorylation During Macrophage Activation The NADPH oxidases (NOX) and dual oxidase (DUOX) are major regulated sources of ROS generation [36]. To characterize mechanisms that are involved in ROS generation during macrophage activation, the role of NADPH oxidase 2 (NOX2), which is mainly expressed in macrophages and neutrophils [35, 36], was examined. First, using immunoblots, it was observed that NOX2 was up-regulated after irradiation of PMA-treated THP1 monocytes (FIG. 5A) with single doses of 2 and 4 Gy. These results were confirmed with the treatments of hMDM (FIG. 5B), PMA-treated THP1 monocytes (FIG. 5C) and RAW264.7 macrophages (FIGS. 5D and 5E) with human or murine IFN-γ (FIGS. 5B, 5C and 5E) or IR (FIG. 5D). NOX2 expression was also found increased in CD68+ macrophages that were detected in tumor samples obtained 6 weeks after radiotherapy of rectal cancer patients (FIGS. 5F and 5G), as compared to biopsies obtained from the same patients before radiotherapy. To precise the role of NOX2 during macrophage activation, the effect of the pharmacological NADPH oxidase inhibitor, diphenylene iodonium (DPI) was evaluated on ROS production, ATMPS1981* and IRF5 up-regulation detected after the treatment of RAW264.7 macrophages with IR (FIGS. 5H, 5I and 5L) or mIFN-γ (FIGS. 5J, 5K and 5M). It was demonstrated that DPI impaired all events of the above-described signaling cascade (FIGS. 5H-5M) without modifying macrophage viability (not shown). In addition, depletion of NOX2 with specific small interfering RNA on irradiated (FIG. 5N) or mIFN-γ treated (FIG. 5O) RAW264.7 macrophages also reduced ATMS1981* and IRF5 up-regulation as revealed by immunoblots, in comparison to control cells. These results demonstrate that the induction of NOX2-dependent ATM activation is required for tuning macrophages toward a pro-inflammatory phenotype.

2.6. The Alteration of NOX2/ATM-Dependent Tumor Macrophage Activation is Associated with Poor Prognosis after Radiotherapy Despite the fact that neo-adjuvant chemo-radiotherapy for locally advanced rectal cancer patients improved local control of the tumors, only 15% of patients exhibit a complete response to treatment [37]. In this context, it was analyzed whether the perturbation of the signaling pathway (NOX2→ROS→ATMS1981*) involved in the macrophage activation toward a pro-inflammatory phenotype may be associated with the absence of local response to radiotherapy. Resected specimens of rectal cancer patients obtained after neo-adjuvant radiotherapy that have been performed before radical tumor resection were analyzed. According to the tumor regression grade (TRG) criteria of Mandard et al ([63]), these patients were classified into "good responders" (TRG≤2, n=29) and "bad responders" (TRG≥3, n=27) (Table 1 above). The total number of CD68$^+$ tumor-associated macrophages were analyzed in both groups of irradiated tumors and significant difference in the CD68$^+$ TAMs infiltration was not detected (FIG. 6A). In addition, the auto-phosphorylation ATMS1981* was detected in approximately 20% of TAMs (FIG. 6B), but a significant difference on the frequencies of TAMs exhibiting the auto-phosphorylation ATMS1981* (ATMS1981*+ CD68$^+$) was not observed between the both groups of tumors (FIG. 6C).

Interestingly, it was detected a significant increase in the frequency of TAMs revealing an enhanced expression of the inducible nitric oxide synthase (iNOS$^+$CD68$^+$) on tumor samples obtained from "good responders" as compared to those obtained from "bad responders" (FIGS. 6D and 6E), confirming that macrophage activation toward a pro-inflammatory phenotype is associated with the local tumor control.

Finally, higher frequencies of TAMs showing an up-regulation of NOX2 expression (NOX2$^+$CD68$^+$) were observed in biopsies obtained from "good responders", as compared to those obtained from "bad responders" (FIGS. 6F and 6G), revealing that the detection of NOX2 expression on TAMs may serve as a predictive factor for radiotherapy effectiveness. Multivariate statistical analysis confirmed these results (Table 2).

TABLE 2

Multivariate analysis of macrophage histological markers in rectal cancer response to neoadjuvant radiotherapy. The statistical comparisons of indicated histological markers between "good responders" (TRG ≤ 2, n = 29) and "bad responders" (TRG ≥ 3, n = 27) have been adjusted on TNM stages, time interval between radiotherapy and surgery and concomitance with chemotherapy. Median cuts off, Odds Ratios (OR) and 95% confidence interval (95% CI) are indicated. P values were calculated using Wald test.

|  | OR TRG (3-4-5) vs (1-2) | 95% CI | P-value |
|---|---|---|---|
| CD68+/mm2 median cut off |  |  | 0.635 |
| <376.23 | 1 |  |  |
| >=376.23 | 1.369 | [0.374-5.010] |  |
| iNOS+/CD68+ (%) median cut off |  |  | 0.003 |
| <53.72 | 1 |  |  |
| >=53.72 | 0.089 | [0.018-0.431] |  |
| NOX2+/CD68+ (%) median cut off |  |  | 0.006 |
| <55.07 | 1 |  |  |
| >=55.07 | 0.077 | [0.013-0.472] |  |
| ATMS1981*+/CD68+ (%) median cut off |  |  | 0.339 |
| <14.93 | 1 |  |  |
| >=14.93 | 0.513 | [0.131-2.013] |  |

Altogether, these results confirm that the NOX2→ROS→ATMS1981* cascade may contribute to an efficient macrophage activation in response to radiotherapy.

BIBLIOGRAPHIC REFERENCES

1. Azzam, E. I., J. P. Jay-Gerin, and D. Pain, *Ionizing radiation-induced metabolic oxidative stress and prolonged cell injury*. Cancer Lett, 2012. 327(1-2): p. 48-60.
2. Hekim, N., et al., *Radiation triggering immune response and inflammation*. Cancer Lett, 2015. 368(2): p. 156-63.
3. Park, B., C. Yee, and K. M. Lee, *The effect of radiation on the immune response to cancers*. Int J Mol Sci, 2014. 15(1): p. 927-43.
4. Kroemer, G., et al., *Immunogenic cell death in cancer therapy*. Annu Rev Immunol, 2013. 31: p. 51-72.
5. Ghiringhelli, F., et al., *Activation of the NLRP3 inflammasome in dendritic cells induces IL-1 beta-dependent adaptive immunity against tumors*. Nat Med, 2009. 15(10): p. 1170-8.
6. Prakash, H., et al., *Low doses of gamma irradiation potentially modifies immunosuppressive tumor microenvironment by retuning tumor-associated macrophages: lesson from insulinoma*. Carcinogenesis, 2016. 37(3): p. 301-13.
7. Merrick, A., et al., *Immunosuppressive effects of radiation on human dendritic cells: reduced IL-12 production on activation and impairment of naive T-cell priming*. Br J Cancer, 2005. 92(8): p. 1450-8.
8. Price, J. G., et al., *CDKN1A regulates Langerhans cell survival and promotes Treg cell generation upon exposure to ionizing irradiation*. Nat Immunol, 2015. 16(10): p. 1060-8.
9. Klug, F., et al., *Low-dose irradiation programs macrophage differentiation to an iNOS(+)/M1 phenotype that orchestrates effective T cell immunotherapy*. Cancer Cell, 2013. 24(5): p. 589-602.
10. Chiang, C. S., et al., *Irradiation promotes an m2 macrophage phenotype in tumor hypoxia*. Front Oncol, 2012. 2: p. 89.
11. Franklin, R. A., et al., *The cellular and molecular origin of tumor-associated macrophages*. Science, 2014. 344 (6186): p. 921-5.
12. Mosser, D. M. and J. P. Edwards, *Exploring the full spectrum of macrophage activation*. Nat Rev Immunol, 2008. 8(12): p. 958-69.
13. Weiss, M., et al., *IRF5 controls both acute and chronic inflammation*. Proc Natl Acad Sci USA, 2015. 112(35): p. 11001-6.
14. Weiss, M., et al., *IRF5 is a specific marker of inflammatory macrophages in vivo*. Mediators Inflamm, 2013. 2013: p. 245804.
15. Krausgruber, T., et al., *IRF5 promotes inflammatory macrophage polarization and TH1-TH17 responses*. Nat Immunol, 2011. 12(3): p. 231-8.
16. Satoh, T., et al., *The Jmjd3-Irf4 axis regulates M2 macrophage polarization and host responses against helminth infection*. Nat Immunol, 2010. 11(10): p. 936-44.
17. Cosin-Roger, J., et al., *The activation of Wnt signaling by a STAT6-dependent macrophage phenotype promotes mucosal repair in murine IBD*. Mucosal Immunol, 2015.
18. Kapoor, N., et al., *Transcription factors STAT6 and KLF4 implement macrophage polarization via the dual catalytic powers of MCPIP*. J Immunol, 2015. 194(12): p. 6011-23.
19. Rodriguez-Zapata, M., et al., *Defective reactive oxygen metabolite generation by macrophages from acute brucellosis patients*. Infection, 1997. 25(3): p. 187-8.
20. Colegio, O. R., et al., *Functional polarization of tumour-associated macrophages by tumour-derived lactic acid*. Nature, 2014. 513(7519): p. 559-63.
21. Wen, Z., et al., *Increased metabolites of 5-lipoxygenase from hypoxic ovarian cancer cells promote tumor-associated macrophage infiltration*. Oncogene, 2015. 34(10): p. 1241-52.

22. Mantovani, A., et al., *Macrophage polarization: tumor-associated macrophages as a paradigm for polarized M2 mononuclear phagocytes.* Trends Immunol, 2002. 23(11): p. 549-55.
23. Condeelis, J. and J. W. Pollard, *Macrophages: obligate partners for tumor cell migration, invasion, and metastasis.* Cell, 2006. 124(2): p. 263-6.
24. Coffelt, S. B., R. Hughes, and C. E. Lewis, *Tumor-associated macrophages: effectors of angiogenesis and tumor progression.* Biochim Biophys Acta, 2009. 1796 (1): p. 11-8.
25. Lee, C. H., et al., *Prognostic significance of macrophage infiltration in leiomyosarcomas.* Clin Cancer Res, 2008. 14(5): p. 1423-30.
26. Jensen, T. O., et al., *Macrophage markers in serum and tumor have prognostic impact in American Joint Committee on Cancer stage I/II melanoma.* J Clin Oncol, 2009. 27(20): p. 3330-7.
27. Steidl, C., et al., *Tumor-associated macrophages and survival in classic Hodgkin's lymphoma.* N Engl J Med, 2010. 362(10): p. 875-85.
28. Chung, F. T., et al., *Tumor-associated macrophages correlate with response to epidermal growth factor receptor-tyrosine kinase inhibitors in advanced nonsmall cell lung cancer.* Int J Cancer, 2012. 131(3): p. E227-35.
29. Mantovani, A. and P. Allavena, *The interaction of anticancer therapies with tumor-associated macrophages.* J Exp Med, 2015. 212(4): p. 435-45.
30. De Palma, M. and C. E. Lewis, *Macrophage regulation of tumor responses to anticancer therapies.* Cancer Cell, 2013. 23(3): p. 277-86.
31. Burma, S., et al., *ATM phosphorylates histone H2AX in response to DNA double-strand breaks.* J Biol Chem, 2001. 276(45): p. 42462-7.
32. Murray, P. J., et al., *Macrophage activation and polarization: nomenclature and experimental guidelines.* Immunity, 2014. 41(1): p. 14-20.
33. Guo, Z., et al., *ATM activation by oxidative stress.* Science, 2010. 330(6003): p. 517-21.
34. Zhang, Y., et al., *ROS play a critical role in the differentiation of alternatively activated macrophages and the occurrence of tumor-associated macrophages.* Cell Res, 2013. 23(7): p. 898-914.
35. Bedard, K. and K. H. Krause, *The NOX family of ROS-generating NADPH oxidases: physiology and pathophysiology.* Physiol Rev, 2007. 87(1): p. 245-313.
36. Lambeth, J. D., *NOX enzymes and the biology of reactive oxygen.* Nat Rev Immunol, 2004. 4(3): p. 181-9.
37. Trakarnsanga, A., S. Ithimakin, and M. R. Weiser, *Treatment of locally advanced rectal cancer: controversies and questions.* World J Gastroenterol, 2012. 18(39): p. 5521-32.
38. Galli, S. J., N. Borregaard, and T. A. Wynn, *Phenotypic and functional plasticity of cells of innate immunity: macrophages, mast cells and neutrophils.* Nat Immunol, 2011. 12(11): p. 1035-44.
39. Mantovani, A. and M. Locati, *Tumor-associated macrophages as a paradigm of macrophage plasticity, diversity, and polarization: lessons and open questions.* Arterioscler Thromb Vasc Biol, 2013. 33(7): p. 1478-83.
40. Georgoudaki, A. M., et al., *Reprogramming Tumor-Associated Macrophages by Antibody Targeting Inhibits Cancer Progression and Metastasis.* Cell Rep, 2016.
41. Tan, H. Y., et al., *Autophagy-induced RelB/p52 activation mediates tumourassociated macrophage repolarisation and suppression of hepatocellular carcinoma by natural compound baicalin.* Cell Death Dis, 2015. 6: p. e1942.
42. Rolny, C., et al., *HRG inhibits tumor growth and metastasis by inducing macrophage polarization and vessel normalization through downregulation of PIGF.* Cancer Cell, 2011. 19(1): p. 31-44.
43. Buhtoiarov, I. N., et al., *Anti-tumour synergy of cytotoxic chemotherapy and anti-CD40 plus CpG-ODN immunotherapy through repolarization of tumourassociated macrophages.* Immunology, 2011. 132(2): p. 226-39.
44. Coscia, M., et al., *Zoledronic acid repolarizes tumour-associated macrophages and inhibits mammary carcinogenesis by targeting the mevalonate pathway.* J Cell Mol Med, 2010. 14(12): p. 2803-15.
45. Saliba, D. G., et al., *IRF5:RelA interaction targets inflammatory genes in macrophages.* Cell Rep, 2014. 8(5): p. 1308-17.
46. Bowdridge, S. and W. C. Gause, *Regulation of alternative macrophage activation by chromatin remodeling.* Nat Immunol, 2010. 11(10): p. 879-81.
47. Krausgruber, T., et al., *IRF5 is required for late-phase TNF secretion by human dendritic cells.* Blood, 2010. 115(22): p. 4421-30.
48. Lien, C., et al., *Critical role of IRF-5 in regulation of B-cell differentiation.* Proc Natl Acad Sci USA, 2010. 107(10): p. 4664-8.
49. Jia, X., et al., *Association of the IRF5 rs2004640 polymorphism with rheumatoid arthritis: a meta-analysis.* Rheumatol Int, 2013. 33(11): p. 2757-61.
50. Graham, R. R., et al., *A common haplotype of interferon regulatory factor 5 (IRF5) regulates splicing and expression and is associated with increased risk of systemic lupus erythematosus.* Nat Genet, 2006. 38(5): p. 550-5.
51. Carmona, F. D., et al., *The systemic lupus erythematosus IRF5 risk haplotype is associated with systemic sclerosis.* PLoS One, 2013. 8(1): p. e54419.
52. Baskar, R., et al., *Cancer and radiation therapy: current advances and future directions.* Int J Med Sci, 2012. 9(3): p. 193-9.
53. Eriksson, D. and T. Stigbrand, *Radiation-induced cell death mechanisms.* Tumour Biol, 2010. 31(4): p. 363-72.
54. Matei, I. R., C. J. Guidos, and J. S. Danska, *ATM-dependent DNA damage surveillance in T-cell development and leukemogenesis:* the DSB connection. Immunol Rev, 2006. 209: p. 142-58.
55. So, E. Y. and T. Ouchi, *Translational initiation regulated by ATM in dendritic cells development.* Cell Death Dis, 2014. 5: p. e1418.
56. So, E. Y., M. Kozicki, and T. Ouchi, *Roles of DNA Damage Response Proteins in Mitogen-Induced THP1 Differentiation into Macrophage.* J Cancer Biol Res, 2013. 1(1).
57. Hartlova, A., et al., *DNA damage primes the type I interferon system via the cytosolic DNA sensor STING to promote anti-microbial innate immunity.* Immunity, 2015. 42(2): p. 332-43.
58. Pereira-Lopes, S., et al., *NBS1 is required for macrophage homeostasis and functional activity in mice.* Blood, 2015. 126(22): p. 2502-10.
59. Allouch, A., et al., *p21-mediated RNR2 repression restricts HIV-1 replication in macrophages by inhibiting dNTP biosynthesis pathway.* Proc Natl Acad Sci USA, 2013. 110(42): p. E3997-4006.
60. Sorce, S., et al., *NADPH oxidases as drug targets and biomarkers in neurodegenerative diseases: What is the evidence?* Free Radical Biology and Medicine, 2017. 112: p 387-396
61. Paull, T. T., *Mechanisms of ATM Activation.* Annu Rev Biochem, 2015. 84: p 711-738.
62. Blackford, A. N. and Jackson, S. P., *ATM, ATR, and DNA-PK: The Trinity at the Heart of the DNA Damage Response.* Mol Cell. 2017. 66(6): p 801-817.
63. Mandard A M, Dalibard F, Mandard J C, et al. *Pathologic assessment of tumor regression after preoperative chemoradiotherapy of esophageal carcinoma.* Clinicopathologic correlations. Cancer. 1994; 73(11):2680-268

The invention claimed is:

1. A method for treating cancer, comprising the steps of:
   a) selecting a tumor sample from a subject diagnosed with cancer that comprises CD68+ macrophages,
   b) measuring by flow cytometry the NOX2 expression level of the CD68+ macrophages;
   c) measuring the NOX2 expression level of a reference sample comprising CD68+ macrophages from radiotherapy bad responder patients characterized by a Tumor Regression Grade superior to 3 after radiotherapy, and
   d) administering radiotherapy to the subject, wherein the subject has a NOX2 expression level in CD68+ macrophages higher than in said reference sample NOX2 expression level.

2. The method according to claim 1, wherein the selected sample and the reference sample comprise more than 70% CD68+ macrophages.

3. The method of claim 1, wherein said subject is a human patient.

4. The method of claim 1, wherein said subject suffers from a glioma, a lymphoma, a melanoma, a sarcoma, a head and neck tumor, a breast cancer, or a lung cancer.

5. The method of claim 1, wherein the NOX2 expression level in the selected sample and the reference sample is determined using an anti-NOX2 antibody labeled for flow cytometry.

6. The method of claim 1, wherein the tumor sample is a solid tumor tissue.

* * * * *

SEQUENCE LISTING

<160> NUMBER OF SEQ ID NOS: 19

<210> SEQ ID NO 1
<211> LENGTH: 19
<212> TYPE: RNA
<213> ORGANISM: artificial
<220> FEATURE:
<223> OTHER INFORMATION: CYBB siRNA1

<400> SEQUENCE: 1
gaagacaacu ggacaggaa                                                    19

<210> SEQ ID NO 2
<211> LENGTH: 19
<212> TYPE: RNA
<213> ORGANISM: artificial
<220> FEATURE:
<223> OTHER INFORMATION: CYBB siRNA2

<400> SEQUENCE: 2
ggaacugggc ugugaauga                                                    19

<210> SEQ ID NO 3
<211> LENGTH: 19
<212> TYPE: RNA
<213> ORGANISM: artificial
<220> FEATURE:
<223> OTHER INFORMATION: CYBB siRNA3

<400> SEQUENCE: 3
gugaaugccc gagucaaua                                                    19

<210> SEQ ID NO 4
<211> LENGTH: 19
<212> TYPE: RNA
<213> ORGANISM: artificial
<220> FEATURE:
<223> OTHER INFORMATION: CYBB siRNA4

<400> SEQUENCE: 4
gaaacuaccu aagauagcg                                                    19

<210> SEQ ID NO 5
<211> LENGTH: 19
<212> TYPE: RNA
<213> ORGANISM: artificial
<220> FEATURE:
<223> OTHER INFORMATION: ATM siRNA1

<400> SEQUENCE: 5
gcaaagcccu aguaacaua                                                    19

<210> SEQ ID NO 6
<211> LENGTH: 19
<212> TYPE: RNA
<213> ORGANISM: artificial
<220> FEATURE:
<223> OTHER INFORMATION: ATM siRNA2

<400> SEQUENCE: 6
gggcauuacg gguguugaa                                                    19

<210> SEQ ID NO 7
<211> LENGTH: 19
<212> TYPE: RNA
<213> ORGANISM: artificial

```
<220> FEATURE:
<223> OTHER INFORMATION: ATM siRNA3

<400> SEQUENCE: 7
ucgcuuagca ggaggugua                                                    19

<210> SEQ ID NO 8
<211> LENGTH: 19
<212> TYPE: RNA
<213> ORGANISM: artificial
<220> FEATURE:
<223> OTHER INFORMATION: ATM siRNA4

<400> SEQUENCE: 8
ugaugaagag agacggaau                                                    19

<210> SEQ ID NO 9
<211> LENGTH: 19
<212> TYPE: RNA
<213> ORGANISM: artificial
<220> FEATURE:
<223> OTHER INFORMATION: ATM siRNA5

<400> SEQUENCE: 9
ugaaguccau ugcuaauca                                                    19

<210> SEQ ID NO 10
<211> LENGTH: 19
<212> TYPE: RNA
<213> ORGANISM: artificial
<220> FEATURE:
<223> OTHER INFORMATION: ATM siRNA6

<400> SEQUENCE: 10
aacauacuac ucaaagaca                                                    19

<210> SEQ ID NO 11
<211> LENGTH: 19
<212> TYPE: RNA
<213> ORGANISM: artificial
<220> FEATURE:
<223> OTHER INFORMATION: control siRNA5

<400> SEQUENCE: 11
uucaauaaau ucuugaggu                                                    19

<210> SEQ ID NO 12
<211> LENGTH: 4353
<212> TYPE: DNA
<213> ORGANISM: homo sapiens
<220> FEATURE:
<221> NAME/KEY: misc_feature
<223> OTHER INFORMATION: NM_000397 mRNA of the CYBB gene

<400> SEQUENCE: 12
attggaagaa gaagcatagt atagaagaaa ggcaaacaca acacattcaa cctctgccac        60 catgggaac tgggctgtga atgaggggct ctccattttt gtcattctgg tttggctggg       120
gttgaacgtc ttcctctttg tctggtatta ccgggtttat gatattccac ctaagttctt       180
ttacacaaga aaacttcttg ggtcagcact ggcactggcc agggcccctg cagcctgcct       240
gaatttcaac tgcatgctga ttctcttgcc agtctgtcga aatctgctgt ccttcctcag       300
gggttccagt gcgtgctgct caacaagagt tcgaagacaa ctggacagga atctcacctt       360
tcataaaatg gtggcatgga tgattgcact tcactctgcg attcacacca ttgcacatct       420
```

```
atttaatgtg gaatggtgtg tgaatgcccg agtcaataat tctgatcctt attcagtagc    480
actctctgaa cttggagaca ggcaaaatga aagttatctc aatttttgctc gaaagagaat    540
aaagaaccct gaaggaggcc tgtacctggc tgtgaccctg ttggcaggca tcactggagt    600
tgtcatcacg ctgtgcctca tattaattat cacttcctcc accaaaacca tccggaggtc    660
ttactttgaa gtcttttggt acacacatca tctctttgtg atcttcttca ttggccttgc    720
catccatgga gctgaacgaa ttgtacgtgg gcagaccgca gagagtttgg ctgtgcataa    780
tataacagtt tgtgaacaaa aaatctcaga atggggaaaa ataaaggaat gcccaatccc    840
tcagtttgct ggaaaccctc ctatgacttg gaaatggata gtgggtccca tgtttctgta    900
tctctgtgag aggttggtgc ggttttggcg atctcaacag aaggtggtca tcaccaaggt    960
ggtcactcac cctttcaaaa ccatcgagct acagatgaag aagaagggt tcaaaatgga    1020
agtgggacaa tacattttg tcaagtgccc aaaggtgtcc aagctggagt ggcacccttt    1080
tacactgaca tccgcccctg aggaagactt ctttagtatc catatccgca tcgttgggga    1140
ctggacagag gggctgttca atgcttgtgg ctgtgataag caggagtttc aagatgcgtg    1200
gaaactacct aagatagcgg ttgatgggcc ctttggcact gccagtgaag atgtgttcag    1260
ctatgaggtg gtgatgttag tgggagcagg gattgggtc acaccttcg catccattct    1320
caagtcagtc tggtacaaat attgcaataa cgccaccaat ctgaagctca aaagatcta    1380
cttctactgg ctgtgccggg acacacatgc ctttgagtgg tttgcagatc tgctgcaact    1440
gctggagagc cagatgcagg aaaggaacaa tgccggcttc ctcagctaca acatctacct    1500
cactggctgg gatgagtctc aggccaatca ctttgctgtg caccatgatg aggagaaaga    1560
tgtgatcaca ggcctgaaac aaaagacttt gtatggacgg cccaactggg ataatgaatt    1620
caagacaatt gcaagtcaac ccctaatac cagaatagga gttttcctct gtggacctga    1680
agccttggct gaaaccctga gtaaacaaag catctccaac tctgagtctg ccctcgggg    1740
agtgcatttc atttcaaca aggaaaactt ctaacttgtc tcttccatga ggaaataaat    1800
gtgggttgtg ctgccaaatg ctcaaataat gctaattgat aatataaata cccctgctt    1860
aaaaatggac aaaagaaac tataatgtaa tggttttccc ttaaaggaat gtcaaagatt    1920
gtttgatagt gataagttac atttatgtgg agctctatgg ttttgagagc acttttacaa    1980
acattatttc attttttcc tctcagtaat gtcagtggaa gttagggaaa agattcttgg    2040
actcaatttt agaatcaaaa gggaaggat caaaaggttc agtaacttcc ctaagattat    2100
gaaactgtga ccagatctag cccatcttac tccaggtttg atactctttc cacaatactg    2160
agctgcctca gaatcctcaa atcagttttt tatattcccc aaaagaagaa ggaaaccaag    2220
gagtagctat atatttctac tttgtgtcat ttttgccatc attatatca tactgaagga    2280
aattttccag atcattagga cataatacat gttgagagtg tctcaacact tattagtgac    2340
agtattgaca tctgagcata ctccagttta ctaatacagc agggtaactg gccagatgt    2400
tctttctaca gaagaatatt ggattgattg gagttaatgt aatactcatc atttaccact    2460
gtgcttggca gagagcggat actcaagtaa gttttgttaa atgaatgaat gaatttagaa    2520
ccacacaatg ccaagataga attaatttaa agccttaaac aaaatttatc taagaaata    2580
acttctatta ctgtcataga ccaaaggaat ctgattctcc ctagggtcaa gaacaggcta    2640
aggatactaa ccaataggat tgcctgaagg gttctgcaca ttcttatttg aagcatgaaa    2700
aaagaggggtt ggaggtggag aattaacctc ctgccatgac tctggctcat ctagtcctgc    2760
```

```
tccttgtgct ataaaataaa tgcagactaa tttcctgccc aaagtggtct tctccagcta    2820
gcccttatga atattgaact taggaattgt gacaaatatg tatctgatat ggtcatttgt    2880
tttaaataac acccacccct tattttccgt aaatacacac acaaaatgga tcgcatctgt    2940
gtgactaatg gtttatttgt attatatcat catcatcatc ctaaaattaa caacccagaa    3000
acaaaaatct ctatacagag atcaaattca cactcaatag tatgttctga atatatgttc    3060
aagagagagt ctctaaatca ctgttagtgt ggccaagagc agggttttct ttttgttctt    3120
agaactgctc ccatttctgg gaactaaaac cagtttatt tgccccaccc cttggagcca     3180
caaatgttta gaactcttca acttcggtaa tgaggaagaa ggagaaagag ctgggggaag    3240
ggcagaagac tggtttagga ggaaaaggaa ataaggagaa aagagaatgg gagagtgaga    3300
gaaaataaaa aaggcaaaag ggagagagag gggaaggggg tctcatattg gtcattccct    3360
gccccagatt tcttaaagtt tgatatgtat agaatataat tgaaggaggt atacacatat    3420
tgatgttgtt ttgattatct atggtattga atcttttaaa atctggtcac aaattttgat    3480 gctgagggg attattcaag ggactaggat gaactaaata agaactcagt tgttctttgt    3540
catactacta ttcctttcgt ctcccagaat cctcagggca ctgagggtag gtctgacaaa    3600
taaggcctgc tgtgcgaata tagccttct gaaatgtacc aggatggttt ctgcttagag     3660
acacttaggt ccagcctgtt cacactgcac ctcaggtatc aattcatcta ttcaacagat    3720
atttattgtg ttattactat gagtcaggct ctgtttattg tttcaattct ttacaccaaa    3780
gtatgaactg gagagggtac ctcagttata aggagtctga gaatattggc cctttctaac    3840
ctatgtgcat aattaaaacc agcttcattt gttgctccga gagtgtttct ccaaggtttt    3900
ctatcttcaa aaccaactaa gttatgaaag tagagagatc tgccctgtgt tatccagtta    3960
tgagataaaa aatgaatata agagtgcttg tcattataaa agtttccttt tttattctct    4020
caagccacca gctgccagcc accagcagcc agctgccagc ctagcttttt tttttttttt    4080
ttttttttag cacttagtat ttagcattta ttaacaggta ctctaagaat gatgaagcat    4140 tgttttaat cttaagacta tgaaggtttt tcttagttct tctgcttttg caattgtgtt      4200
tgtgaaattt gaatacttgc aggctttgta tgtgaataat tctagcgggg gacctgggag    4260
ataattccta cggggaattc ttaaaactgt gctcaactat taaaatgaat gagctttcaa    4320
aaaaaaaaaa aaaaaaaaaa aaaaaaaaaa aaa                                  4353

<210> SEQ ID NO 13
<211> LENGTH: 570
<212> TYPE: PRT
<213> ORGANISM: homo sapiens
<220> FEATURE:
<221> NAME/KEY: MISC_FEATURE
<223> OTHER INFORMATION: NP_000388 proteic sequence of the CYBB gene

<400> SEQUENCE: 13

Met Gly Asn Trp Ala Val Asn Glu Gly Leu Ser Ile Phe Val Ile Leu
1               5                   10                  15

Val Trp Leu Gly Leu Asn Val Phe Leu Phe Val Trp Tyr Tyr Arg Val
            20                  25                  30

Tyr Asp Ile Pro Pro Lys Phe Tyr Thr Arg Lys Leu Leu Gly Ser
        35                  40                  45

Ala Leu Ala Leu Ala Arg Ala Pro Ala Ala Cys Leu Asn Phe Asn Cys
    50                  55                  60

Met Leu Ile Leu Leu Pro Val Cys Arg Asn Leu Leu Ser Phe Leu Arg
65                  70                  75                  80
```

-continued

```
Gly Ser Ser Ala Cys Cys Ser Thr Arg Val Arg Arg Gln Leu Asp Arg
                85                  90                  95

Asn Leu Thr Phe His Lys Met Val Ala Trp Met Ile Ala Leu His Ser
                100                 105                 110

Ala Ile His Thr Ile Ala His Leu Phe Asn Val Glu Trp Cys Val Asn
                115                 120                 125

Ala Arg Val Asn Asn Ser Asp Pro Tyr Ser Val Ala Leu Ser Glu Leu
        130                 135                 140

Gly Asp Arg Gln Asn Glu Ser Tyr Leu Asn Phe Ala Arg Lys Arg Ile
145                 150                 155                 160

Lys Asn Pro Glu Gly Gly Leu Tyr Leu Ala Val Thr Leu Leu Ala Gly
                165                 170                 175

Ile Thr Gly Val Val Ile Thr Leu Cys Leu Ile Leu Ile Ile Thr Ser
                180                 185                 190

Ser Thr Lys Thr Ile Arg Arg Ser Tyr Phe Glu Val Phe Trp Tyr Thr
                195                 200                 205

His His Leu Phe Val Ile Phe Phe Ile Gly Leu Ala Ile His Gly Ala
        210                 215                 220

Glu Arg Ile Val Arg Gly Gln Thr Ala Glu Ser Leu Ala Val His Asn
225                 230                 235                 240

Ile Thr Val Cys Glu Gln Lys Ile Ser Glu Trp Gly Lys Ile Lys Glu
                245                 250                 255

Cys Pro Ile Pro Gln Phe Ala Gly Asn Pro Pro Met Thr Trp Lys Trp
                260                 265                 270

Ile Val Gly Pro Met Phe Leu Tyr Leu Cys Glu Arg Leu Val Arg Phe
                275                 280                 285

Trp Arg Ser Gln Gln Lys Val Val Ile Thr Lys Val Val Thr His Pro
        290                 295                 300

Phe Lys Thr Ile Glu Leu Gln Met Lys Lys Lys Gly Phe Lys Met Glu
305                 310                 315                 320

Val Gly Gln Tyr Ile Phe Val Lys Cys Pro Lys Val Ser Lys Leu Glu
                325                 330                 335

Trp His Pro Phe Thr Leu Thr Ser Ala Pro Glu Glu Asp Phe Phe Ser
                340                 345                 350

Ile His Ile Arg Ile Val Gly Asp Trp Thr Glu Gly Leu Phe Asn Ala
        355                 360                 365

Cys Gly Cys Asp Lys Gln Glu Phe Gln Asp Ala Trp Lys Leu Pro Lys
370                 375                 380

Ile Ala Val Asp Gly Pro Phe Gly Thr Ala Ser Glu Asp Val Phe Ser
385                 390                 395                 400

Tyr Glu Val Val Met Leu Val Gly Ala Gly Ile Gly Val Thr Pro Phe
                405                 410                 415

Ala Ser Ile Leu Lys Ser Val Trp Tyr Lys Tyr Cys Asn Asn Ala Thr
                420                 425                 430

Asn Leu Lys Leu Lys Lys Ile Tyr Phe Tyr Trp Leu Cys Arg Asp Thr
        435                 440                 445

His Ala Phe Glu Trp Phe Ala Asp Leu Leu Gln Leu Leu Glu Ser Gln
        450                 455                 460

Met Gln Glu Arg Asn Asn Ala Gly Phe Leu Ser Tyr Asn Ile Tyr Leu
465                 470                 475                 480

Thr Gly Trp Asp Glu Ser Gln Ala Asn His Phe Ala Val His His Asp
                485                 490                 495
```

-continued

```
Glu Glu Lys Asp Val Ile Thr Gly Leu Lys Gln Lys Thr Leu Tyr Gly
            500                 505                 510

Arg Pro Asn Trp Asp Asn Glu Phe Lys Thr Ile Ala Ser Gln His Pro
        515                 520                 525

Asn Thr Arg Ile Gly Val Phe Leu Cys Gly Pro Glu Ala Leu Ala Glu
    530                 535                 540

Thr Leu Ser Lys Gln Ser Ile Ser Asn Ser Glu Ser Gly Pro Arg Gly
545                 550                 555                 560

Val His Phe Ile Phe Asn Lys Glu Asn Phe
                565                 570

<210> SEQ ID NO 14
<211> LENGTH: 3056
<212> TYPE: PRT
<213> ORGANISM: homo sapiens
<220> FEATURE:
<221> NAME/KEY: MISC_FEATURE
<223> OTHER INFORMATION: ATM proteic sequence NP_00042

<400> SEQUENCE: 14

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
        275                 280                 285
```

-continued

```
Ile His His Pro Lys Gly Ala Lys Thr Gln Glu Lys Gly Ala Tyr Glu
    290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
        355                 360                 365

Ser Tyr Thr Thr Thr Gln Arg Glu Ser Ser Asp Tyr Ser Val Pro Cys
    370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
                405                 410                 415

Thr Gln Leu Ile Ser Lys Tyr Pro Ala Ser Leu Pro Asn Cys Glu Leu
            420                 425                 430

Ser Pro Leu Leu Met Ile Leu Ser Gln Leu Leu Pro Gln Gln Arg His
        435                 440                 445

Gly Glu Arg Thr Pro Tyr Val Leu Arg Cys Leu Thr Glu Val Ala Leu
    450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
            500                 505                 510

Gln Gly Ser Leu Val Glu Val Asp Arg Glu Phe Trp Lys Leu Phe Thr
        515                 520                 525

Gly Ser Ala Cys Arg Pro Ser Cys Pro Ala Val Cys Cys Leu Thr Leu
    530                 535                 540

Ala Leu Thr Thr Ser Ile Val Pro Gly Thr Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
            580                 585                 590

Thr Glu Val Pro Pro Ile Leu His Ser Asn Phe Pro His Leu Val Leu
        595                 600                 605

Glu Lys Ile Leu Val Ser Leu Thr Met Lys Asn Cys Lys Ala Ala Met
    610                 615                 620

Asn Phe Phe Gln Ser Val Pro Glu Cys Glu His His Gln Lys Asp Lys
625                 630                 635                 640

Glu Glu Leu Ser Phe Ser Glu Val Glu Glu Leu Phe Leu Gln Thr Thr
                645                 650                 655

Phe Asp Lys Met Asp Phe Leu Thr Ile Val Arg Glu Cys Gly Ile Glu
            660                 665                 670

Lys His Gln Ser Ser Ile Gly Phe Ser Val His Gln Asn Leu Lys Glu
        675                 680                 685

Ser Leu Asp Arg Cys Leu Leu Gly Leu Ser Glu Gln Leu Leu Asn Asn
    690                 695                 700
```

-continued

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
            725                 730                 735

Glu Glu Glu Ala Tyr Lys Ser Glu Leu Phe Gln Lys Ala Lys Ser Leu
        740                 745                 750

Met Gln Cys Ala Gly Glu Ser Ile Thr Leu Phe Lys Asn Lys Thr Asn
    755                 760                 765

Glu Glu Phe Arg Ile Gly Ser Leu Arg Asn Met Met Gln Leu Cys Thr
770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
            805                 810                 815

Asp Ile Cys Lys Ser Leu Ala Ser Phe Ile Lys Lys Pro Phe Asp Arg
        820                 825                 830

Gly Glu Val Glu Ser Met Glu Asp Thr Asn Gly Asn Leu Met Glu
    835                 840                 845

Val Glu Asp Gln Ser Ser Met Asn Leu Phe Asn Asp Tyr Pro Asp Ser
850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
            885                 890                 895

Phe Leu Asp Met Leu Lys Phe Leu Cys Leu Cys Val Thr Thr Ala Gln
        900                 905                 910

Thr Asn Thr Val Ser Phe Arg Ala Ala Asp Ile Arg Arg Lys Leu Leu
    915                 920                 925

Met Leu Ile Asp Ser Ser Thr Leu Glu Pro Thr Lys Ser Leu His Leu
930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
            965                 970                 975

Cys Ser Leu Tyr Arg Arg Asp Gln Asp Val Cys Lys Thr Ile Leu Asn
        980                 985                 990

His Val Leu His Val Val Lys Asn Leu Gly Gln Ser Asn Met Asp Ser
    995                 1000                1005

Glu Asn Thr Arg Asp Ala Gln Gly Gln Phe Leu Thr Val Ile Gly
1010                1015                1020

Ala Phe Trp His Leu Thr Lys Glu Arg Lys Tyr Ile Phe Ser Val
1025                1030                1035

Arg Met Ala Leu Val Asn Cys Leu Lys Thr Leu Glu Ala Asp
1040                1045                1050

Pro Tyr Ser Lys Trp Ala Ile Leu Asn Val Met Gly Lys Asp Phe
1055                1060                1065

Pro Val Asn Glu Val Phe Thr Gln Phe Leu Ala Asp Asn His His
1070                1075                1080

Gln Val Arg Met Leu Ala Ala Glu Ser Ile Asn Arg Leu Phe Gln
1085                1090                1095

Asp Thr Lys Gly Asp Ser Ser Arg Leu Leu Lys Ala Leu Pro Leu
1100                1105                1110

Lys Leu Gln Gln Thr Ala Phe Glu Asn Ala Tyr Leu Lys Ala Gln

```
              1115                1120                1125

Glu Gly Met Arg Glu Met Ser His Ser Ala Glu Asn Pro Glu Thr
              1130                1135            1140

Leu Asp Glu Ile Tyr Asn Arg Lys Ser Val Leu Leu Thr Leu Ile
              1145                1150            1155

Ala Val Val Leu Ser Cys Ser Pro Ile Cys Glu Lys Gln Ala Leu
              1160                1165            1170

Phe Ala Leu Cys Lys Ser Val Lys Glu Asn Gly Leu Glu Pro His
              1175                1180            1185

Leu Val Lys Lys Val Leu Glu Lys Val Ser Glu Thr Phe Gly Tyr
              1190                1195            1200

Arg Arg Leu Glu Asp Phe Met Ala Ser His Leu Asp Tyr Leu Val
              1205                1210            1215

Leu Glu Trp Leu Asn Leu Gln Asp Thr Glu Tyr Asn Leu Ser Ser
              1220                1225            1230

Phe Pro Phe Ile Leu Leu Asn Tyr Thr Asn Ile Glu Asp Phe Tyr
              1235                1240            1245

Arg Ser Cys Tyr Lys Val Leu Ile Pro His Leu Val Ile Arg Ser
              1250                1255            1260

His Phe Asp Glu Val Lys Ser Ile Ala Asn Gln Ile Gln Glu Asp
              1265                1270            1275

Trp Lys Ser Leu Leu Thr Asp Cys Phe Pro Lys Ile Leu Val Asn
              1280                1285            1290

Ile Leu Pro Tyr Phe Ala Tyr Glu Gly Thr Arg Asp Ser Gly Met
              1295                1300            1305

Ala Gln Gln Arg Glu Thr Ala Thr Lys Val Tyr Asp Met Leu Lys
              1310                1315            1320

Ser Glu Asn Leu Leu Gly Lys Gln Ile Asp His Leu Phe Ile Ser
              1325                1330            1335

Asn Leu Pro Glu Ile Val Val Glu Leu Leu Met Thr Leu His Glu
              1340                1345            1350

Pro Ala Asn Ser Ser Ala Ser Gln Ser Thr Asp Leu Cys Asp Phe
              1355                1360            1365

Ser Gly Asp Leu Asp Pro Ala Pro Asn Pro Pro His Phe Pro Ser
              1370                1375            1380

His Val Ile Lys Ala Thr Phe Ala Tyr Ile Ser Asn Cys His Lys
              1385                1390            1395

Thr Lys Leu Lys Ser Ile Leu Glu Ile Leu Ser Lys Ser Pro Asp
              1400                1405            1410

Ser Tyr Gln Lys Ile Leu Leu Ala Ile Cys Glu Gln Ala Ala Glu
              1415                1420            1425

Thr Asn Asn Val Tyr Lys Lys His Arg Ile Leu Lys Ile Tyr His
              1430                1435            1440

Leu Phe Val Ser Leu Leu Leu Lys Asp Ile Lys Ser Gly Leu Gly
              1445                1450            1455

Gly Ala Trp Ala Phe Val Leu Arg Asp Val Ile Tyr Thr Leu Ile
              1460                1465            1470

His Tyr Ile Asn Gln Arg Pro Ser Cys Ile Met Asp Val Ser Leu
              1475                1480            1485

Arg Ser Phe Ser Leu Cys Cys Asp Leu Leu Ser Gln Val Cys Gln
              1490                1495            1500

Thr Ala Val Thr Tyr Cys Lys Asp Ala Leu Glu Asn His Leu His
              1505                1510            1515
```

-continued

Val Ile Val Gly Thr Leu Ile Pro Leu Val Tyr Glu Gln Val Glu
1520                1525                1530

Val Gln Lys Gln Val Leu Asp Leu Leu Lys Tyr Leu Val Ile Asp
1535                1540                1545

Asn Lys Asp Asn Glu Asn Leu Tyr Ile Thr Ile Lys Leu Leu Asp
1550                1555                1560

Pro Phe Pro Asp His Val Val Phe Lys Asp Leu Arg Ile Thr Gln
1565                1570                1575

Gln Lys Ile Lys Tyr Ser Arg Gly Pro Phe Ser Leu Leu Glu Glu
1580                1585                1590

Ile Asn His Phe Leu Ser Val Ser Val Tyr Asp Ala Leu Pro Leu
1595                1600                1605

Thr Arg Leu Glu Gly Leu Lys Asp Leu Arg Arg Gln Leu Glu Leu
1610                1615                1620

His Lys Asp Gln Met Val Asp Ile Met Arg Ala Ser Gln Asp Asn
1625                1630                1635

Pro Gln Asp Gly Ile Met Val Lys Leu Val Val Asn Leu Leu Gln
1640                1645                1650

Leu Ser Lys Met Ala Ile Asn His Thr Gly Glu Lys Glu Val Leu
1655                1660                1665

Glu Ala Val Gly Ser Cys Leu Gly Glu Val Gly Pro Ile Asp Phe
1670                1675                1680

Ser Thr Ile Ala Ile Gln His Ser Lys Asp Ala Ser Tyr Thr Lys
1685                1690                1695

Ala Leu Lys Leu Phe Glu Asp Lys Glu Leu Gln Trp Thr Phe Ile
1700                1705                1710

Met Leu Thr Tyr Leu Asn Asn Thr Leu Val Glu Asp Cys Val Lys
1715                1720                1725

Val Arg Ser Ala Ala Val Thr Cys Leu Lys Asn Ile Leu Ala Thr
1730                1735                1740

Lys Thr Gly His Ser Phe Trp Glu Ile Tyr Lys Met Thr Thr Asp
1745                1750                1755

Pro Met Leu Ala Tyr Leu Gln Pro Phe Arg Thr Ser Arg Lys Lys
1760                1765                1770

Phe Leu Glu Val Pro Arg Phe Asp Lys Glu Asn Pro Phe Glu Gly
1775                1780                1785

Leu Asp Asp Ile Asn Leu Trp Ile Pro Leu Ser Glu Asn His Asp
1790                1795                1800

Ile Trp Ile Lys Thr Leu Thr Cys Ala Phe Leu Asp Ser Gly Gly
1805                1810                1815

Thr Lys Cys Glu Ile Leu Gln Leu Leu Lys Pro Met Cys Glu Val
1820                1825                1830

Lys Thr Asp Phe Cys Gln Thr Val Leu Pro Tyr Leu Ile His Asp
1835                1840                1845

Ile Leu Leu Gln Asp Thr Asn Glu Ser Trp Arg Asn Leu Leu Ser
1850                1855                1860

Thr His Val Gln Gly Phe Phe Thr Ser Cys Leu Arg His Phe Ser
1865                1870                1875

Gln Thr Ser Arg Ser Thr Thr Pro Ala Asn Leu Asp Ser Glu Ser
1880                1885                1890

Glu His Phe Phe Arg Cys Cys Leu Asp Lys Lys Ser Gln Arg Thr
1895                1900                1905

```
Met Leu Ala Val Val Asp Tyr Met Arg Arg Gln Lys Arg Pro Ser
    1910                1915                1920

Ser Gly Thr Ile Phe Asn Asp Ala Phe Trp Leu Asp Leu Asn Tyr
    1925                1930                1935

Leu Glu Val Ala Lys Val Ala Gln Ser Cys Ala Ala His Phe Thr
    1940                1945                1950

Ala Leu Leu Tyr Ala Glu Ile Tyr Ala Asp Lys Lys Ser Met Asp
    1955                1960                1965

Asp Gln Glu Lys Arg Ser Leu Ala Phe Glu Glu Gly Ser Gln Ser
    1970                1975                1980

Thr Thr Ile Ser Ser Leu Ser Glu Lys Ser Lys Glu Glu Thr Gly
    1985                1990                1995

Ile Ser Leu Gln Asp Leu Leu Leu Glu Ile Tyr Arg Ser Ile Gly
    2000                2005                2010

Glu Pro Asp Ser Leu Tyr Gly Cys Gly Gly Gly Lys Met Leu Gln
    2015                2020                2025

Pro Ile Thr Arg Leu Arg Thr Tyr Glu His Glu Ala Met Trp Gly
    2030                2035                2040

Lys Ala Leu Val Thr Tyr Asp Leu Glu Thr Ala Ile Pro Ser Ser
    2045                2050                2055

Thr Arg Gln Ala Gly Ile Ile Gln Ala Leu Gln Asn Leu Gly Leu
    2060                2065                2070

Cys His Ile Leu Ser Val Tyr Leu Lys Gly Leu Asp Tyr Glu Asn
    2075                2080                2085

Lys Asp Trp Cys Pro Glu Leu Glu Glu Leu His Tyr Gln Ala Ala
    2090                2095                2100

Trp Arg Asn Met Gln Trp Asp His Cys Thr Ser Val Ser Lys Glu
    2105                2110                2115

Val Glu Gly Thr Ser Tyr His Glu Ser Leu Tyr Asn Ala Leu Gln
    2120                2125                2130

Ser Leu Arg Asp Arg Glu Phe Ser Thr Phe Tyr Glu Ser Leu Lys
    2135                2140                2145

Tyr Ala Arg Val Lys Glu Val Glu Glu Met Cys Lys Arg Ser Leu
    2150                2155                2160

Glu Ser Val Tyr Ser Leu Tyr Pro Thr Leu Ser Arg Leu Gln Ala
    2165                2170                2175

Ile Gly Glu Leu Glu Ser Ile Gly Glu Leu Phe Ser Arg Ser Val
    2180                2185                2190

Thr His Arg Gln Leu Ser Glu Val Tyr Ile Lys Trp Gln Lys His
    2195                2200                2205

Ser Gln Leu Leu Lys Asp Ser Asp Phe Ser Phe Gln Glu Pro Ile
    2210                2215                2220

Met Ala Leu Arg Thr Val Ile Leu Glu Ile Leu Met Glu Lys Glu
    2225                2230                2235

Met Asp Asn Ser Gln Arg Glu Cys Ile Lys Asp Ile Leu Thr Lys
    2240                2245                2250

His Leu Val Glu Leu Ser Ile Leu Ala Arg Thr Phe Lys Asn Thr
    2255                2260                2265

Gln Leu Pro Glu Arg Ala Ile Phe Gln Ile Lys Gln Tyr Asn Ser
    2270                2275                2280

Val Ser Cys Gly Val Ser Glu Trp Gln Leu Glu Glu Ala Gln Val
    2285                2290                2295

Phe Trp Ala Lys Lys Glu Gln Ser Leu Ala Leu Ser Ile Leu Lys
```

-continued

```
            2300                2305                2310
Gln Met Ile Lys Lys Leu Asp Ala Ser Cys Ala Ala Asn Asn Pro
        2315                2320                2325
Ser Leu Lys Leu Thr Tyr Thr Glu Cys Leu Arg Val Cys Gly Asn
        2330                2335                2340
Trp Leu Ala Glu Thr Cys Leu Glu Asn Pro Ala Val Ile Met Gln
        2345                2350                2355
Thr Tyr Leu Glu Lys Ala Val Glu Val Ala Gly Asn Tyr Asp Gly
        2360                2365                2370
Glu Ser Ser Asp Glu Leu Arg Asn Gly Lys Met Lys Ala Phe Leu
        2375                2380                2385
Ser Leu Ala Arg Phe Ser Asp Thr Gln Tyr Gln Arg Ile Glu Asn
        2390                2395                2400
Tyr Met Lys Ser Ser Glu Phe Glu Asn Lys Gln Ala Leu Leu Lys
        2405                2410                2415
Arg Ala Lys Glu Glu Val Gly Leu Leu Arg Glu His Lys Ile Gln
        2420                2425                2430
Thr Asn Arg Tyr Thr Val Lys Val Gln Arg Glu Leu Glu Leu Asp
        2435                2440                2445
Glu Leu Ala Leu Arg Ala Leu Lys Glu Asp Arg Lys Arg Phe Leu
        2450                2455                2460
Cys Lys Ala Val Glu Asn Tyr Ile Asn Cys Leu Leu Ser Gly Glu
        2465                2470                2475
Glu His Asp Met Trp Val Phe Arg Leu Cys Ser Leu Trp Leu Glu
        2480                2485                2490
Asn Ser Gly Val Ser Glu Val Asn Gly Met Met Lys Arg Asp Gly
        2495                2500                2505
Met Lys Ile Pro Thr Tyr Lys Phe Leu Pro Leu Met Tyr Gln Leu
        2510                2515                2520
Ala Ala Arg Met Gly Thr Lys Met Met Gly Gly Leu Gly Phe His
        2525                2530                2535
Glu Val Leu Asn Asn Leu Ile Ser Arg Ile Ser Met Asp His Pro
        2540                2545                2550
His His Thr Leu Phe Ile Ile Leu Ala Leu Ala Asn Ala Asn Arg
        2555                2560                2565
Asp Glu Phe Leu Thr Lys Pro Glu Val Ala Arg Arg Ser Arg Ile
        2570                2575                2580
Thr Lys Asn Val Pro Lys Gln Ser Ser Gln Leu Asp Glu Asp Arg
        2585                2590                2595
Thr Glu Ala Ala Asn Arg Ile Ile Cys Thr Ile Arg Ser Arg Arg
        2600                2605                2610
Pro Gln Met Val Arg Ser Val Glu Ala Leu Cys Asp Ala Tyr Ile
        2615                2620                2625
Ile Leu Ala Asn Leu Asp Ala Thr Gln Trp Lys Thr Gln Arg Lys
        2630                2635                2640
Gly Ile Asn Ile Pro Ala Asp Gln Pro Ile Thr Lys Leu Lys Asn
        2645                2650                2655
Leu Glu Asp Val Val Val Pro Thr Met Glu Ile Lys Val Asp His
        2660                2665                2670
Thr Gly Glu Tyr Gly Asn Leu Val Thr Ile Gln Ser Phe Lys Ala
        2675                2680                2685
Glu Phe Arg Leu Ala Gly Gly Val Asn Leu Pro Lys Ile Ile Asp
        2690                2695                2700
```

```
Cys Val Gly Ser Asp Gly Lys Glu Arg Arg Gln Leu Val Lys Gly
2705                2710                2715

Arg Asp Asp Leu Arg Gln Asp Ala Val Met Gln Gln Val Phe Gln
2720                2725                2730

Met Cys Asn Thr Leu Leu Gln Arg Asn Thr Glu Thr Arg Lys Arg
2735                2740                2745

Lys Leu Thr Ile Cys Thr Tyr Lys Val Val Pro Leu Ser Gln Arg
2750                2755                2760

Ser Gly Val Leu Glu Trp Cys Thr Gly Thr Val Pro Ile Gly Glu
2765                2770                2775

Phe Leu Val Asn Asn Glu Asp Gly Ala His Lys Arg Tyr Arg Pro
2780                2785                2790

Asn Asp Phe Ser Ala Phe Gln Cys Gln Lys Lys Met Met Glu Val
2795                2800                2805

Gln Lys Lys Ser Phe Glu Glu Lys Tyr Glu Val Phe Met Asp Val
2810                2815                2820

Cys Gln Asn Phe Gln Pro Val Phe Arg Tyr Phe Cys Met Glu Lys
2825                2830                2835

Phe Leu Asp Pro Ala Ile Trp Phe Glu Lys Arg Leu Ala Tyr Thr
2840                2845                2850

Arg Ser Val Ala Thr Ser Ser Ile Val Gly Tyr Ile Leu Gly Leu
2855                2860                2865

Gly Asp Arg His Val Gln Asn Ile Leu Ile Asn Glu Gln Ser Ala
2870                2875                2880

Glu Leu Val His Ile Asp Leu Gly Val Ala Phe Glu Gln Gly Lys
2885                2890                2895

Ile Leu Pro Thr Pro Glu Thr Val Pro Phe Arg Leu Thr Arg Asp
2900                2905                2910

Ile Val Asp Gly Met Gly Ile Thr Gly Val Glu Gly Val Phe Arg
2915                2920                2925

Arg Cys Cys Glu Lys Thr Met Glu Val Met Arg Asn Ser Gln Glu
2930                2935                2940

Thr Leu Leu Thr Ile Val Glu Val Leu Leu Tyr Asp Pro Leu Phe
2945                2950                2955

Asp Trp Thr Met Asn Pro Leu Lys Ala Leu Tyr Leu Gln Gln Arg
2960                2965                2970

Pro Glu Asp Glu Thr Glu Leu His Pro Thr Leu Asn Ala Asp Asp
2975                2980                2985

Gln Glu Cys Lys Arg Asn Leu Ser Asp Ile Asp Gln Ser Phe Asn
2990                2995                3000

Lys Val Ala Glu Arg Val Leu Met Arg Leu Gln Glu Lys Leu Lys
3005                3010                3015

Gly Val Glu Glu Gly Thr Val Leu Ser Val Gly Gly Gln Val Asn
3020                3025                3030

Leu Leu Ile Gln Gln Ala Ile Asp Pro Lys Asn Leu Ser Arg Leu
3035                3040                3045

Phe Pro Gly Trp Lys Ala Trp Val
3050                3055
```

<210> SEQ ID NO 15
<211> LENGTH: 13147
<212> TYPE: DNA
<213> ORGANISM: homo sapiens
<220> FEATURE:

<221> NAME/KEY: misc_feature
<223> OTHER INFORMATION: ATM mRNA NM_00051

<400> SEQUENCE: 15

```
ccggagcccg agccgaaggg cgagccgcaa acgctaagtc gctggccatt ggtggacatg      60
gcgcaggcgc gtttgctccg acgggccgaa tgttttgggg cagtgttttg agcgcggaga     120
ccgcgtgata ctggatgcgc atgggcatac cgtgctctgc ggctgcttgg cgttgcttct     180
tcctccagaa gtgggcgctg gcagtcacg cagggtttga accggaagcg ggagtaggta     240
gctgcgtggc taacggagaa aagaagccgt ggccgcggga ggaggcgaga ggagtcggga     300
tctgcgctgc agccaccgcc gcggttgata ctactttgac cttccgagtg cagtgacagt     360
gatgtgtgtt ctgaaattgt gaaccatgag tctagtactt aatgatctgc ttatctgctg     420
ccgtcaacta gaacatgata gagctacaga acgaaagaaa gaagttgaga aatttaagcg     480
cctgattcga gatcctgaaa caattaaaca tctagatcgg cattcagatt ccaaacaagg     540
aaaatatttg aattgggatg ctgttttag attttacag aaatatattc agaaagaaac     600
agaatgtctg agaatagcaa aaccaaatgt atcagcctca acacaagcct ccaggcagaa     660
aaagatgcag gaaatcagta gtttggtcaa atacttcatc aaatgtgcaa acagaagagc     720
acctaggcta aaatgtcaag aactcttaaa ttatatcatg gatacagtga aagattcatc     780
taatggtgct atttacggag ctgattgtag caacatacta ctcaaagaca ttcttttctgt     840
gagaaaatac tggtgtgaaa tatctcagca acagtggtta gaattgttct ctgtgtactt     900
caggctctat ctgaaacctt cacaagatgt tcatagagtt ttagtggcta gaataattca     960
tgctgttacc aaaggatgct gttctcagac tgacggatta aattccaaat ttttggactt    1020
ttttccaag gctattcagt gtgcgagaca agaaaagagc tcttcaggtc taaatcatat    1080
cttagcagct cttactatct tcctcaagac tttggctgtc aactttcgaa ttcgagtgtg    1140
tgaattagga gatgaaattc ttcccacttt gctttatatt tggactcaac ataggcttaa    1200
tgattcttta aaagaagtca ttattgaatt atttcaactg caaatttata tccatcatcc    1260
gaaaggagcc aaaacccaag aaaaaggtgc ttatgaatca acaaaatgga gaagtatttt    1320
atacaactta tatgatctgc tagtgaatga gataagtcat ataggaagta gaggaaagta    1380
ttcttcagga tttcgtaata ttgccgtcaa agaaaatttg attgaattga tggcagatat    1440
ctgtcaccag gtttttaatg aagataccag atccttggag atttctcaat cttacactac    1500
tacacaaaga gaatctagtg attacagtgt cccttgcaaa aggaagaaaa tagaactagg    1560
ctgggaagta ataaaagatc accttcagaa gtcacagaat gattttgatc ttgtgccttg    1620
gctacagatt gcaacccaat taatatcaaa gtatcctgca agtttaccta actgtgagct    1680
gtctccatta ctgatgatac tatctcagct tctaccccaa cagcgacatg ggaacgtac    1740
accatatgtg ttacgatgcc ttacggaagt tgcattgtgt caagacaaga ggtcaaacct    1800
agaaagctca caaagtcag atttattaaa actctggaat aaaatttggt gtattacctt    1860
tcgtggtata agttctgagc aaatacaagc tgaaaacttt ggcttacttg gagccataat    1920
tcagggtagt ttagttgagg ttgacagaga attctggaag ttatttactg gtcagcctg    1980
cagaccttca tgtcctgcag tatgctgttt gactttggca ctgaccacca gtatagttcc    2040
aggaacggta aaaatgggaa tagagcaaaa tatgtgtgaa gtaaatagaa gcttttcttt    2100
aaaggaatca ataatgaaat ggctcttatt ctatcagtta gagggtgact tagaaaatag    2160
cacagaagtg cctccaattc ttcacagtaa ttttcctcat cttgtactgg agaaaattct    2220
```

```
tgtgagtctc actatgaaaa actgtaaagc tgcaatgaat ttttccaaa gcgtgccaga    2280 atgtgaacac caccaaaaag ataaagaaga actttcattc tcagaagtag aagaactatt    2340
tcttcagaca acttttgaca agatggactt tttaaccatt gtgagagaat gtggtataga    2400
aaagcaccag tccagtattg gcttctctgt ccaccagaat ctcaaggaat cactggatcg    2460
ctgtcttctg ggattatcag aacagcttct gaataattac tcatctgaga ttacaaattc    2520
agaaactctt gtccggtgtt cacgtctttt ggtgggtgtc cttggctgct actgttacat    2580
gggtgtaata gctgaagagg aagcatataa gtcagaatta ttccagaaag ccaagtctct    2640
aatgcaatgt gcaggagaaa gtatcactct gtttaaaaat aagacaaatg aggaattcag    2700
aattggttcc ttgagaaata tgatgcagct atgtacacgt tgcttgagca actgtaccaa    2760
gaagagtcca ataagattg catctggctt tttcctgcga ttgttaacat caaagctaat    2820
gaatgacatt gcagatattt gtaaaagttt agcatccttc atcaaaaagc catttgaccg    2880
tggagaagta gaatcaatgg aagatgatac taatggaaat ctaatggagg tggaggatca    2940
gtcatccatg aatctattta cgattaccc tgatagtagt gttagtgatg caaacgaacc    3000
tggagagagc caaagtacca taggtgccat taatcctttta gctgaagaat atctgtcaaa    3060
gcaagatcta cttttcttag acatgctcaa gttcttgtgt ttgtgtgtaa ctactgctca    3120
gaccaatact gtgtccttta gggcagctga tattcggagg aaattgttaa tgttaattga    3180
ttctagcacg ctagaaccta ccaaatccct ccacctgcat atgtatctaa tgcttttaaa    3240
ggagcttcct ggagaagagt acccttgcc aatggaagat gttcttgaac ttctgaaacc    3300
actatccaat gtgtgttctt tgtatcgtcg tgaccaagat gtttgtaaaa ctattttaaa    3360
ccatgtcctt catgtagtga aaaacctagg tcaaagcaat atggactctg agaacacaag    3420
ggatgctcaa ggacagtttc ttacagtaat tggagcattt tggcatctaa caaaggagag    3480
gaaatatata ttctctgtaa aatggcccct agtaaattgc cttaaaactt tgcttgaggc    3540
tgatccttat tcaaaatggg ccattcttaa tgtaatggga aaagactttc ctgtaaatga    3600
agtatttaca caatttcttg ctgacaatca tcaccaagtt cgcatgttgg ctgcagagtc    3660
aatcaataga ttgttccagg acacgaaggg agattcttcc aggttactga agcacttcc    3720 tttgaagctt cagcaaacag cttttgaaaa tgcatacttg aaagctcagg aaggaatgag    3780
agaaatgtcc catagtgctg agaaccctga actttggat gaaatttata atagaaaatc    3840
tgttttactg acgttgatag ctgtggtttt atcctgtagc cctatctgcg aaaaacaggc    3900
tttgtttgcc ctgtgtaaat ctgtgaaaga gaatggatta gaacctcacc ttgtgaaaaa    3960
ggttttagag aaagtttctg aaacttttgg atatagacgt ttagaagact ttatggcatc    4020
tcatttagat tatctggttt tggaatggct aaatcttcaa gatactgaat acaacttatc    4080 ttctttttcct tttatttat taaactacac aaatattgag gatttctata gatcttgtta    4140
taaggttttg attccacatc tggtgattag aagtcatttt gatgaggtga agtccattgc    4200
taatcagatt caagaggact ggaaaagtct tctaacagac tgctttccaa agattcttgt    4260
aaatattctt ccttatttg cctatgaggg taccagagac agtgggatgg cacagcaaag    4320
agagactgct accaaggtct atgatatgct taaagtgaa aacttattgg gaaaacagat    4380
tgatcactta ttcattagta atttaccaga gattgtggtg gagttattga tgacgttaca    4440
tgagccagca aattctagtg ccagtcagag cactgacctc tgtgacttt caggggattt    4500 ggatcctgct cctaatccac ctcatttcc atcgcatgtg attaaagcaa catttgccta    4560
tatcagcaat tgtcataaaa ccaagttaaa aagcatttta gaaattcttt ccaaaagccc    4620
```

```
tgattcctat cagaaaattc ttcttgccat atgtgagcaa gcagctgaaa caaataatgt    4680
ttataagaag cacagaattc ttaaaatata tcacctgttt gttagtttat tactgaaaga    4740
tataaaaagt ggcttaggag gagcttgggc ctttgttctt cgagacgtta tttatacttt    4800
gattcactat atcaaccaaa ggccttcttg tatcatggat gtgtcattac gtagcttctc    4860
cctttgttgt gacttattaa gtcaggtttg ccagacagcc gtgacttact gtaaggatgc    4920
tctagaaaac catcttcatg ttattgttgg tacacttata ccccttgtgt atgagcaggt    4980
ggaggttcag aaacaggtat tggacttgtt gaaatactta gtgatagata caaggataa    5040 tgaaacctc tatatcacga ttaagctttt agatccttt cctgaccatg ttgtttttaa    5100
ggatttgcgt attactcagc aaaaaatcaa atacagtaga ggaccctttt cactcttgga    5160
ggaaattaac cattttctct cagtaagtgt ttatgatgca cttccattga caagacttga    5220
aggactaaag gatcttcgaa gacaactgga actacataaa gatcagatgg tggacattat    5280
gagagcttct caggataatc cgcaagatgg gattatggtg aaactagttg tcaatttgtt    5340
gcagttatcc aagatggcaa taaaccacac tggtgaaaaa gaagttctag aggctgttgg    5400
aagctgcttg ggagaagtgg gtcctataga tttctctacc atagctatac aacatagtaa    5460
agatgcatct tataccaagg cccttaagtt atttgaagat aaagaacttc agtggacctt    5520
cataatgctg acctacctga ataacacact ggtagaagat tgtgtcaaag ttcgatcagc    5580
agctgttacc tgtttgaaaa acattttagc cacaaagact ggacatagtt tctgggagat    5640
ttataagatg acaacagatc caatgctggc ctatctacag cctttagaa catcaagaaa    5700 aaagttttta gaagtaccca gatttgacaa agaaaaccct tttgaaggcc tggatgatat    5760
aaatctgtgg attcctctaa gtgaaaatca tgacatttgg ataaagacac tgacttgtgc    5820 tttttggac agtggaggca caaatgtga aattcttcaa ttattaaagc caatgtgtga    5880
agtgaaaact gacttttgtc agactgtact tccatacttg attcatgata ttttactcca    5940
agatacaaat gaatcatgga gaaatctgct ttctacacat gttcagggat ttttcaccag    6000
ctgtcttcga cacttctcgc aaacgagccg atccacaacc cctgcaaact tggattcaga    6060
gtcagagcac tttttccgat gctgtttgga taaaaaatca caaagaacaa tgcttgctgt    6120
tgtggactac atgagaagac aaaagagacc ttcttcagga acaattttta atgatgcttt    6180
ctggctggat ttaaattatc tagaagttgc caaggtagct cagtcttgtg ctgctcactt    6240
tacagcttta ctctatgcag aaatctatgc agataagaaa agtatggatg atcaagagaa    6300
aagaagtctt gcatttgaag aaggaagcca gagtacaact atttctagct tgagtgaaaa    6360
aagtaaagaa gaaactggaa taagtttaca ggatcttctc ttagaaatct acagaagtat    6420 agggggagcca gatagtttgt atggctgtgg tggagggaag atgttacaac ccattactag    6480
actacgaaca tatgaacacg aagcaatgtg gggcaaagcc ctagtaacat atgacctcga    6540
aacagcaatc ccctcatcaa cacgccaggc aggaatcatt caggccttgc agaatttggg    6600
actctgccat attctttccg tctatttaaa aggattggat tatgaaaata agactggtg    6660 tcctgaacta gaagaacttc attaccaagc agcatggagg aatatgcagt gggaccattg    6720
cacttccgtc agcaaagaag tagaaggaac cagttaccat gaatcattgt acaatgctct    6780
acaatctcta agagacagag aattctctac attttatgaa agtctcaaat atgccagagt    6840
aaaagaagtg gaagagatgt gtaagcgcag ccttgagtct gtgtattcgc tctatcccac    6900
acttagcagg ttgcaggcca ttggagagct ggaaagcatt ggggagcttt tctcaagatc    6960
```

```
agtcacacat agacaactct ctgaagtata tattaagtgg cagaaacact cccagcttct    7020
caaggacagt gattttagtt ttcaggagcc tatcatggct ctacgcacag tcattttgga    7080
gatcctgatg gaaaaggaaa tggacaactc acaaagagaa tgtattaagg acattctcac    7140
caaacacctt gtagaactct ctatactggc cagaactttc aagaacactc agctccctga    7200
aagggcaata tttcaaatta aacagtacaa ttcagttagc tgtggagtct ctgagtggca    7260
gctggaagaa gcacaagtat tctgggcaaa aaaggagcag agtcttgccc tgagtattct    7320
caagcaaatg atcaagaagt tggatgccag ctgtgcagcg aacaatccca gcctaaaact    7380
tacatacaca gaatgtctga gggtttgtgg caactggtta gcagaaacgt gcttagaaaa    7440
tcctgcggtc atcatgcaga cctatctaga aaaggcagta gaagttgctg aaattatga    7500 tggagaaagt agtgatgagc taagaaatgg aaaaatgaag gcatttctct cattagcccg    7560
gttttcagat actcaatacc aaagaattga aaactacatg aaatcatcgg aatttgaaaa    7620
caagcaagct ctcctgaaaa gagccaaaga ggaagtaggt ctccttaggg aacataaaat    7680
tcagacaaac agatacacag taaaggttca gcgagagctg gagttggatg aattagccct    7740
gcgtgcactg aaagaggatc gtaaacgctt cttatgtaaa gcagttgaaa attatatcaa    7800
ctgcttatta agtggagaag aacatgatat gtgggtattc cgactttgtt ccctctggct    7860
tgaaaattct ggagtttctg aagtcaatgg catgatgaag agagacggaa tgaagattcc    7920
aacatataaa tttttgcctc ttatgtacca attggctgct agaatgggga ccaagatgat    7980
gggaggccta ggatttcatg aagtcctcaa taatctaatc tctagaattt caatggatca    8040
cccccatcac actttgttta ttatactggc cttagcaaat gcaaacagag atgaatttct    8100
gactaaacca gaggtagcca gaagaagcag aataactaaa aatgtgccta acaaagctc    8160 tcagcttgat gaggatcgaa cagaggctgc aaatagaata atatgtacta tcagaagtag    8220
gagacctcag atggtcagaa gtgttgaggc actttgtgat gcttatatta tattagcaaa    8280
cttagatgcc actcagtgga agactcagag aaaaggcata aatattccag cagaccagcc    8340
aattactaaa cttaagaatt tagaagatgt tgttgtccct actatggaaa ttaaggtgga    8400
ccacacagga gaatatggaa atctggtgac tatacagtca tttaaagcag aatttcgctt    8460
agcaggaggt gtaaatttac caaaaataat agattgtgta ggttccgatg caaggagag    8520 gagacagctt gttaagggcc gtgatgacct gagacaagat gctgtcatgc aacaggtctt    8580
ccagatgtgt aatacattac tgcagagaaa cacggaaact aggaagagga aattaactat    8640 ctgtactat aaggtggttc ccctctctca gcgaagtggg gttcttgaat ggtgcacagg    8700
aactgtcccc attggtgaat tcttgttaa caatgaagat ggtgctcata aaagatacag    8760
gccaaatgat ttcagtgcct ttcagtgcca aagaaaatg atggaggtgc aaaaaaagtc    8820
ttttgaagag aaatatgaag tcttcatgga tgtttgccaa aattttcaac cagttttccg    8880
ttacttctgc atggaaaaat tcttggatcc agctatttgg tttgagaagc gattggctta    8940
tacgcgcagt gtagctactt cttctattgt tggttacata cttggacttg gtgatagaca    9000
tgtacagaat atcttgataa atgagcagtc agcagaactt gtacatatag atctaggtgt    9060
tgcttttgaa cagggcaaaa tccttcctac tcctgagaca gttcctttta gactcaccag    9120
agatattgtg gatggcatgg gcattacggg tgttgaaggt gtcttcagaa gatgctgtga    9180 gaaaccatg gaagtgatga aaactctctg gaaactctg ttaaccattg tagaggtcct    9240
tctatatgat ccactctttg actggaccat gaatcctttg aaagctttgt atttacagca    9300
gaggccggaa gatgaaactg agcttcaccc tactctgaat gcagatgacc aagaatgcaa    9360
```

```
acgaaatctc agtgatattg accagagttt caacaaagta gctgaacgtg tcttaatgag    9420
actacaagag aaactgaaag gagtggaaga aggcactgtg ctcagtgttg gtggacaagt    9480
gaatttgctc atacagcagg ccatagaccc caaaaatctc agccgacttt tcccaggatg    9540
gaaagcttgg gtgtgatctt cagtatatga attacccttt cattcagcct ttagaaatta    9600
tattttagcc tttattttta acctgccaac atactttaag tagggattaa tatttaagtg    9660
aactattgtg ggttttttg aatgttggtt ttaatacttg atttaatcac cactcaaaaa    9720
tgttttgatg gtcttaagga acatctctgc tttcactctt tagaaataat ggtcattcgg    9780
gctgggcgca gcggctcacg cctgtaatcc cagcactttg ggaggccgag gtgagcggat    9840
cacaaggtca ggagttcgag accagcctgg ccaagagacc agcctggcca gtatggtgaa    9900
accctgtctc tactaaaaat acaaaaatta gccgagcatg gtggcgggca cctgtaatcc    9960
cagctactcg agaggctgag gcaggagaat ctcttgaacc tgggaggtga aggttgctgt   10020
gggccaaaat catgccattg cactccagcc tgggtgacaa gagcgaaact ccatctcaaa   10080
aaaaaaaaaa aaaaaacaga aacgtatttg gattttttcct agtaagatca ctcagtgtta   10140
ctaaataatg aagttgttat ggagaacaaa tttcaaagac acagttagtg tagttactat   10200 tttttttaagt gtgtattaaa acttctcatt ctattctctt tatcttttaa gcccttctgt   10260
actgtccatg tatgttatct ttctgtgata acttcataga ttgccttcta gttcatgaat   10320
tctcttgtca gatgtatata atctctttta ccctatccat tgggcttctt ctttcagaaa   10380
ttgtttttca tttctaatta tgcatcattt ttcagatctc tgtttcttga tgtcatttt    10440 aatgttttt taatgttttt tatgtcacta attatttaa atgtctgtac ttgatagaca    10500
ctgtaatagt tctattaaat ttagttcctg ctgtttatat ctgttgattt ttgtatttga   10560
taggctgttc atccagtttt gtcttttga aaagtgagtt tattttcagc aaggctttat    10620
ctatgggaat cttgagtgtc tgtttatgtc atattcccag ggctgttgct gcacacaagc    10680
ccattcttat tttaatttct tggctttagg gtttccatac ctgaagtgta gcataaatac    10740
tgataggaga tttcccaggc caaggcaaac acacttcctc ctcatctcct tgtgctagtg    10800
ggcagaatat ttgattgatg cctttttcac tgagagtata agcttccatg tgtcccacct    10860
ttatggcagg ggtggaagga ggtacattta attcccactg cctgcctttg caagccctg    10920 ggttctttgc tccccatata gatgtctaag ctaaaagccg tgggttaatg agactggcaa   10980
attgttccag gacagctaca gcatcagctc acatattcac ctctctggtt tttcattccc   11040
ctcatttttt tctgagacag agtccttgctc tgtcacccag gctggagtgc agtggcatga   11100
tctcagctca ctgaaacctc tgcctcctgg gttcaagcaa ttctcctgcc tcagcctccc   11160
gagtagctgg gactacaggc gtgtgccaac acgcccggct aatttttttgt atttttatta   11220 gagacggagt ttcaccgtgt tagccaggat ggtctcgatc gcttgacctc gtgatccacc   11280
ctcctcggcc tcccaaagtg ctgggattac aggtgtgagc caccgcgccc ggcctcattc    11340
ccctcatttt tgaccgtaag gatttcccct ttcttgtaag ttctgctatg tatttaaaag   11400
aatgttttct acatttatc cagcatttct ctgtgttctg ttggaaggga agggcttagg    11460
tatctagttt gatacatagg tagaagtgga acatttctct gtccccagc tgtcatcata    11520 taagataaac atcagataaa aagccacctg aaagtaaaac tactgactcg tgtattagtg   11580
agtataatct cttctccatc cttaggaaaa tgttcatccc agctgcggag attaacaaat    11640
gggtgattga gctttctcct cgtatttgga ccttgaaggt tatataaatt tttttcttat    11700
```

| | |
|---|---|
| gaagagttgg catttctttt tattgccaat ggcaggcact cattcatatt tgatctcctc | 11760 |
| accttcccct cccctaaaac caatctccag aactttttgg actataaatt tcttggtttg | 11820 |
| acttctggag aactgttcag aatattactt tgcatttcaa attacaaact taccttggtg | 11880 |
| tatcttttc ttacaagctg cctaaatgaa tatttggtat atattggtag ttttattact | 11940 |
| atagtaaatc aaggaaatgc agtaaactta aaatgtcttt aagaaagccc tgaaatcttc | 12000 |
| atgggtgaaa ttagaaatta tcaactagat aatagtatag ataaatgaat ttgtagctaa | 12060 |
| ttcttgctag ttgttgcatc cagagagctt tgaataacat cattaatcta ctctttagcc | 12120 |
| ttgcatggta tgctatgagg ctcctgttct gttcaagtat tctaatcaat ggctttgaaa | 12180 |
| agtttatcaa atttacatac agatcacaag cctaggagaa ataactaatt cacagatgac | 12240 |
| agaattaaga ttataaaaga tttttttttt gtaattttag tagagacagg gttgccattg | 12300 |
| tattccagcc ttggcgacag agcaagactc tgcctcaaaa aaaaaaaaa aaaggttttg | 12360 |
| gcaagctgga actctttctg caaatgacta agatagaaaa ctgccaagga caaatgagga | 12420 |
| gtagttagat tttgaaaata ttaatcatag aatagttgtt gtatgctaag tcactgaccc | 12480 |
| atattatgta cagcatttct gatctttact ttgcaagatt agtgatacta tcccaataca | 12540 |
| ctgctggaga aatcagaatt tggagaaata agttgtccaa gcaagaaga tagtaaatta | 12600 |
| taagtacaag tgtaatatgg acagtatcta acttgaaaag atttcaggcg aaaagaatct | 12660 |
| ggggtttgcc agtcagttgc tcaaaaggtc aatgaaaacc aaatagtgaa gctatcagag | 12720 |
| aagctaataa attatagact gcttgaacag ttgtgtccag attaagggag ataatagctt | 12780 |
| tcccaccta ctttgtgcag gtcatacctc cccaaagtgt ttacctaatc agtaggttca | 12840 |
| caaactcttg gtcattatag tatatgccta aaatgtatgc acttaggaat gctaaaaatt | 12900 |
| taaatatggt ctaaagcaaa taaaagcaaa gaggaaaaac tttggacagc gtaaagacta | 12960 |
| gaatagtctt ttaaaaagaa agccagtata ttggtttgaa atatagagat gtgtcccaat | 13020 |
| ttcaagtatt ttaattgcac cttaatgaaa ttatctattt tctatagatt ttagtactat | 13080 |
| tgaatgtatt actttactgt tacctgaatt tattataaag tgtttttgaa taaataattc | 13140 |
| taaaagc | 13147 |

<210> SEQ ID NO 16
<211> LENGTH: 2955
<212> TYPE: DNA
<213> ORGANISM: homo sapiens
<220> FEATURE:
<221> NAME/KEY: misc_feature
<223> OTHER INFORMATION: mRNA of isoform b of IRF5 NM_001098627

<400> SEQUENCE: 16

| | |
|---|---|
| gcagaaagcg gaactgagcc cgcgtgttct gaggccaggg cagggctgga gcgttctgaa | 60 |
| cacctccccg tcccagcccc tgggccaggc aagggccggc cttacctctc ctgggttggt | 120 |
| ggcagcagag ctgggctctg agggaggcct gcaatgtgag acagtagcag ctcagaggcg | 180 |
| gcactaggca ggtgcaaccc caaaagaccc ctctgccatg aaccagtcca tcccagtggc | 240 |
| tcccaccca ccccgccgcg tgcggctgaa gccctggctg gtggcccagg tgaacagctg | 300 |
| ccagtaccca gggcttcaat gggtcaacgg ggaaaagaaa ttattctgca tcccctggag | 360 |
| gcatgccaca aggcatggtc ccagccagga cggagataac accatcttca aggcctgggc | 420 |
| caaggagaca gggaaataca ccgaaggcgt ggatgaagcc gatccggcca agtgaaggc | 480 |
| caacctgcgc tgtgccctta caagagccg ggacttccgc ctcatctacg acgggccccg | 540 |

```
ggacatgcca cctcagccct acaagatcta cgaggtctgc tccaatggcc ctgctcccac      600
agactcccag cccctgagg attactcttt tggtgcagga gaggaggagg aagaagagga       660
agagctgcag aggatgttgc caagcctgag cctcacagag gatgtcaagt ggccgcccac     720
tctgcagccg cccactctgc ggccgcctac tctgcagccg cccactctgc agccgccgt      780
ggtgctgggt cccctgctc cagaccccag cccctggct cctcccctg caaccctgc         840
tggcttcagg gagcttctct ctgaggtcct ggagcctggg cccctgcctg ccagcctgcc     900
ccctgcaggc gaacagctcc tgccagacct gctgatcagc ccccacatgc tgcctctgac     960
cgacctggag atcaagtttc agtaccgggg gcggccaccc cgggccctca ccatcagcaa    1020
ccccccatggc tgccggctct tctacagcca gctggaggcc acccaggagc aggtggaact   1080
cttcggcccc ataagcctgg agcaagtgcg cttccccagc cctgaggaca tcccagtga    1140
caagcagcgc ttctacacga accagctgct ggatgtcctg gaccgcgggc tcatcctcca    1200
gctacagggc caggaccttt atgccatccg cctgtgtcag tgcaaggtgt tctggagcgg   1260
gccttgtgcc tcagcccatg actcatgccc caaccccatc cagcgggagg tcaagaccaa   1320
gcttttcagc ctggagcatt ttctcaatga gctcatcctg ttccaaaagg gccagaccaa   1380
caccccacca cccttcgaga tcttcttctg ctttggggaa gaatggcctg accgcaaacc   1440
ccgagagaag aagctcatta ctgtacaggt ggtgcctgta gcagctcgac tgctgctgga   1500
gatgttctca ggggagctat cttggtcagc tgatagtatc cggctacaga tctcaaaccc   1560
agacctcaaa gaccgcatgg tggagcaatt caaggagctc catcacatct ggcagtccca   1620
gcagcggttg cagcctgtgg cccaggcccc tcctggagca ggccttggtg ttggccaggg   1680
gccctggcct atgcacccag ctggcatgca ataacaaggc tgcagacggt gactggccct   1740
ggcttcctgg gtgcggtgc ggactgatgt ggagatgtga cagccccgat gagcacctgg    1800
ctggctgcag ggtcctacct ctgggtttcc tggaagtgga tttgggccaa gaaggagagg   1860
gagaaaggcc cgagccctg ccttcccggg cctttctctc ctgggctgtc tctggtctgg    1920
tcagcctggc tctcgggaaa ttcagccatg agcagggaaa gaactctccc aaccctgggg   1980
cctagctgta taggaggaat tgcctaaggg tggcccactc ttgtgattgc cccatttcct   2040
ctggcaacaa aagccagagt gttgtgggcc aagtcccccc acagggcctc tgcagggcat   2100
ggccctgatt tccctggttt gagactcact tcctcatctc cctgtcctct gagataaat    2160
gagtgagcac ttaggtatca tatcagatgc tcaaggctgg cagctacccc cttcttgaga   2220
gtccaagaac ctggagcaga ataatttttt atgtattttt ggattaatga atgttaaaaa   2280
cagactcagc tgtttctttc cttttactac taccagttgc tcccatgctg ctccaccagg   2340
ccctgtttcg gatgccaact ggcccactcc ccaagcactt gccccagct tgcgaccatt    2400
ggcactggga gggcctggct tctgggctga tgggtcagtt gggccttcat aaacactcac   2460
ctggctggct ttgccttcca ggaggaagct ggctgaagca agggtgtgga atttttaaatg  2520
tgtgcacagt ctggaaaact gtcagaatca gttttcccat aaaagggtgg gctagcattg   2580
cagctgcatt tgggaccatt caaatctgtc actctcttgt gtatattcct gtgctattaa   2640
atatatcagg gcagtgcatg taaatcatcc tgatatattt aatatattta ttatattgtc   2700
ccccgaggtg gggacagtga gtgagttctc ttagtccccc cagagctggt tgttaaagag   2760
cctggcacct acccgctctc acttcatctg tgtcatctct gcacactcca gcccactttc   2820
tgccttcagc cattgagtgg aagctgcccc aggcccttac caggtgcaga tgcccaatct   2880
tgatgcccag ccatcagaac tgtgagccaa ataaaccttt ttctgtataa attacccaaa   2940
```
aaaaaaaaaa aaaaa                                                                2955

<210> SEQ ID NO 17
<211> LENGTH: 2910
<212> TYPE: DNA
<213> ORGANISM: homo sapiens
<220> FEATURE:
<221> NAME/KEY: misc_feature
<223> OTHER INFORMATION: mRNA of isoform d of IRF5 NM_001098629

<400> SEQUENCE: 17

```
agtgcccggc aggttggcgg accggcggga ggcgcagcct gggcagagct cagcttggtc      60
ccgccgcccg gccggtgctc cctggcgcag ccacgcaggc gcaccgcaga cagacccctc     120
tgccatgaac cagtccatcc cagtggctcc caccccaccc cgccgcgtgc ggctgaagcc     180
ctggctggtg gcccaggtga acagctgcca gtacccaggg cttcaatggg tcaacgggga     240
aaagaaatta ttctgcatcc cctggaggca tgccacaagg catggtccca gccaggacgg     300
agataacacc atcttcaagg cctgggccaa ggagacaggg aaatacaccg aaggcgtgga     360
tgaagccgat ccggccaagt ggaaggccaa cctgcgctgt gcccttaaca gagccgggga     420
cttccgcctc atctacgacg ggccccggga catgccacct cagccctaca gatctacga     480
ggtctgctcc aatggccctg ctcccacaga ctcccagccc cctgaggatt actcttttgg     540
tgcaggagag gaggaggaag aagaggaaga gctgcagagg atgttgccaa gcctgagcct     600
cacagatgca gtgcagtctg cccccacat gacacctat tctttactca agaggatgt      660
caagtggccg cccactctgc agccgcccac tctgcggccg cctactctgc agccgcccac     720
tctgcagccg cccgtggtgc tgggtccccc tgctccagac ccagccccc tggctcctcc     780
ccctggcaac cctgctggct tcagggagct tctctctgag gtcctggagc ctgggccct      840
gcctgccagc ctgccccctg caggcgaaca gctcctgcca gacctgctga tcagccccca     900
catgctgcct ctgaccgacc tggagatcaa gtttcagtac cggggcggc cacccccggc     960
cctcaccatc agcaaccccc atggctgccg gctcttctac agccagctgg aggccaccca    1020
ggagcaggtg gaactcttcg gccccataag cctggagcaa gtgcgcttcc ccagccctga    1080
ggacatcccc agtgacaagc agcgcttcta cacgaaccag ctgctggatg tcctggaccg    1140
cgggctcatc ctccagctac agggccagga cctttatgcc atccgcctgt gtcagtgcaa    1200
ggtgttctgg agcgggcctt gtgcctcagc ccatgactca tgccccaacc ccatccagcg    1260
ggaggtcaag accaagcttt tcagcctgga gcattttctc aatgagctca tcctgttcca    1320
aaagggccag accaacaccc caccacccctt cgagatcttc ttctgctttg ggaagaatg    1380
gcctgaccgc aaaccccgag agaagaagct cattactgta caggtggtgc ctgtagcagc    1440
tcgactgctg ctggagatgt tctcagggga gctatcttgg tcagctgata gtatccggct    1500
acagatctca aacccagacc tcaaagaccg catggtggag caattcaagg agctccatca    1560
catctggcag tcccagcagc ggttgcagcc tgtggcccag gcccctcctg agcaggcct     1620
tggtgttggc cagggggccct ggcctatgca cccagctggc atgcaataac aaggctgcag    1680
acggtgactg gccctggctt cctggtggcc ggtgcggact gatgtggaga tgtgacagcc    1740
ccgatgagca cctggctggc tgcagggtcc tacctctggg tttcctggaa gtggatttgg    1800
gccaagaagg agaggagaa aggcccgagc ccctgcctt ccgggccttt ctctcctggg      1860
ctgtctctgg tctggtcagc ctggctctcg ggaaattcag cctgagcag ggaaagaact     1920
ctcccaaccc tggggcctag ctgtataggaggaattgcct aagggtggcc cactcttgtg    1980
```

```
attgccccat tccctctggc aacaaaagcc agagtgttgt gggccaagtc cccccacagg    2040
gcctctgcag ggcatggccc tgatttccct ggtttgagac tcacttcctc atctccctgt    2100
cctctgagat aatatgagtg agcacttagg tatcatatca gatgctcaag gctggcagct    2160
acccccttct tgagagtcca agaacctgga gcagaaataa ttttttatgta tttttggatt    2220 aatgaatgtt aaaaacagac tcagctgttt ctttccttt actactacca gttgctccca     2280
tgctgctcca ccaggccctg tttcggatgc caactggccc actccccaag cacttgcccc    2340
cagcttgcga ccattggcac tgggagggcc tggcttctgg gctgatgggt cagttgggcc    2400
ttcataaaca ctcacctggc tggctttgcc ttccaggagg aagctggctg aagcaagggt    2460
gtggaatttt aaatgtgtgc acagtctgga aaactgtcag aatcagtttt cccataaaag    2520
ggtgggctag cattgcagct gcatttggga ccattcaaat ctgtcactct cttgtgtata    2580
ttcctgtgct attaaatata tcagggcagt gcatgtaaat catcctgata tatttaatat    2640
atttattata ttgtcccccg aggtggggac agtgagtgag ttctcttagt cccccccagag   2700 ctggttgtta aagagcctgg cacctacccg ctctcacttc atctgtgtca tctctgcaca    2760
ctccagccca cttctgcct tcagccattg agtggaagct gccccaggcc cttaccaggt    2820
gcagatgccc aatcttgatg cccagccatc agaactgtga gccaaataaa ccttttctg    2880 tataaattac ccaaaaaaaa aaaaaaaaaa                                     2910
```

```
<210> SEQ ID NO 18
<211> LENGTH: 498
<212> TYPE: PRT
<213> ORGANISM: homo sapiens
<220> FEATURE:
<221> NAME/KEY: MISC_FEATURE
<223> OTHER INFORMATION: proteic sequence of isoform b of IRF5
      NP_001092097

<400> SEQUENCE: 18

Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
            20                  25                  30

Leu Gln Trp Val Asn Gly Glu Lys Lys Leu Phe Cys Ile Pro Trp Arg
        35                  40                  45

His Ala Thr Arg His Gly Pro Ser Gln Asp Gly Asp Asn Thr Ile Phe
    50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
            100                 105                 110

Gln Pro Tyr Lys Ile Tyr Glu Val Cys Ser Asn Gly Pro Ala Pro Thr
        115                 120                 125

Asp Ser Gln Pro Pro Glu Asp Tyr Ser Phe Gly Ala Gly Glu Glu Glu
    130                 135                 140

Glu Glu Glu Glu Glu Leu Gln Arg Met Leu Pro Ser Leu Ser Leu Thr
145                 150                 155                 160

Glu Asp Val Lys Trp Pro Pro Thr Leu Gln Pro Pro Thr Leu Arg Pro
                165                 170                 175

Pro Thr Leu Gln Pro Pro Thr Leu Gln Pro Pro Val Val Leu Gly Pro
```

180                 185                 190
Pro Ala Pro Asp Pro Ser Pro Leu Ala Pro Pro Gly Asn Pro Ala
        195                 200                 205

Gly Phe Arg Glu Leu Leu Ser Glu Val Leu Glu Pro Gly Pro Leu Pro
        210                 215                 220

Ala Ser Leu Pro Pro Ala Gly Glu Gln Leu Leu Pro Asp Leu Leu Ile
225                 230                 235                 240

Ser Pro His Met Leu Pro Leu Thr Asp Leu Glu Ile Lys Phe Gln Tyr
                245                 250                 255

Arg Gly Arg Pro Pro Arg Ala Leu Thr Ile Ser Asn Pro His Gly Cys
            260                 265                 270

Arg Leu Phe Tyr Ser Gln Leu Glu Ala Thr Gln Glu Gln Val Glu Leu
        275                 280                 285

Phe Gly Pro Ile Ser Leu Glu Gln Val Arg Phe Pro Ser Pro Glu Asp
        290                 295                 300

Ile Pro Ser Asp Lys Gln Arg Phe Tyr Thr Asn Gln Leu Leu Asp Val
305                 310                 315                 320

Leu Asp Arg Gly Leu Ile Leu Gln Leu Gln Gly Gln Asp Leu Tyr Ala
                325                 330                 335

Ile Arg Leu Cys Gln Cys Lys Val Phe Trp Ser Gly Pro Cys Ala Ser
            340                 345                 350

Ala His Asp Ser Cys Pro Asn Pro Ile Gln Arg Glu Val Lys Thr Lys
        355                 360                 365

Leu Phe Ser Leu Glu His Phe Leu Asn Glu Leu Ile Leu Phe Gln Lys
        370                 375                 380

Gly Gln Thr Asn Thr Pro Pro Pro Phe Glu Ile Phe Phe Cys Phe Gly
385                 390                 395                 400

Glu Glu Trp Pro Asp Arg Lys Pro Arg Glu Lys Lys Leu Ile Thr Val
                405                 410                 415

Gln Val Val Pro Val Ala Ala Arg Leu Leu Leu Glu Met Phe Ser Gly
            420                 425                 430

Glu Leu Ser Trp Ser Ala Asp Ser Ile Arg Leu Gln Ile Ser Asn Pro
        435                 440                 445

Asp Leu Lys Asp Arg Met Val Glu Gln Phe Lys Glu Leu His His Ile
        450                 455                 460

Trp Gln Ser Gln Gln Arg Leu Gln Pro Val Ala Gln Ala Pro Pro Gly
465                 470                 475                 480

Ala Gly Leu Gly Val Gly Gln Gly Pro Trp Pro Met His Pro Ala Gly
                485                 490                 495

Met Gln

<210> SEQ ID NO 19
<211> LENGTH: 514
<212> TYPE: PRT
<213> ORGANISM: homo sapiens
<220> FEATURE:
<221> NAME/KEY: MISC_FEATURE
<223> OTHER INFORMATION: proteic sequence of isoform d of IRF5
    NP_001092099

<400> SEQUENCE: 19

Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
            20                  25                  30

-continued

```
Leu Gln Trp Val Asn Gly Glu Lys Lys Leu Phe Cys Ile Pro Trp Arg
         35                  40                  45
His Ala Thr Arg His Gly Pro Ser Gln Asp Gly Asp Asn Thr Ile Phe
 50                  55                  60
Lys Ala Trp Ala Lys Glu Thr Gly Lys Tyr Thr Glu Gly Val Asp Glu
 65                  70                  75                  80
Ala Asp Pro Ala Lys Trp Lys Ala Asn Leu Arg Cys Ala Leu Asn Lys
                 85                  90                  95
Ser Arg Asp Phe Arg Leu Ile Tyr Asp Gly Pro Arg Asp Met Pro Pro
             100                 105                 110
Gln Pro Tyr Lys Ile Tyr Glu Val Cys Ser Asn Gly Pro Ala Pro Thr
         115                 120                 125
Asp Ser Gln Pro Pro Glu Asp Tyr Ser Phe Gly Ala Gly Glu Glu Glu
    130                 135                 140
Glu Glu Glu Glu Glu Leu Gln Arg Met Leu Pro Ser Leu Ser Leu Thr
145                 150                 155                 160
Asp Ala Val Gln Ser Gly Pro His Met Thr Pro Tyr Ser Leu Leu Lys
                165                 170                 175
Glu Asp Val Lys Trp Pro Pro Thr Leu Gln Pro Pro Thr Leu Arg Pro
            180                 185                 190
Pro Thr Leu Gln Pro Pro Thr Leu Gln Pro Pro Val Val Leu Gly Pro
        195                 200                 205
Pro Ala Pro Asp Pro Ser Pro Leu Ala Pro Pro Gly Asn Pro Ala
    210                 215                 220
Gly Phe Arg Glu Leu Leu Ser Glu Val Leu Glu Pro Gly Pro Leu Pro
225                 230                 235                 240
Ala Ser Leu Pro Pro Ala Gly Glu Gln Leu Leu Pro Asp Leu Leu Ile
                245                 250                 255
Ser Pro His Met Leu Pro Leu Thr Asp Leu Glu Ile Lys Phe Gln Tyr
            260                 265                 270
Arg Gly Arg Pro Pro Arg Ala Leu Thr Ile Ser Asn Pro His Gly Cys
        275                 280                 285
Arg Leu Phe Tyr Ser Gln Leu Glu Ala Thr Gln Glu Gln Val Glu Leu
    290                 295                 300
Phe Gly Pro Ile Ser Leu Glu Gln Val Arg Phe Pro Ser Pro Glu Asp
305                 310                 315                 320
Ile Pro Ser Asp Lys Gln Arg Phe Tyr Thr Asn Gln Leu Leu Asp Val
                325                 330                 335
Leu Asp Arg Gly Leu Ile Leu Gln Leu Gln Gly Gln Asp Leu Tyr Ala
            340                 345                 350
Ile Arg Leu Cys Gln Cys Lys Val Phe Trp Ser Gly Pro Cys Ala Ser
        355                 360                 365
Ala His Asp Ser Cys Pro Asn Pro Ile Gln Arg Glu Val Lys Thr Lys
    370                 375                 380
Leu Phe Ser Leu Glu His Phe Leu Asn Glu Leu Ile Leu Phe Gln Lys
385                 390                 395                 400
Gly Gln Thr Asn Thr Pro Pro Phe Glu Ile Phe Phe Cys Phe Gly
                405                 410                 415
Glu Glu Trp Pro Asp Arg Lys Pro Arg Glu Lys Lys Leu Ile Thr Val
            420                 425                 430
Gln Val Val Pro Val Ala Ala Arg Leu Leu Leu Glu Met Phe Ser Gly
        435                 440                 445
Glu Leu Ser Trp Ser Ala Asp Ser Ile Arg Leu Gln Ile Ser Asn Pro
```

-continued

```
            450                 455                 460
Asp Leu Lys Asp Arg Met Val Glu Gln Phe Lys Glu Leu His His Ile
465                 470                 475                 480

Trp Gln Ser Gln Gln Arg Leu Gln Pro Val Ala Gln Ala Pro Pro Gly
                485                 490                 495

Ala Gly Leu Gly Val Gly Gln Gly Pro Trp Pro Met His Pro Ala Gly
                500                 505                 510

Met Gln
```